US012642876B1

(12) United States Patent
Liu et al.

(10) Patent No.: US 12,642,876 B1
(45) Date of Patent: Jun. 2, 2026

(54) CHOLECYSTOKININ-2 RECEPTOR TARGETED COMPOUNDS AND USE THEREOF

(71) Applicant: Perspective Therapeutics, Inc., Seattle, WA (US)

(72) Inventors: Dijie Liu, Iowa City, IA (US); Mengshi Li, Iowa City, IA (US); Nicholas Baumhover, Iowa City, IA (US); M M Hasibuzzaman, Iowa City, IA (US); Dulanjali Thennakoon, Iowa City, IA (US); Zhiming Dai, Iowa City, IA (US); Michael K. Schultz, Iowa City, IA (US)

(73) Assignee: Perspective Therapeutics, Inc., Seattle, WA (US)

( * ) Notice: Subject to any disclaimer, the term of this patent is extended or adjusted under 35 U.S.C. 154(b) by 0 days.

(21) Appl. No.: 19/375,067

(22) Filed: Oct. 30, 2025

(51) Int. Cl.
*A61K 51/08* (2006.01)

(52) U.S. Cl.
CPC ........ *A61K 51/088* (2013.01); *A61K 2121/00* (2013.01); *A61K 2123/00* (2013.01)

(58) Field of Classification Search
CPC .............. A61K 51/088; A61K 2121/00; A61K 2123/00
See application file for complete search history.

(56) References Cited

U.S. PATENT DOCUMENTS

| | | | |
|---|---|---|---|
| 10,874,753 | B2 | 12/2020 | Driver et al. |
| 11,344,623 | B2 | 5/2022 | Low et al. |
| 11,623,014 | B2 | 4/2023 | Behe et al. |
| 11,826,436 | B2 | 11/2023 | Blower et al. |
| 12,049,518 | B2 | 7/2024 | Von Guggenberg Zu Riedhofen et al. |
| 12,358,966 | B2 | 7/2025 | Ostertag et al. |
| 12,427,209 | B2 | 9/2025 | Perrin et al. |
| 2022/0401592 | A1 | 12/2022 | Pomper et al. |
| 2024/0091390 | A1 | 3/2024 | Von Guggenberg Zu Riedhofen et al. |

FOREIGN PATENT DOCUMENTS

| | | | |
|---|---|---|---|
| WO | 2023173174 | A1 | 9/2023 |
| WO | 2023191839 | A2 | 10/2023 |
| WO | 2023201435 | A1 | 10/2023 |
| WO | 2024061483 | A1 | 3/2024 |

OTHER PUBLICATIONS

Dillemuth et al. Rapid cleavage of 6-[18F]fluoronicotinic acid prosthetic group governs BT12 glioblastoma xenograft uptake: implications for radiolabeling design of biomolecules. EJNMMI radiopharm. chem. 10, 40 (2025).
Berge et al. Pharmaceutical salts. J Pharm Sci. Jan. 1977;66(1):1-19. doi: 10.1002/jps.2600660104. PMID: 833720.
Remington—The Science and Practice of Pharmacy, 21st edition (Gennaro et al editors. Lippincott Williams & Wilkins Philadelphia).
Maina et al. Preclinical pharmacokinetics, biodistribution, radiation dosimetry and toxicity studies required for regulatory approval of a phase I clinical trial with 111In-CP04 in medullary thyroid carcinoma patients, European Journal of Pharmaceutical Sciences, vol. 91, 2016, pp. 236-242.
Lipiński et al. Structural studies on radiopharmaceutical DOTA-minigastrin analogue (CP04) complexes and their interaction with CCK2 receptor. EJNMMI Res 8, 33 (2018).
Li, M., et al., Automated cassette-based production of high specific activity [(203/212)Pb]peptide-based theranostic radiopharmaceuticals for image-guided radionuclide therapy for cancer. Appl Radiat Isot, 2017. 127: p. 52-60.
Klingler, M., et al., DOTA-MGS5, a New Cholecystokinin-2 Receptor-Targeting Peptide Analog with an Optimized Targeting Profile for Theranostic Use. J Nucl Med, 2019. 60(7): p. 1010-1016.
Lee, D., et al., Structural modifications toward improved lead-203/lead-212 peptide-based image-guided alpha-particle radiopharmaceutical therapies for neuroendocrine tumors. Eur J Nucl Med Mol Imaging, 2024. 51(4): p. 1147-1162.
Li, M., et al., Preclinical Evaluation of a Lead Specific Chelator (PSC) Conjugated to Radiopeptides for (203)Pb and (212)Pb-Based Theranostics. Pharmaceutics, 2023. 15(2).
Ocak, M., et al., Comparison of biological stability and metabolism of CCK2 receptor targeting peptides, a collaborative project under Cost BM0607. Eur J Nucl Med Mol Imaging, 2011. 38(8): p. 1426-35.
Günther, T., et al., Preclinical Evaluation of Minigastrin Analogs and Proof-of-Concept [(68)Ga]Ga-DOTA-CCK-66 PET/CT in 2 Patients with Medullary Thyroid Cancer. J Nucl Med, 2024. 65(1): p. 33-39.
Viering, O., et al., Biodistribution and Radiation Dosimetry for 68 Ga-DOTA-CCK-66, a Novel CCK 2 R-Targeting Compound for Imaging of Medullary Thyroid Cancer. Clin Nucl Med, 2024. 49(12): p. 1091-1097.
Holzleitner, N., et al., Preclinical evaluation of (225)Ac-labeled minigastrin analog DOTA-CCK-66 for Targeted Alpha Therapy. Eur J Nucl Med Mol Imaging, 2025. 52(2): p. 458-468.
Sauter AW et al. Targeting of the Cholecystokinin-2 Receptor with the Minigastrin Analog 177Lu-DOTA-PP-F11N: Does the Use of Protease Inhibitors Further Improve In Vivo Distribution? J Nucl Med 2019; 60:393-399.
Viering O. et al. CCK2 Receptor-Targeted PET/CT in Medullary Thyroid Cancer Using [68Ga]Ga-DOTA-CCK-66. J Nucl Med. Mar. 1, 2024;65(3):493-494.
Lezaic L. et al. [111In]In-CP04 as a novel cholecystokinin-2 receptor ligand with theranostic potential in patients with progressive or metastatic medullary thyroid cancer: final results of a GRAN-T-MTC Phase I clinical trial. Eur J Nucl Med Mol Imaging 50, 892-907 (2023).
Rottenburger et al. Cholecystokinin 2 Receptor Agonist 177Lu-PP-F11N for Radionuclide Therapy of Medullary Thyroid Carcinoma: Results of the Lumed Phase 0a Study. J Nucl Med. Apr. 2020;61(4):520-526.

*Primary Examiner* — Robert S Cabral
(74) *Attorney, Agent, or Firm* — Bryan Cave Leighton Paisner LLP

(57) ABSTRACT

The present disclosure provides, inter alia, novel compounds targeting cholecystokinin-2 receptor (CCK2R) expressed on the surface of cancer cells. Also provided are methods for imaging, diagnosing, and/or treating cancers using the same.

9 Claims, 14 Drawing Sheets

Specification includes a Sequence Listing.

CHOLECYSTOKININ-2 RECEPTOR TARGETED COMPOUNDS AND USE THEREOF

FIELD OF THE DISCLOSURE

The present disclosure generally relates, inter alia, novel compounds targeting cholecystokinin-2 receptor (CCK2R) expressed on cell surface, and methods for imaging, diagnosing, and/or treating cancers using the same.

INCORPORATION BY REFERENCE OF SEQUENCE LISTING

This application contains references to amino acids and/or nucleic acid sequences that have been filed concurrently herewith as sequence listing XML file "PTX-024-seq.xml", file size of 46,741 bytes, created on Nov. 13, 2025. The aforementioned sequence listing is hereby incorporated by reference in its entirety pursuant to 37 C.F.R. § 1.52(e)(5).

BACKGROUND OF THE DISCLOSURE

Cholecystokinin-2 receptor (CCK2R), a member of the G protein-coupled receptor (GPCR) family, interacts with the ligands gastrin and cholecystokinin (CCK), both of which are critical growth factors in gastrointestinal tissues and central nervous system. Elevated levels of gastrin have been demonstrated to specifically promote cancer cell proliferation through CCK2R. Previous studies have shown that CCK2R and its splice variants are significantly overexpressed in a range of malignancies, including gastric adenocarcinoma, medullary thyroid carcinoma, colorectal, pancreatic, ovarian, and small cell lung cancers. For example, approximately 27% of colorectal cancer (CRC) exhibit CCK2R positivity, with elevated CCK2R expression significantly associated with adverse prognostic outcomes, while the CCK2R has been found in small cell lung cancer (SCLC) patients with a positivity rate of about 38%. Research indicates that aberrant CCK2R expression correlates with specific histological subtypes, particularly mucinous carcinoma (MCA), where overexpression of CCK2R is frequently observed. Furthermore, inactivation of CCK2R has been shown to suppress colonic crypt fission, cellular proliferation, and ultimately inhibit the progression of colorectal cancer.

The high expression of CCK2R in the cancer microenvironment compared with adjacent normal tissue makes CCK2R a potential therapeutic target for drug delivery. In this context, radiopharmaceuticals targeting CCK2R are of particular potential. Radiopharmaceuticals are radiolabeled drugs that are used for imaging and/or therapy of disease. These drugs may be designed with the form Y-L-X, where Y is a chelator that stably chelates with or complexes (i.e., binds tightly) with a radionuclide (e.g., Pb-212, Ac-225, Lu-177, Tb-161, Tb-155, Cu-64, Cu-61, Cu-67, Ga-68, Pb-203) that decays by various forms of radioactive decay modes (e.g., beta-particle emission, alpha-particle emission, positron emission, gamma-ray emission, auger electron emission); X is a targeting molecular structure (e.g., peptide, antibody, small molecule, aptamer) that is designed to bind to cells, often by binding to a cell surface receptor (e.g., GRPR, CCK2R); and L is a molecular linker that connects the chelator Y to the binding moiety X.

The use of certain radionuclides that emit gamma rays enables imaging that can be used for diagnosing and monitoring of disease. Other radionuclides that emit particles, such as beta and alpha particles, are used for treating diseases, such as cancers. In some cases, the radionuclides intended for the treatment of cancer or other diseases, decay further to a series of radionuclide progeny (often referred to as daughter radionuclides or "daughters") that may or may not be chelated or complexed with/by the chelator. The preparation of radiopharmaceuticals involves a reaction of the Y-L-X precursor with the radionuclide. Examples of radionuclides used for this purpose that have a series of daughter radionuclide progeny in their series include Pb-212, Ac-225, and Lu-177.

Over the past two decades, a variety of radiolabeled CCK2R targeted peptides have been synthesized and characterized for imaging/diagnosing. Most of the peptides have the C-terminal CCK2R-binding tetrapeptide sequence Trp-Met-Asp-Phe in common or derivatives thereof. The difficulties in the development of clinically useful radiolabeled CCK2R targeted peptides or peptide analogs are related either to high kidney uptake, leading to nephrotoxicity during therapeutic application, or low stability and tumor retention. Thus, there remains a need for radiopharmaceuticals that can be safely and effectively used for the imaging and/or treating of cancers and other diseases that are associated with aberrant CCK2R expression.

SUMMARY OF THE DISCLOSURE

Among the various aspects of the present disclosure may be noted peptidomimetics for therapeutic and diagnostic purposes as well as compositions, methods, uses and kits based on these peptidomimetics. In particular, the peptidomimetics of the present disclosure specifically bind to CCK2R expressing cells, for instance, cancer cells, thus allowing the selective imaging or destruction of cancer cells that express CCK2R. Additionally, the peptidomimetics of the present disclosure have a favorable half-life in serum, in vivo stability, cellular uptake, and/or tumour targeting properties, while retaining low kidney retention of the peptidomimetic. Among the various aspects of the present disclosure may be noted compositions and methods for imaging or treating a subject suffering from cancer associated with aberrant expression of CCK2R. In the present disclosure, among others, various structural modifications of CCK2R targeted peptidomimetics and peptidomimetic conjugates are described.

In general, the compositions, methods, uses and kits of the present disclosure comprise a peptidomimetic that targets CCK2R, the peptidomimetic comprising a sequence of general formula (1):

$$X_0—X_1\text{-Asp-}X_2 \quad (1)$$

wherein $X_0$, $X_1$ and $X_2$ are independently natural (proteinogenic) or unnatural (non-proteinogenic) amino acids, and wherein $X_0$, $X_1$ and $X_2$ are optionally substituted.

In one such embodiment in which the peptidomimetic corresponds to formula (1), $X_0$ is Trp without modification. In some embodiments, $X_0$ is Trp with C(4) substitution wherein the C(4) position is substituted by halo, —CN, —$NO_2$, —$CONH_2$, —O—$C_{1-6}$ alkyl, —OH, $C_{1-6}$ alkyl, $C_{3-6}$ cycloalkyl, $C_{3-6}$ heterocycloalkyl, $C_{6-14}$ aryl, or $C_{6-14}$ heteroaryl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, or $C_{6-14}$ heteroaryl is optionally substituted.

In some embodiments in which the peptidomimetic corresponds to formula (1), $X_1$ has the structure of —N(R)—CH(R)—C(═O)—, and $X_2$ has the structure of —NH—CH (R)—C(═O)—$NH_2$. In some embodiments, R is selected from, but not limited to, hydrogen, halo, —CN, —OH, $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted. Preferably, in one embodiment, R in $X_2$ is selected from unsubstituted or substituted phenyl, benzyl, 1-adamantyl, 1-naphthyl, 2-naphthyl, 1-anthryl, 2-anthryl, 3-anthryl, phenol, and indole. In another embodiment, $X_1$ is selected from the group consisting of unsubstituted or substituted Ala, Leu, Ile, and Nle. In yet another embodiment, $X_2$ is selected from the group consisting of unsubstituted or substituted Phe-$NH_2$, Trp-$NH_2$, and Nal-$NH_2$.

In certain embodiments, the compositions, methods, uses and kits of the present disclosure comprise a peptidomimetic containing the sequence of formula (1A):

(1A)

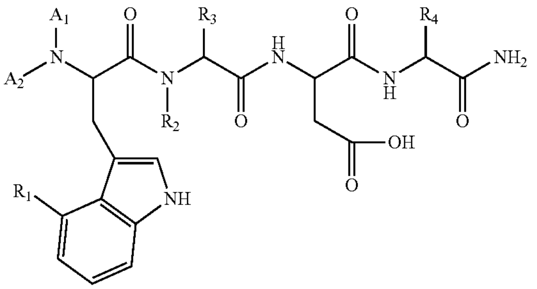

wherein $A_1$ is hydrogen or optionally substituted $C_{1-6}$ alkyl, $A_2$ is hydrogen or a bond connecting the sequence of Formula 1A to the remainder of the peptidomimetic, $R_1$ is selected from the group consisting of hydrogen, halo, —CN, —$NO_2$, —$CONH_2$, —O—$C_{1-6}$ alkyl, —OH, $C_{1-6}$ alkyl, $C_{3-6}$ cycloalkyl, and $C_{3-6}$ heterocycloalkyl, wherein the $C_{1-6}$ alkyl, —O—$C_{1-6}$ alkyl, $C_{3-6}$ cycloalkyl, or $C_{3-6}$ heterocycloalkyl is optionally substituted, $R_2$ is selected from the group consisting of hydrogen, halo, —CN, —OH, and $C_{1-6}$ alkyl, wherein the $C_{1-6}$ alkyl is optionally substituted, $R_3$ is selected from the group consisting of $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted, and $R_4$ is selected from the group consisting of unsubstituted or substituted phenyl, benzyl, 1-adamantyl, 1-naphthyl, 2-naphthyl, 1-anthryl, 2-anthryl, 3-anthryl, phenol, and indole.

In certain embodiments, the compositions, methods, uses and kits of the present disclosure comprise a peptidomimetic containing the sequence of formula (1B):

(1B)

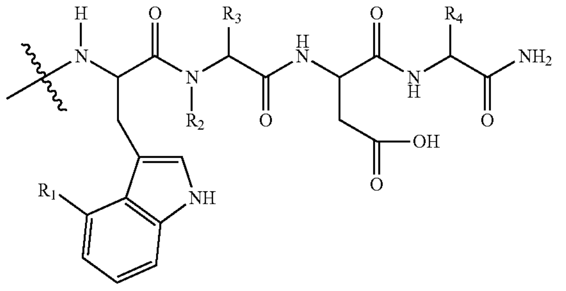

wherein designates the point of attachment of the sequence of formula (1B) to the remainder of the peptidomimetic or radiopharmaceutical compound; wherein:

$R_1$ is selected from the group consisting of hydrogen, halo, —CN, —$NO_2$, —$CONH_2$, —O—$C_{1-6}$ alkyl, —OH, $C_{1-6}$ alkyl, $C_{3-6}$ cycloalkyl, and $C_{3-6}$ heterocycloalkyl, wherein the $C_{1-6}$ alkyl, —O—$C_{1-6}$ alkyl, $C_{3-6}$ cycloalkyl, or $C_{3-6}$ heterocycloalkyl is optionally substituted, $R_2$ is selected from the group consisting of hydrogen, halo, —CN, —OH, and $C_{1-6}$ alkyl, wherein the $C_{1-6}$ alkyl is optionally substituted, $R_3$ is selected from the group consisting of $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted, and $R_4$ is selected from the group consisting of unsubstituted or substituted phenyl, benzyl, 1-adamantyl, 1-naphthyl, 2-naphthyl, 1-anthryl, 2-anthryl, 3-anthryl, phenol, and indole.

In certain embodiments, the compositions, methods, uses and kits of the present disclosure comprise a peptidomimetic corresponding to formula (2):

$$Z\text{-}L\text{-}X_0\text{—}X_1\text{-Asp-}X_2 \quad (2)$$

wherein

Z is a chelator capable of chelating a radionuclide, one or multiple cytotoxic agents, one or multiple prosthetic groups, or one or multiple fluorophore molecules, L is a linker, or absent, $X_0$ is Trp, or Trp with substitution, wherein the substitution is preferably at the C(4) position, and $X_1$ and $X_2$ are independently natural (proteinogenic) or unnatural (non-proteinogenic) amino acids.

In certain embodiments, the compositions, methods, uses and kits of the present disclosure comprise a peptidomimetic corresponding to formula (3):

(3)

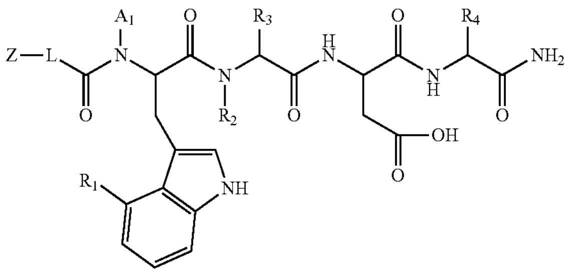

wherein $A_1$ is hydrogen or optionally substituted $C_{1-6}$ alkyl,

L is a linker, or absent, $R_1$ is selected from the group consisting of hydrogen, halo, —CN, —$NO_2$, —$CONH_2$, —O—$C_{1-6}$ alkyl, —OH, $C_{1-6}$ alkyl, $C_{3-6}$ cycloalkyl, and $C_{3-6}$ heterocycloalkyl, wherein the $C_{1-6}$ alkyl, —O—$C_{1-6}$ alkyl, $C_{3-6}$ cycloalkyl, or $C_{3-6}$ heterocycloalkyl is optionally substituted, $R_2$ is selected from the group consisting of hydrogen, halo, —CN, —OH, and $C_{1-6}$ alkyl, wherein the $C_{1-6}$ alkyl is optionally substituted, $R_3$ is selected from the group consisting of $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted, $R_4$ is selected from the group consisting of unsubstituted or substituted phenyl, benzyl, 1-adamantyl, 1-naphthyl, 2-naphthyl, 1-anthryl, 2-anthryl, 3-anthryl, phenol, and indole, and Z is a chelator capable of chelating a radionuclide, one or multiple cytotoxic agents, one or multiple prosthetic groups, or one or multiple fluorophore molecules.

In one embodiment, the present disclosure is directed to a composition, method, use or kit comprising the peptidomimetic of any of formulae (1), (1A), 1(B), (2) or (3) and a radionuclide bonded to the peptidomimetic. In one such embodiment, the present disclosure is directed to a composition, method, use or kit comprising the peptidomimetic of any of formulae (1), (1A), 1 (B), (2) and (3) wherein the peptidomimetic is a radiopharmaceutical compound comprising $^{203}$Pb or $^{212}$Pb chelated to the peptidomimetic. In one such embodiment, the present disclosure is directed to a composition, method, use or kit comprising the peptidomimetic of formula (3) wherein $^{203}$Pb or $^{212}$Pb is chelated with Z.

The present disclosure also provides a method for imaging or diagnosing a subject suffering from a cancer associated with aberrant expression of CCK2R, the method comprising administering to the subject a radiopharmaceutical compound comprising the peptidomimetic of any of formulae (1), (1A), 1(B), (2) and (3) bonded to a radionuclide, and imaging the subject. In one such embodiment, the peptidomimetic corresponds to formula (3) and the radionuclide is any of the radionuclides disclosed herein. In one such embodiment, the peptidomimetic corresponds to formula (3) wherein Z is bonded to $^{203}$Pb or $^{212}$Pb.

The present disclosure also provides a method for treating a subject suffering from a cancer associated with aberrant expression of CCK2R, the method comprising administering to the subject a radiopharmaceutical compound comprising the peptidomimetic of any of formulae (1), (1A), 1(B), (2) and (3) bonded to a radionuclide. In one such embodiment, the radiopharmaceutical compound corresponds to formula (3) and the radionuclide is any of the radionuclides disclosed herein. In one such embodiment, the radiopharmaceutical compound corresponds to formula (3) and the radionuclide is $^{203}$Pb or $^{212}$Pb.

The present disclosure further provides a method of diagnosing and treating a subject suffering from a cancer associated with aberrant expression of CCK2R, the method comprising: administering a radiopharmaceutical compound comprising a peptidomimetic of any of formulae (1), (1A), 1(B), (2) and (3) bonded to a first radionuclide to the subject, imaging the subject to diagnose the subject as being afflicted with the cancer, and administering a peptidomimetic comprising any of formulae (1), (1A), 1(B), (2) and (3) bonded to a second radionuclide to the diagnosed subject. In one such embodiment, the first radionuclide is $^{203}$Pb and the second radionuclide is $^{212}$Pb.

In one embodiment, the present disclosure is directed to a composition, method, use or kit comprising a pharmaceutical composition wherein the pharmaceutical composition comprises a pharmaceutically acceptable excipient and a radiopharmaceutical compound wherein the radiopharmaceutical compound comprises a peptidomimetic corresponding to any of formulae (1), (1A), 1(B), (2) and (3) bonded to a radionuclide. In one such embodiment, the radionuclide is $^{203}$Pb or $^{212}$Pb.

BRIEF DESCRIPTION OF THE DRAWINGS

The following drawings form part of the present specification and are included to further demonstrate certain aspects of and not to limit the scope of the present disclosure. The disclosure may be better understood by reference to one or more of these drawings in combination with the detailed description of specific embodiments presented herein.

DEFINITIONS

Figure 1:
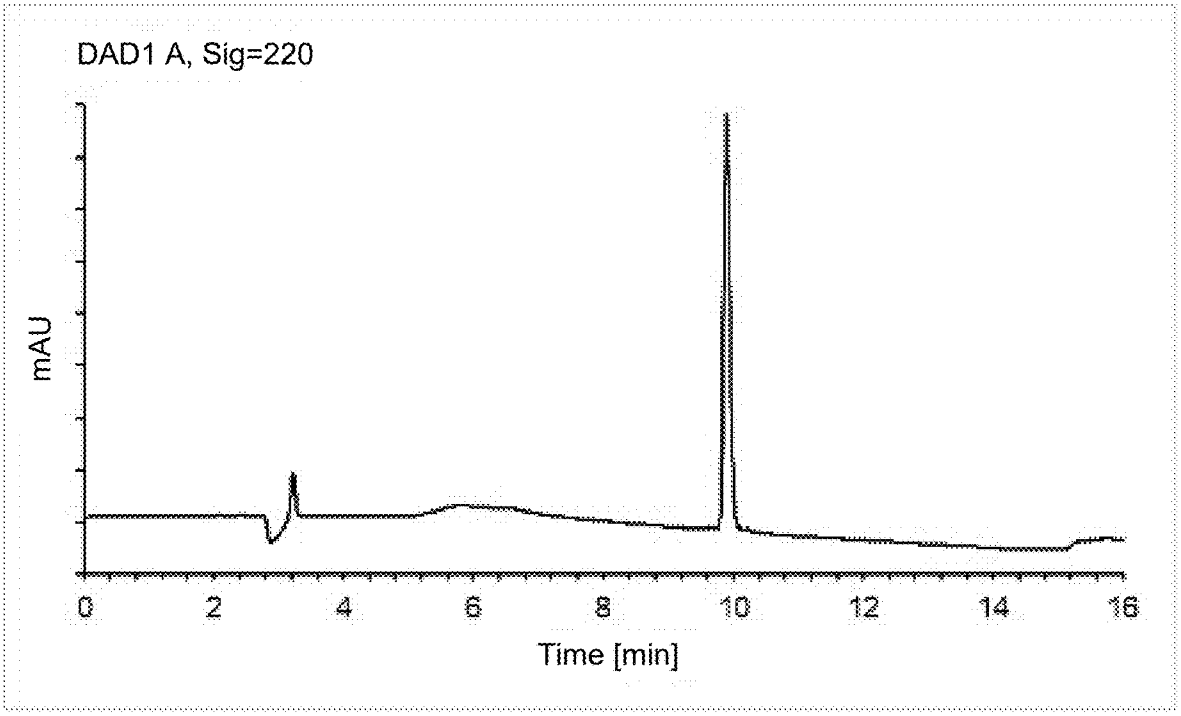
FIG. 1 shows the LC-MS characterization data for PSV-CCK2R-13.
Figure 1:
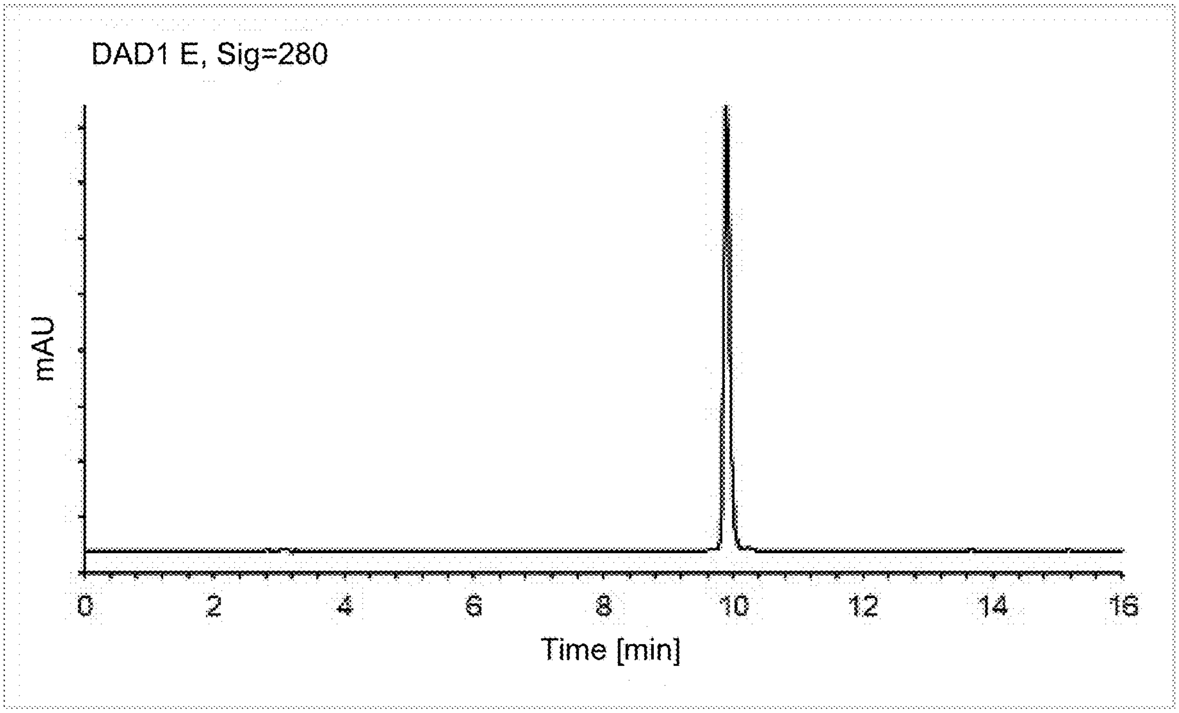
Figure 1:
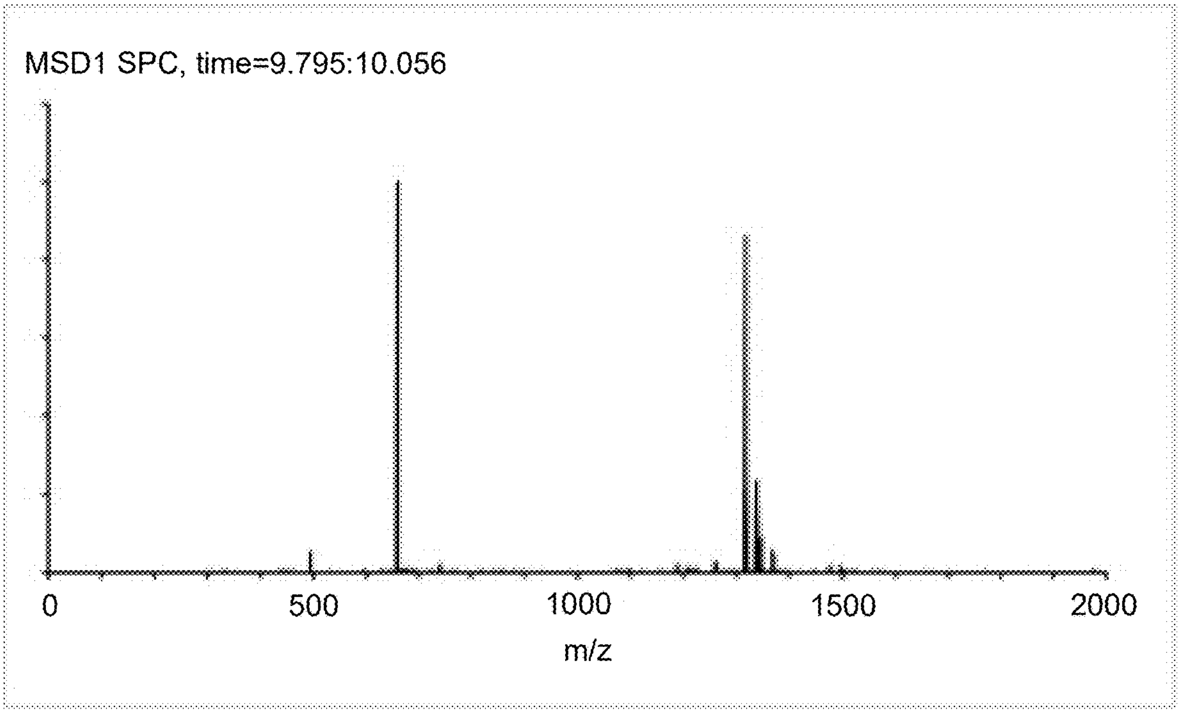

As used herein, the terms “comprising”, “having”, “including”, and “containing” and grammatical variations thereof, are inclusive or open-ended and do not exclude additional, unrecited elements and/or method steps, even if a feature/component defined as a part thereof consists or consists essentially of specified feature(s)/component(s). The term “consisting essentially of” if used herein in connection with a compound, composition, use or method, denotes those additional elements and/or method steps may be present, but that these additions do not materially affect the manner in which the recited compound, composition, method or use functions. The term "consisting of" if used herein in connection with a feature of a compound, composition, use or method, excludes the presence of additional elements and/or method steps in that feature. A compound, composition, use or method described herein as comprising certain elements and/or steps may also, in certain embodiments consist essentially of those elements and/or steps, and in other embodiments consist of those elements and/or steps, whether or not these embodiments are specifically referred to. A use or method described herein as comprising certain elements and/or steps may also, in certain embodiments consist essentially of those elements and/or steps, and in other embodiments consist of those elements and/or steps, whether or not these embodiments are specifically referred to.

A reference to an element by the indefinite article "a" does not exclude the possibility that more than one of the elements is present, unless the context clearly requires that there be one and only one of the elements. The singular forms "a", "an", and "the" include plural referents unless the context clearly dictates otherwise. The use of the word "a" or "an" when used herein in conjunction with the term "comprising" may mean "one", but it is also consistent with the meaning of "one or more", "at least one" and "one or more than one".

In this disclosure, the recitation of numerical ranges by endpoints includes all numbers subsumed within that range including all whole numbers, all integers and, where suitable, all fractional intermediates (e.g., 1 to 5 may include 1, 1.5, 2, 2.75, 3, 3.80, 4, and 5 etc.).

Unless otherwise specified, "certain embodiments," "various embodiments," "an embodiment" and similar terms includes the particular feature(s) described for that embodiment either alone or in combination with any other embodiment or embodiments described herein, whether or not the other embodiments are directly or indirectly referenced and regardless of whether the feature or embodiment is described in the context of a method, product, use, composition, compound, et cetera.

With regard to stereoisomers, it should be understood that a solid line designation for the bonds in the compositions corresponding to the structural formulae disclosed herein for attachment of a substituent group to a chiral carbon atom of the compound may indicate that these groups may lie either in, below or above the plane of the page (i.e., all isomeric forms of the compounds disclosed herein are contemplated, including racemates, racemic mixtures, and individual enantiomers or diastereomers). Certain compounds described herein may exist in tautomeric forms, and all such tautomeric forms of the compounds being within the scope of the disclosure.

The term "aliphatic" denotes saturated and non-aromatic unsaturated hydrocarbyl moieties having, for example, one to about twenty carbon atoms or, in specific embodiments, one to about twelve carbon atoms, one to about ten carbon atoms, one to about eight carbon atoms, or even one to about four carbon atoms. The aliphatic groups include, for example, alkyl moieties such as methyl, ethyl, n-propyl, isopropyl, n butyl, isobutyl, sec-butyl, tert-butyl, pentyl, iso-amyl, hexyl and the like, and alkenyl moieties of comparable chain length.

As used herein, alone or as part of another group, "1-adamantyl" denotes a functional group of the formula

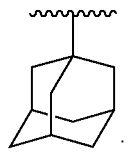

The term "alkyl" as used herein, alone or as part of another group, denotes saturated linear, branched or cyclic carbon radicals having, for example, one to about twenty carbon atoms or, in specific embodiments, one to about twelve carbon atoms. In certain embodiments, alkyl groups are "lower alkyl" groups having one to about six carbon atoms. Examples of such groups include, but are not limited thereto, methyl, ethyl, n-propyl, isopropyl, n butyl, isobutyl, sec-butyl, tert-butyl, pentyl, iso-amyl, hexyl and the like. In more specific embodiments, lower alkyl groups have one to four carbon atoms.

The term "alkenyl" as used herein, alone or as part of another group, denotes linear, branched or cyclic carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In certain embodiments, alkenyl groups are "lower alkenyl" groups having two to about six carbon atoms. Examples of alkenyl groups include, but are not limited thereto, ethenyl, propenyl, allyl, vinyl, butenyl and 4-methylbutenyl. The terms "alkenyl group" and "lower alkenyl group", encompass groups having "cis" or "trans" orientations, or alternatively, "E" or "Z" orientations.

The term "alkylene" as used herein, alone or as part of another group, denotes a linear saturated divalent hydrocarbon radical of one to twenty carbon atoms, or, in specific embodiments, one to about six carbon atoms or a branched saturated divalent hydrocarbon radical of three to twenty carbon atoms unless otherwise stated, e.g., methylene, ethylene, propylene, 1-methylpropylene, 2-methylpropylene, butylene, pentylene, and the like.

The term "alkoxy," as used herein alone or as part of another group, denotes an —$OX^5$ radical, wherein $X^5$ is as defined in connection with the term "alkyl." Exemplary alkoxy moieties include methoxy, ethoxy, propoxy, or 2-propoxy, n-, iso-, or tert-butoxy, cyclohexyloxy and the like.

The term "amide," as used herein, alone or as part of another group, denotes a group having the formula —C(O)N($X^1$)($X^2$), wherein $X^1$ and $X^2$ are as defined in connection with the terms "amine" or "amino." For example, "substituted amide" refers to a group of formula —C(O)N($X^1$)($X^2$), wherein at least one of $X^1$ and $X^2$ are other than hydrogen and "unsubstituted amide," for example, refers to a group of formula —C(O)N($X^1$)($X^2$) wherein each of $X^1$ and $X^2$ are hydrogen.

The terms "amine" and "amino" as used herein, alone or as part of another group, are used interchangeably and denote a group of formula *—N($X^1$)($X^2$), wherein * denotes the point of attachment of the moiety to the remainder of the molecule and $X^1$ and $X^2$ are independently hydrogen, hydrocarbyl, or substituted hydrocarbyl, heteroaryl, or heterocyclo, or $X^1$ and $X^2$ taken together form a substituted or unsubstituted alicyclic, aryl, or heterocyclic moiety, each as defined in connection with such term, typically having from 3 to 8 atoms in the ring. "Substituted amine," for example, refers to a group having the formula —$N(X^1)(X^2)$, wherein at least one of $X^1$ and $X^2$ are other than hydrogen and "unsubstituted amine" refers to a group having the formula —$N(X^1)(X^2)$, wherein each of $X^1$ and $X^2$ are hydrogen.

The term "amino acid," as used herein refers to a compound that contains in its monomeric state at least an amine (—$NH_2$) and a carboxyl (—COOH) functional group. Amino acids as described herein include naturally occurring amino acids (or proteinogenic amino acids) (including L and D isostereomers) and residues thereof, including: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); valine (Val). Unless otherwise limited, amino acid as described herein also includes unnatural amino acid, also called non-proteinogenic amino acid. Non-proteinogenic amino acid is not naturally encoded in the human genetic code or found in the polypeptide chains or proteins. For example, non-proteinogenic amino acids may include analogs of natural amino acids or amino acids derivatives, such as selenocysteine (Sec), naphthylalanine (Nal), anthrylalanine, norleucine (Nle), pyrrolysine, N-formylmethionine, gamma-carboxyglutamate, hydroxyprolinehypusine, pyroglutamic acid, selenomethionine, homoprolin, homoalanine, beta-alanine, 1-naphthylalanine (1-Nal), 2-naphthylalanine (2-Nal), 3-(4-biphenyl-alanine (Bip), 2-pyridylalanine (2-Pal), 3-pyridyl-alanine (3-Pal), 4-pyridyl-alanine (4-Pal), 3-benzothienyl-alanine (Bta), para-, ortho- or meta-substituted phenylalanine, such as para-ethynylphenylalanine, 2-cyano-phenylalanine, 3-cyano-phenylalanine, 4-cyano-phenylalanine, 3-borono-phenylalanine, 4-borono-phenylalanine, 4-trifluoromethyl-phenylalanine, 2-chloro-phenylalanine, 3-chloro-phenylalanine, 4-chloro-phenylalanine, 2-fluoro-phenylalanine, 3-fluoro-phenylalanine, 4-fluoro-phenylalanine, 2-iodo-phenylalanine, 3-iodo-phenylalanine, 4-iodo-phenylalanine, 2-methyl-phenylalanine, 3-methyl-phenylalanine, 4-methyl-phenylalanine, 2-nitro-phenylalanine, 3-nitro-phenylalanine, 4-nitro-phenylalanine, 4-pentafluoro-phenylalanine, phenylglycine (Phg), 4-amino-phenylalanine, 4-methoxy-phenylalanine, 5-hydroxytrptophan, 3, 5-diiodo-tyrosine, 4-benzoyl-phenylalanine, 5-hydroxy-tryptophan, 3, 5-diiodo-tyrosine, 4-benzoyl-phenylalanine (Bpa), cyclohexylglycine (Chg), homophenylalanine (hPhe), homopropargylglycine (Hpg), azidohomoalanine (Aha), cyclohexylalanine (Cha), aminohexanoic acid (Ahx), 2-aminobutanoic acid (Abu), azidonorleucine (Ani), tert-leucine (Tle), 4-amino-carbamoyl-phenylalanine (Aph(Cbm)), 4-amino-hydroorotyl-phenylalanine (Aph(Hor)), S-Acetamidomethyl-L-cysteine (Cys(Acm)), 3-benzothienylalanine, 4-amino-3-hydroxy-6-methylheptanoic acid (Sta), or 2-thienyl-alanine (Thi). The terms unnatural amino acid and non-proteinogenic amino acid are used interchangeable herein.

The terms "amino acid sequence", "peptidomimetic sequence", and "peptide sequence" are used interchangeably herein and denote a series of amino acid residues linked via amide bonds, and depending upon the number of residues in the series comprise a peptide, polypeptide or protein.

As used herein, the term "aralkylene" denotes a chain of 1 to 20 carbon atoms, typically 1 to 12 carbon atoms, more typically 1 to 10 carbon atoms, and most typically 1 to 8 carbon atoms, and in some embodiments 1 to 4 carbon atoms that can be saturated or partially unsaturated, containing one or more aryl moieties. The aryl moiety may be a part of a pendant (or side) group attached to a chain of atoms (e.g.,

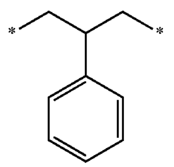 [SMILES: *CC(C*)c1ccccc1]

wherein * denotes the point of attachment of the aralkylene moiety to the remainder of the molecule, or two or more atoms of the aryl moiety may also serve as chain atoms of the aralkylene moiety (e.g.,

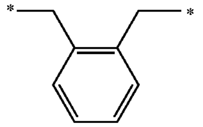 [SMILES: *Cc1ccccc1CC]

The term "aromatic" as used herein, alone or as part of another group, includes "aryl" and "heteroaryl" groups as defined herein.

The terms "aryl" and "Ar" as used herein, alone or as part of another group, are used interchangeably and denote an aromatic group having one or more rings wherein such rings may be attached together in a pendent manner or may be fused. Examples of aryl groups include, but are not limited to, phenyl, naphthyl, biphenyl, and anthryl. Unless specified otherwise, the aryl group may be substituted at one or more ring positions with hydroxyl, optionally substituted alkyl, optionally substituted alkenyl, optionally substituted alkoxy, acyl, acyloxy, amino, aryloxy, carboxy, cyano, halogen, mercapto, oxo, nitro, thiol, sulfo, or the salts thereof.

As used herein, alone or as part of another group, "benzyl" denotes a functional group of the formula

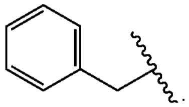 [SMILES: *Cc1ccccc1]

The terms "carbocyclic," "carbocycle," and "carbocyclyl" as used herein alone or as part of another group, are used interchangeably and denote any mono-, bi-, or tricyclic ring system in which the ring atoms are exclusively carbon and the ring system contains at least one aliphatic carbon-carbon bond. For example, the carbocycle may be cyclohexane, cycloheptane, and norbornane. Unless specified otherwise, the carbocyclic group may be substituted at one or more ring positions as described for heterocycles. The terms "carbocycle" and "aryl" are mutually exclusive.

The term "carboxy" and "carboxyl" as used herein alone or as part of another group, are used interchangeably and denote as used herein, alone or as part of another group denotes —COOH.

The term "chelator," as used herein, refers to a molecule with functional groups, such as amine or carboxylic groups, that is capable of forming a complex with a nuclide, for example, a radionuclide. The chelator may contain different donor groups for metal complexation such as oxygen, nitrogen, sulphur, carboxyl, phosphonate, hydroxamate, amine, thiol, thiocarboxylate or derivatives thereof and comprises acyclic and macrocyclic chelators such as polyamino polycarboxylic ligands.

As used herein, the terms “complexed,” “complexes,” and “complexing” are used interchangeably and refer to the general process whereby a metal ion binds with a ligand such as a chelator to form a coordination complex. In this case, the terms “complexed,” “complexes,” and “complexing” have the same meaning as “chelated”, “chelats”, and “chelating”, respectively. For example, the phrase “a peptidomimetic conjugate is complexed with a radionuclide” has the same meaning as “a peptidomimetic conjugate is chelated with a radionuclide”. In this case, the terms “chelated” and “complexed” are used interchangeably.

As used herein the term “coordination complex” and “complex” are used interchangeably and refer to a metal atom or ion bonded to surrounding ligands.

The term “cyano,” as used herein, alone or as part of another group, denotes a group of formula —C≡N.

The term “cyclization” as used herein, refers to the formation of one or more closed rings from a linear peptide or peptide segment by the introduction of a bond or a cyclization moiety.

The terms “cyclization moiety” and “cyclization group” are used interchangeably herein and refer to the residue of a chemical moiety that facilitates cyclization of a linear peptide or peptide segment.

As used herein, “cycloaliphatic” denotes a chain of 1 to 20 carbon atoms, typically 1 to 12 carbon atoms, 1 to 10 carbon atoms, 1 to 8 carbon atoms, and in some embodiments 1 to 4 carbon atoms containing one or more optionally substituted cycloalkyl moieties that can be saturated or at least partially unsaturated (but not aromatic). The cycloalkyl moiety may be a part of a pendant (or side) group attached to a chain of atoms (e.g.,

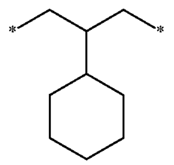

wherein * denotes the point of attachment to the remainder of the molecule, or the chain atoms comprise two or more carbon atoms of the cycloalkyl moiety (e.g.,).

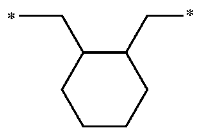 [SMILES: *CC1CCCCC1CC]

Cycloaliphatic excludes aralkylene.

The term “cycloalkyl,” as used herein, alone or as part of another group, denotes a cyclic saturated monovalent bridged or non-bridged hydrocarbon radical of three to ten carbon atoms. Exemplary cycloalkyl moieties include cyclopropyl, cyclobutyl, cyclopentyl, cyclohexyl, adamantyl and bicyclo[2.2.1]heptyl. Unless specified otherwise, the cycloalkyl group may be substituted at one or more ring positions with hydroxyl, optionally substituted alkyl, optionally substituted alkenyl, optionally substituted alkoxy, acyl, acyloxy, amino, aryloxy, carboxy, cyano, halogen, mercapto, oxo, nitro, thiol, sulfo, and the salts thereof.

As used herein, the terms “cytotoxic molecule”, “cytotoxic agent”, and “cytotoxic drug” are used interchangeably and refer to a chemical moiety or chemical molecule that exerts toxicity or cell-killing effect to the cells that the cytotoxic molecule or cytotoxic agent or cytotoxic drug contacts with. Non-limiting examples of such cytotoxic molecule include monomethyl auristatin E (MMAE), DM1 (mertansine), deruxtecan, and calicheamicin. One or multiple cytotoxic agents can be linked to a peptidomimetic disclosed herein.

As used herein, the term “derivative” includes any compound which has been chemically modified without substantially altering its functional character. For example, a derivative may substantially retain one or more characteristic properties of said compound.

As used herein, the term “diagnostic agent” includes an “imaging agent”. As such, a “diagnostic radionuclide” includes radionuclides that are suitable for medical imaging use.

As used herein, the terms “fluorophore”, “fluorophore molecule”, “fluorescent molecule”, and “fluorescent labeling agent” are used interchangeably and refer to a molecule that absorbs light energy at one wavelength and emits fluorescent light at a different wavelength. Non-limiting examples of fluorophore, fluorescent molecule, or fluorescent labeling agent include indocyanine green (ICG), Cy3, Cy5, Cy7, and IRDye800CW.

The terms “halo” and “halogen” as used herein, alone or as part of another group, are used interchangeably and denote halogen atoms such as fluorine, chlorine, bromine, or iodine atoms.

The term “haloalkyl group” as used herein, alone or as part of another group, denotes groups wherein any one or more of the alkyl carbon atoms is substituted with halo as defined herein. Specifically encompassed are monohaloalkyl, dihaloalkyl and polyhaloalkyl groups including perhaloalkyl. A monohaloalkyl group, for example, may have either an iodo, bromo, chloro or fluoro atom within the group. Dihalo and polyhaloalkyl groups may have two or more of the same halo atoms or a combination of different halo groups. “Lower haloalkyl group” encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term “heteroacyl” as used herein, alone or as part of another group denotes an acyl group, —C(O)R group, wherein the R group can be an alkyl, aryl, or heterocyclo as defined herein, and further comprising a heteroatom such as one or more of N, S, and O wherein the heteroatom may be a part of a pendant (or side) group attached to a chain of atoms or may be a chain atom.

The term “heteroaliphatic” as used herein, alone or as part of another group, denotes a cyclic or acyclic chain of 1 to 20 carbon atoms, typically 1 to 12 carbon atoms, more typically 1 to 10 carbon atoms, and most typically 1 to 8 carbon atoms, and in some embodiments 1 to 4 carbon atoms that can be saturated or unsaturated (but not aromatic), containing one or more heteroatoms, such as halogen, oxygen, nitrogen, sulfur, phosphorus, or boron. A heteroatom atom may be a part of a pendant (or side) group attached to a chain of atoms (e.g., *—$CH(OH)CH(NH_2)$—* wherein * denotes the point of attachment to the remainder of the molecule and the carbon atoms are member of a chain of atoms) or it may be one of the chain atoms (e.g., —ROR— or —RNHR— where each R is aliphatic). Heteroaliphatic encompasses heteroalkyl and heterocycloalkylene but does not encompass heteroaralkylene.

The term "heteroalkyl" as used herein, alone or as part of another group, denotes an alkyl group substituted by one or more hetero atoms.

As used herein, "heteroalkylene" refers to a divalent, fully saturated heteroalkyl moiety.

As used herein, "heteroaralkylene" denotes a chain of 1 to 20 carbon atoms, typically 1 to 12 carbon atoms, 1 to 10 carbon atoms, 1 to 8 carbon atoms, and in some embodiments 1 to 4 carbon atoms that can be saturated or unsaturated, containing one or more heteroaryl moieties. The heteroaryl moiety may be a part of a pendant (or side) group attached to a chain of atoms (e.g.,

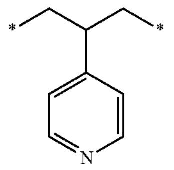 [SMILES: *CC(C*)c1ccncc1]

wherein * denotes the point of attachment to the remainder of the molecule, or the chain atoms comprise two or more carbon atoms of the heteroaryl moiety (e.g.,).

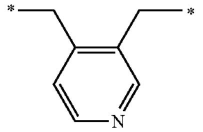 [SMILES: *Cc1ccncc1CC]

The term "heteroatom" denotes an atom other than carbon and hydrogen. Typically, but not exclusively, heteroatoms are selected from the group consisting of halogen, sulfur, phosphorous, nitrogen, boron and oxygen atoms. Groups containing more than one heteroatom may contain different heteroatoms.

The terms "heterocyclic group", "heterocyclic", "heterocycle", "heterocyclyl", and "heterocyclo" as used herein, alone or as part of another group, are used interchangeably and refer to any mono-, bi-, or tricyclic, saturated or unsaturated, aromatic (heteroaryl) or non-aromatic ring having the number of atoms designated, generally from 5 to about 16 ring atoms, where the ring atoms are carbon and at least one heteroatom (nitrogen, sulfur or oxygen), for example, 1 to 4 heteroatoms. For example, heterocyclic groups include four to seven membered cyclic groups containing one, two or three heteroatoms selected from the group consisting of nitrogen, oxygen and sulfur. Typically, a 5-membered ring has 0 to 2 double bonds and 6- or 7-membered ring has 0 to 3 double bonds. The nitrogen or sulfur heteroatoms may optionally be oxidized (e.g., SO, $SO_2$), and any nitrogen heteroatom may optionally be quaternized. Particular non-aromatic heterocycles are morpholinyl (morpholino), pyrrolidinyl, oxiranyl, oxetanyl, tetrahydrofuranyl, 2,3-dihydrofuranyl, 2H-pyranyl, tetrahydropyranyl, thiiranyl, thietanyl, tetrahydrothietanyl, aziridinyl, azetidinyl, 1-methyl-2-pyrrolyl, piperazinyl and piperidinyl. Particular 5-membered heterocycles containing a sulfur or oxygen atom and one to three nitrogen atoms are thiazolyl, in particular thiazol-2-yl and thiazol-2-yl N-oxide, thiadiazolyl, in particular 1,3,4-thiadiazol-5-yl and 1,2,4-thiadiazol-5-yl, oxazolyl, for example oxazol-2-yl, and oxadiazolyl, such as 1,3,4-oxadiazol-5-yl, and 1,2,4-oxadiazol-5-yl. Particular 5-membered ring heterocycles containing 2 to 4 nitrogen atoms include imidazolyl, such as imidazol-2-yl; triazolyl, such as 1,3,4-triazol-5-yl; 1,2,3-triazol-5-yl, 1,2,4-triazol-5-yl, and tetrazolyl, such as 1H-tetrazol-5-yl. Particular benzo-fused 5-membered heterocycles are benzoxazol-2-yl, benzthiazol-2-yl and benzimidazol-2-yl. Particular 6-membered heterocycles contain one to three nitrogen atoms and optionally a sulfur or oxygen atom, for example pyridyl, such as pyrid-2-yl, pyrid-3-yl, and pyrid-4-yl; pyrimidyl, such as pyrimid-2-yl and pyrimid-4-yl; triazinyl, such as 1,3,4-triazin-2-yl and 1,3,5-triazin-4-yl; pyridazinyl, in particular pyridazin-3-yl, and pyrazinyl. The pyridine N-oxides and pyridazine N-oxides and the pyridyl, pyrimid-2-yl, pyrimid-4-yl, pyridazinyl and the 1,3,4-triazin-2-yl groups, are a particular group. Unless specified otherwise, the heterocyclo group may be substituted at one or more ring positions with hydroxyl, optionally substituted alkyl, optionally substituted alkenyl, optionally substituted alkoxy, acyl, acyloxy, amino, aryloxy, carboxy, cyano, halogen, mercapto, oxo, nitro, thiol, sulfo, and the salts thereof.

As used herein, "heterocycloalkylene" denotes a chain of 1 to 20 carbon atoms, typically 1 to 12 carbon atoms, 1 to 10 carbon atoms, 1 to 8 carbon atoms, and in some embodiments 1 to 4 carbon atoms containing one or more heterocyclic moieties that can be saturated or unsaturated (but not aromatic). The heterocyclic moiety may be a part of a pendant (or side) group attached to a chain of atoms (e.g.,

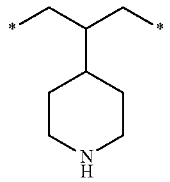 [SMILES: *CC(C*)C1CCNCC1]

wherein * denotes the point of attachment to the remainder of the molecule, or the chain atoms comprise two or more carbon atoms of the heterocyclic moiety (e.g.,).

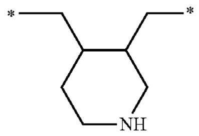 [SMILES: *CC1CNCCC1CC]

Heterocycloalkylene excludes heteroaralkylene.

The terms "hydrocarbon group" and "hydrocarbyl group" as used herein, alone or as part of another group, are used interchangeably and denote organic radicals consisting exclusively of the elements carbon and hydrogen. These moieties include alkyl, alkenyl, and aryl moieties. These moieties also include alkyl, alkenyl, and aryl moieties substituted with other aliphatic or cyclic hydrocarbon groups, such as alkaryl and alkenaryl. Unless otherwise indicated, these moieties preferably comprise a chain of 1 to 25 carbon atoms, 1 to 20 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups will typically have one or more double bonds.

As used herein, alone or as part of another group, “imine” denotes a functional group containing a carbon-nitrogen double bond (C═N).

As used herein, alone or as part of another group, “indole” denotes a functional group containing the structure of

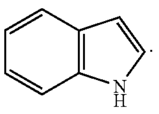

As used herein, alone or as part of another group, “1-naphthyl” denotes a functional group of the formula

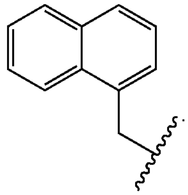 [SMILES: *Cc1cccc2ccccc12]

As used herein, alone or as part of another group, “2-naphthyl” denotes a functional group of the formula

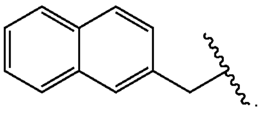 [SMILES: *Cc1ccc2ccccc2c1]

The term “nitro” as used herein, alone or as part of another group, denotes a group of the formula —$NO_2$.

As used herein, the term “Trp with C(4) substitution” shall mean an amino acid residue having the structure

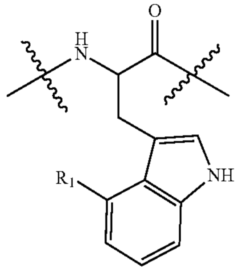

wherein $R_1$ is selected from the group consisting of hydrogen, halo, —CN, —OH, —$NO_2$, —$CONH_2$, —O—$C_{1-6}$ alkyl, $C_{1-6}$ alkyl, $C_{3-6}$ cycloalkyl, $C_{3-6}$ heterocycloalkyl, $C_{6-14}$ aryl, and $C_{6-14}$ heteroaryl, wherein the —O—$C_{1-6}$ alkyl, $C_{1-6}$ alkyl, $C_{3-6}$ cycloalkyl, $C_{3-6}$ heterocycloalkyl, $C_{6-14}$ aryl, or $C_{6-14}$ heteroaryl is optionally substituted; and “” designates the point of attachment of the amino acid residue to the remainder of the composition.

The terms “optional” and “optionally” as used herein means that the subsequently described circumstance may but need not occur, and that the description includes instances where the circumstance occurs and instances in which it does not. For example, “optionally substituted alkyl” means that the alkyl group may or may not be further substituted. By way of further example, “optionally substituted alkoxy” means that the alkyl portion of the alkoxy group may, but need not be present, and the description includes embodiments in which the alkyl portion of the alkoxy group is substituted with one or more hetero atoms such as nitrogen, oxygen, silicon, phosphorous, boron, sulfur, or a halogen atom or by a heterocyclo groups.

As used herein, the term “unsubstituted” means that the specified group bears no substituents.

The term “optionally substituted” or “substituted” means that the referenced group is optionally substituted with one or more additional group(s), such as those individually and independently selected from halogen, —CN, —$NH_2$, —$NO_2$, —$CONH_2$, —O—$C_{1-6}$ alkyl, —NH (alkyl), —N$(alkyl)_2$, —OH, —$CO_2H$, —$CO_2$alkyl, —C(O)$NH_2$, —C(O)NH (alkyl), —C(O) N$(alkyl)_2$, —$S(O)_2NH_2$, —S(O)NH(alkyl), —$S(O)_2$N $(alkyl)_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —$NH_2$, —NH$(CH_3)$, —N$(CH_3)_2$, —$NO_2$, —$CONH_2$, —OH, —$CO_2H$, —$CO_2$($C_1$-$C_4$alkyl), —C(O)$NH_2$, —C(O)NH($C_1$-$C_4$ alkyl), —C(O)N($C_1$-$C_4$ $alkyl)_2$, —$S(O)_2NH_2$, —$S(O)_2$NH($C_1$-$C_4$ alkyl), —$S(O)_2$N($C_1$-$C_4$ $alkyl)_2$, $C_1$-$C_4$ alkyl, $C_3$-$C_6$ cycloalkyl, $C_1$-$C_4$ fluoroalkyl, $C_1$-$C_4$ heteroalkyl, $C_1$-$C_4$ alkoxy, $C_1$-$C_4$ fluoroalkoxy, —S $C_1$-$C_4$ alkyl, —S(O) $C_1$-$C_4$ alkyl, and —$S(O)_2$C $C_1$-$C_4$ alkyl. In some embodiments, optional substituents are independently selected from halogen, —CN, —$NH_2$, —OH, —NH$(CH_3)$, —N$(CH_3)_2$, —NH (cyclopropyl), —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic) includes oxo (═O). When indicating the number of substituents, the term “one or more” means from one substituent to the highest possible number of substitutions, i.e., replacement of one hydrogen up to replacement of all hydrogens by substituents.

As used herein, alone or as part of another group, “phenyl” denotes a functional group of the formula

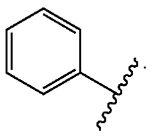 [SMILES: *c1ccccc1]

As used herein, alone or as part of another group, “phenol” denotes a functional group containing the structure of

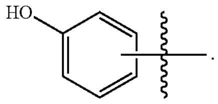

It is understood that the disclosure of a compound herein encompasses all stereoisomers of that compound. As used herein, the term "stereoisomer" refers to a compound made up of the same atoms bonded by the same bonds but having different three-dimensional structures which are not interchangeable. The three-dimensional structures are called configurations. Stereoisomers include enantiomers and diastereomers.

As used herein, the terms "racemate" or "racemic mixture" refer to a mixture of equal parts of enantiomers. The term "chiral center" refers to a carbon atom to which four different groups are attached. The term "enantiomeric enrichment" as used herein refers to the increase in the amount of one enantiomer as compared to the other.

It is appreciated that to the extent compounds of the present disclosure have a chiral center, they may exist in and be isolated in optically active and racemic forms. Some compounds may exhibit polymorphism. It is to be understood that the present disclosure encompasses any racemic, optically-active, diastereomeric, polymorphic, or stereoisomeric form, or mixtures thereof, of a compound of the disclosure, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

The term "polypeptide" includes any polymer of amino acids, or amino acid residues connected together via amide bonds.

The term "polypeptide sequence" refers to a series of amino acid residues which physically comprise a polypeptide.

A "protein" is a macromolecule comprising one or more polypeptides or polypeptide sequences, such as, for example, a naturally occurring or synthetic protein.

A "peptide" is a small polypeptide having a size of 2 to 20 amino acid residues.

As used herein, the term "peptidomimetic" can be defined as a molecule derived from an existing peptide that mimics the biological effect of that peptide. "Peptidomimetic", "peptidomimetic conjugate", "peptidomimetic compound", "peptide analogue", "peptide derivative" and "peptide conjugate" are used interchangeably and refer to a compound that comprises a polymer of two or more amino acids that comprises modifications involving changes to the polymer that do not occur naturally such as, e.g., at least one unnatural amino acid, modified natural amino acid, pseudopeptide bond or chemical moiety that is different from an amino acid, such as a reporter group or a cytotoxic group, including a chelator, a prosthetic group, a linker or a pharmacokinetic modifier. In some embodiments, the peptidomimetics or peptidomimetic conjugate of the present disclosure may comprise a chelator capable of chelating with or complexing with a radionuclide, and/or a linker. In this case, the peptidomimetic or peptidomimetic conjugate has the same meaning of a radiopharmaceutical compound. A peptidomimetic as described herein generally mimics the biological activity of a natural peptide. In some embodiments, the peptidomimetic of the present disclosure mimics the ability, in the sense of having the ability, of natural CCK2R ligands, such as gastrin, to specifically bind to CCK2R.

As used herein, a "binding peptide", "binding peptidomimetic", "binding moiety", or a "conjugate having the binding peptide or binding peptidomimetic that binds to a cellular target of interest" is one that binds to the cellular target with sufficient affinity that is measurably different from a non-specific interaction. Selective binding can be measured, for example, by determining the binding of a molecule compared to binding of a control molecule, which generally is a molecule that does not have specific binding activity.

As used herein, "selective binding" refers to a binding peptide or a binding peptidomimetic or a conjugate comprising the binding peptidomimetic that is capable of binding to a cellular target with sufficient affinity such that the binding peptide or peptidomimetic and/or conjugate is useful as a diagnostic and/or therapeutic agent with respect to the target.

As used herein, the term "radionuclide" and "radioisotope" are used interchangeably and include, but not limited to, alpha emitting radionuclides, beta-emitting radionuclides, and/or gamma-emitting radionuclides, such as, e.g., any one of Y-86, Y-90, Lu-177, Re-186, Re-188, Sr-89, Sm-153, Ac-225, Bi-213, Po-213, Bi-212, Ra-223, Ra-224, Th-227, Tb-149, Ga-67, Ga-68, Cu-61, Cu-64, Cu-67, Zr-89, Cs-137, Pb-203, Pb-212, and Pd-103, among others. For example, lead radionuclides can include any of Pb-196, Pb-197, Pb-198, Pb-199, Pb-200, Pb-201, Pb-202, Pb-203, Pb-209, Pb-210, Pb-211, Pb-212, Pb-213, Pb-214, Pb-215, and Pb-216. Copper radionuclides can include any of Cu-55, Cu-56, Cu-57, Cu-58, Cu-59, Cu-60, Cu-61, Cu-62, Cu-64, Cu-66, Cu-67, Cu-68, Cu-69, Cu-70, Cu-71, Cu-72, Cu-73, Cu-74, Cu-75, Cu-76, Cu-77, Cu-78, Cu-79, Cu-80, Cu-81, Cu-82, Cu-83, and Cu-84. Terbium isotopes can include Tb-161, Tb-155, Tb-152, Tb-149. As used herein, the expressions "XE" and "E-x", where "E" represents the element and "x" represents the particular elemental isotope, are equivalent and have the same meaning. For example, "$^{x}$Pb" and "Pb-x", and "lead-x" are equivalent and have the same meaning, such that "$^{203}$Pb" is equivalent to "Pb-203" and to "lead-203", and "$^{212}$Pb" is equivalent to "Pb-212" and "lead-212". $^{61}$Cu is equivalent to Cu-61 and to Copper-61. $^{64}$Cu is equivalent to Cu-64 and to Copper-64. $^{67}$Cu is equivalent to Cu-67 and to Copper-67.

As used herein, the term "divalent radionuclide" refers to a radionuclide that typically forms ions with a charge of +2 (divalent cations) or sometimes-2 (divalent anions). Some common divalent cations used in radioimaging include, but not limited to, barium (Ba), calcium (Ca), cobalt (Co), copper (Cu), lead (Pb), radium (Ra), and strontium (Sr).

As used herein, lead (Pb) refers to the lead element and includes nuclides of both radioactive and observationally stable. The nuclides of Pb include, but are not limited to, Pb-196, Pb-197, Pb-198, Pb-199, Pb-200, Pb-201, Pb-202, Pb-203, Pb-204, Pb-205, Pb-206, Pb-207, Pb-208, Pb-209, Pb-210, Pb-211, Pb-212, Pb-213, Pb-214, Pb-215, and Pb-216.

As used herein, copper (Cu) refers to the copper element and includes nuclides of both radioactive and observationally stable. The nuclides of Cu include, but are not limited to, Cu-55, Cu-56, Cu-57, Cu-58, Cu-59, Cu-60, Cu-61, Cu-62, Cu-63, Cu-64, Cu-65, Cu-66, Cu-67, Cu-68, Cu-69, Cu-70, Cu-71, Cu-72, Cu-73, Cu-74, Cu-75, Cu-76, Cu-77, Cu-78, Cu-79, Cu-80, Cu-81, Cu-82, Cu-83, and Cu-84.

As used herein, the term "radionuclide suitable for therapeutic use" or "radionuclides suitable for therapeutic use" refers to radionuclides that emit alpha particles (a emitters), beta particles (β emitters), gamma rays, or Auger electrons. These radionuclides include, but are not limited to, $^{47}$Sc, $^{67}$Cu, $^{89}$Sr, $^{90}$Y, $^{131}$I, $^{153}$Sm, $^{149}$Tb, $^{161}$Tb, $^{177}$Lu, $^{186}$Re, $^{188}$Re, $^{211}$At, $^{212}$Pb, $^{212}$Bi, $^{223}$Ra, $^{224}$Ra, $^{225}$Ac, $^{226}$Th, and $^{227}$Th.

As used herein, the term "radionuclide suitable for medical imaging use" or "radionuclides suitable for medical imaging use" refers to radionuclide or radionuclides that emit gamma rays or positrons. These radionuclides include, but are not limited to, $^{18}$F (as $^{18}$F-AlF), $^{43}$Sc, $^{44}$Sc, $^{51}$Mn, $^{61}$Cu, $^{64}$Cu, $^{67}$Ga, $^{68}$Ga, $^{86}$Y, $^{89}$Zr, $^{99m}$Tc, $^{18}$F, $^{76}$B, $^{77}$Br, $^{111}$In, $^{123}$I, $^{124}$I, $^{125}$I, $^{152}$Tb, $^{155}$Tb, $^{212}$Pb and $^{203}$Pb.

As used herein, the term "radiopharmaceutical", "radiopharmaceutical conjugate", and "radiopharmaceutical compound" are used interchangeably and refer to a compound that targets cells or tissues of a subject and can be labeled or chelated with a radionuclide that is suitable for medical imaging use or for therapeutic use, such as for the diagnosis, imaging, or treatment of a disease, including treating cancer (radiotherapeutic), or diagnosing or imaging diseased cells or tissues (a radiodiagnostic).

As used herein, the term "conjugate" refers to a compound having a binding moiety that is linked to a chelator or chelating agent, or cytotoxic molecules(s), or prosthetic group(s), or fluorophore molecules(s), either via direct bond or via a linker. A binding moiety can be a peptide or peptidomimetic that may be capable of selectively binding to CCK2R expressed on the surface of a cell. A chelator is a compound capable of chelating radionuclides, such as $^{203}$Pb and/or $^{212}$Pb. A conjugate can contain one or multiple prosthetic groups. For example, a prosthetic group can be used for labeling $^{18}$F to the binding moiety as described in U.S. Pat. No. 12,427,209 and Dillemuth et al. EJNMMI Radiopharmacy and Chemistry (2025) 10:40, each of which is incorporated by reference in its entirety. A conjugate can also contain one or multiple cytotoxic molecules or cytotoxic drugs. A conjugate can also contain one or multiple fluorophore molecules.

As used herein, the term "linker" refers to a chemical moiety that joins together certain moieties of a peptidomimetic, a radiopharmaceutical compound, or a conjugate, such as a chelator, and a targeting ligand (e.g., a CCK2R targeted peptidomimetic, or a CCK2R targeted biomolecule, including an antibody and antibody fragment). That is, the "linker" may correspond to the moiety "L" described herein, for example in formula (2) or formula (3). Any suitable linker known to those skilled in the art in view of the present disclosure can be used in the invention. The linkers can contain, for example, a substituted or unsubstituted alkyl, a substituted or unsubstituted heteroalkyl moiety, a substituted or unsubstituted aryl or heteroaryl, a polyethylene glycol (PEG) linker, a PEG linker linked to natural or unnatural amino acids, a 4-amino-1-carboxymethyl piperidine linker, a substituted or unsubstituted amino acid, a substituted or unsubstituted peptide linker, a sugar-based linker, or a cleavable linker, such as a disulfide linkage or a protease cleavage site such as valine-citrulline-p-aminobenzyl (PAB). For example, in certain embodiments, the linker can comprise a polyethylene glycol group that has been modified on either end.

As used herein, a "target" may be cholecystokinin receptors including the cholecystokinin-1 receptor (CCK1R) and the cholecystokinin-2 receptor (CCK2R), which may be overexpressed or aberrantly expressed in certain types of cancers, and may also be used as a marker for pro-tumorigenic stroma. In one embodiment, the extent of binding of the binding peptidomimetics and/or conjugate to an unrelated target is less than about 10% of the binding of the binding peptidomimetics and/or conjugate to its target as measured, e.g., by a radioimmunoassay. A "target selective" binding peptidomimetics, as used herein, is one that specifically binds to the target with sufficient specificity and affinity to be useful in targeting a therapeutic, targeting diagnostic, or method of detecting the target in a biological sample or a tissue from a subject. In some embodiments, binding peptidomimetics and/or conjugate, has a dissociation constant (KD) of <1 μM, <100 nM, <10 nM, <1 nM, <0.1 nM, <0.01 nM, or <0.001 nM (e.g., $10^{-6}$ M or less, e.g., from $10^{-6}$ M to $10^{-10}$ M, e.g., from $10^{-8}$ M to $10^{-13}$ M).

As used herein, "pharmaceutically acceptable" means suitable for in vivo use in a subject, and is not necessarily restricted to therapeutic use, but also includes diagnostic use. More generally, with respect to any pharmaceutical composition disclosed herein, non-limiting examples of suitable excipients include any suitable buffers, radioprotectants, salts, antioxidants, chelators or chelating agents, tonicity agents, cryoprotectants, lyoprotectants, suspending agents, emulsifying agents, antimicrobial agents, preservatives, chelating agents, binding agents, surfactants, wetting agents, non-aqueous vehicles such as fixed oils, or polymers for sustained or controlled release. See, for example, Berge et al. 1977. (J. Pharm Sci. 66:1-19), or Remington—The Science and Practice of Pharmacy, 21$^{st}$ edition (Gennaro et al editors. Lippincott Williams & Wilkins Philadelphia), each of which is incorporated by reference in its entirety.

As used herein, the terms "salt" and "solvate" have their usual meaning in chemistry. As such, when the compound is a salt or solvate, it is associated with a suitable counter-ion. It is well known in the art how to prepare salts or to exchange counter-ions. Generally, such salts can be prepared by reacting free acid forms of these compounds with a stoichiometric amount of a suitable base (e.g. without limitation, Na, Ca, Mg, or K hydroxide, carbonate, bicarbonate, or the like), or by reacting free base forms of these compounds with a stoichiometric amount of a suitable acid. Such reactions are generally carried out in water or in an organic solvent, or in a mixture of the two. Counter-ions may be changed, for example, by ion-exchange techniques such as ion-exchange chromatography. All zwitterions, salts, solvates and counter-ions are intended, unless a particular form is specifically indicated. In certain embodiments, the salt or counter-ion may be pharmaceutically acceptable, for administration to a subject.

The term "therapeutically effective amount" as used herein to refer to an amount effective at the dosage and duration necessary to achieve the desired therapeutic result. A therapeutically effective amount of the composition may vary depending on factors such as the individual's condition, age, sex, and weight, and the ability of the protein to elicit the desired response of the individual. A therapeutically effective amount can also be an amount that exceeds any toxic or deleterious effect of the composition that would have a beneficial effect on the treatment.

The term "subject" refers to an animal (e.g. a mammal or a non-mammal animal) The subject may be a human or a non-human primate. The subject may be a laboratory mammal (e.g., mouse, rat, rabbit, hamster and the like). The subject may be an agricultural animal (e.g., equine, ovine, bovine, porcine, camelid and the like) or a domestic animal (e.g., canine, feline and the like). In some embodiments, the subject is a human.

As used herein, the terms "cancer" and "cancerous" refer to or describe the pathological condition in mammals that is typically characterized by unregulated cell growth. A "cancer" comprises one or more cancerous cells. The terms of cancer and tumor are used interchangeably herein. Examples of cancer include, but are not limited to, carcinoma, melanoma, lymphoma, blastoma, sarcoma, and leukemia or lymphoid malignancies. More particular examples of such cancers include squamous cell cancer (e.g., epithelial squamous cell cancer), skin cancer, melanoma, lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer (e.g., pancreatic ductal adenocarcinoma), glioblastoma, cervical cancer, ovarian cancer (e.g., high grade serous ovarian carcinoma), liver cancer (e.g., hepatocellular carcinoma (HCC)), bladder cancer (e.g., urothelial bladder cancer), oral cancer, testicular (germ cell tumor) cancer, desmoid tumor, chordoma, pheochromocytoma, medullary thyroid cancer, gastric cancer, hepatoma, breast cancer, brain cancer (e.g., astrocytoma), colon cancer, rectal cancer, colorectal cancer, rectal adenocarcinoma, endometrial or uterine carcinoma, salivary gland carcinoma, kidney or renal cancer (e.g., renal cell carcinoma, nephroblastoma or Wilms' tumor), prostate cancer, vulval cancer, thyroid cancer (including differentiated), insulinoma, hepatic carcinoma, anal carcinoma, small intestine cancer, penile carcinoma, as well as head and neck cancer. Additional examples of cancer include, without limitation, retinoblastoma, thecomas, arrhenoblastomas, hepatocellular carcinoma, hepatoma, hematologic malignancies including non-Hodgkins lymphoma (NHL), multiple myeloma and acute hematologic malignancies, endometrial or uterine carcinoma, endometriosis, fibrosarcomas, choriocarcinoma, salivary gland carcinoma, vulval cancer, thyroid cancer, multiple myeloma, pancreatic neuroendocrine tumor, adrenocortical carcinoma, follicular lymphoma, esophageal carcinomas, hepatic carcinoma, anal carcinoma, penile carcinoma, nasopharyngeal carcinoma, laryngeal carcinomas, Kaposi's sarcoma, melanoma, skin carcinomas, Schwannoma, oligodendroglioma, neuroblastomas, rhabdomyosarcoma, osteogenic sarcoma, osteosarcoma, leiomyosarcomas, urinary tract carcinomas, anaplastic astrocytoma, basal cell carcinoma (basal cell epithelioma), bile duct cancer, small cell bladder cancer, metastatic breast cancer, metastatic colorectal cancer, epithelial ovarian cancer, fallopian tube cancer, gastric adenocarcinoma, glioblastoma multiforme (GBM), recurrent glioblastoma multiforme (GBM), gliomas, gliosarcoma, head and neck squamous cell carcinoma (HNSCC), recurrent head and neck squamous cell carcinoma, malignant pleural mesothelioma head and neck cancer, Hodgkin lymphoma, metastatic renal cell carcinoma, metastatic renal clear cell carcinoma, squamous non-small cell lung cancer, hepatocellular cholangiocarcinoma, thymoma type b2, gastroesophageal junction adenocarcinoma, signet-ring cell carcinoma, gastrointestinal tumor, squamous carcinoma of the lung, relapsed or refractory small-cell lung cancer, treatment-resistant melanoma, metastatic melanoma, Merkel cell carcinoma, neuroendocrine cancer, large cell neuroendocrine cancer, neuroendocrine tumors (NETS), ovarian carcinoma, papillary carcinoma, peritoneal cancer, neuroendocrine prostate cancer, hormone-refractory prostate cancer, castration-resistant prostate cancer, soft tissue sarcoma, and squamous cell carcinoma.

As used herein, the terms "increase," "enhance," "stimulate," and/or "induce" (and like terms) generally refer to the act of improving or increasing, either directly or indirectly, a concentration, level, function, activity, or behavior relative to the natural, expected, or average, or relative to a control condition.

As used herein, the term "inhibit," "suppress," "decrease," "interfere," and/or "reduce" (and like terms) generally refer to the act of reducing, either directly or indirectly, a concentration, level, function, activity, or behavior relative to the natural, expected, or average, or relative to a control condition.

As used herein, the terms "treat", "treatment", "therapeutic" and the like include ameliorating symptoms, reducing disease progression, improving prognosis and reducing recurrence.

As used herein, the term "imaging" refers to a medical or laboratory experimental procedure that uses a radiopharmaceutical compound chelated with a radionuclide for obtaining an image of a subject, for example, a human or a laboratory animal.

DETAILED DESCRIPTION OF THE DISCLOSURE

Cholecystokinin-2 Receptor (CCK2R)-Targeted Peptidomimetics

Embodiments of the present disclosure provide peptidomimetics that targets CCK2R, the CCK2R-targeted peptidomimetics comprising sequences of amino acid residues that provide for binding to CCK2R target. According to one embodiment, all of the amino acid residues may be L-amino acids. According to another embodiment, all of the amino acid residues may be D-amino acids. According to yet another embodiment, the sequence may comprise a mixture of some L- and some D-amino acids. One or more of the amino acids may also be beta-homo amino acids.

In one embodiment, the peptidomimetic contains a tetrapeptide sequence that is of general formula (1):

$$X_0\text{—}X_1\text{-Asp-}X_2 \quad (1)$$

wherein $X_0$, $X_1$ and $X_2$ are independently natural or unnatural (non-proteinogenic) amino acids, and wherein $X_0$, $X_1$ and $X_2$ are optionally substituted.

In some embodiments, $X_0$ is a hydrophobic amino acid. In some embodiments, $X_0$ is a non-proteinogenic, hydrophobic amino acid with structural similarity to Phe or Trp. Some examples of $X_0$ may include, but not limited to, Phe, Trp, 1-Nal, 2-Nal, (2-Indanyl) glycine (IGL), beta-Homo-Trp (bHTrp), L-1,2,3,4-Tetrahydronorharman-3-carboxylic acid (Tpi), L-1,2,3,4-tetrahydroisoquinoline-3-carboxylic acid (Tic), (3-benzothienyl)-L-alanine (Bta), p-benzoyl-L-phenylalanine (Bpa), 3-(4-Biphenyl)-L-alanine (Bip), L-Phe-(4-(4-pyridinyl)-OH (F-4-Pyr), L-Phe (4-3-pyridinyl-OH (F-3-Pyr), L-m-Tyr (3-Phenoxy)-OH (Y-3-F), Fmoc-7-Aza-L-Tryptophan (7-Aza-Trp), Fmoc-4-aza-L-Tryptophan (4-Aza-Trp), Fmoc-3-(3-pyridyl)-L-alanine (3-Pal).

In some embodiments, $X_0$ is a modified Trp. For example, in one embodiment, $X_0$ may be Trp that is substituted at any permissible position with halo, —CN, —$NO_2$, —$CONH_2$, —O—$C_{1-6}$ alkyl, —OH, $C_{1-6}$ alkyl, $C_{3-6}$ cycloalkyl, $C_{3-6}$ heterocycloalkyl, $C_{6-14}$ aryl, or $C_{6-14}$ heteroaryl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, or $C_{6-14}$ heteroaryl is optionally substituted.

In certain embodiments, $X_0$ is Trp with C(4) substitution wherein the C(4) position is substituted by halo, —CN, —$NO_2$, —$CONH_2$, —O—$C_{1-6}$ alkyl, —OH, $C_{1-6}$ alkyl, $C_{3-6}$ cycloalkyl, $C_{3-6}$ heterocycloalkyl, $C_{6-14}$ aryl, or $C_{6-14}$ heteroaryl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, or $C_{6-14}$ heteroaryl is optionally substituted.

In certain embodiments, $X_0$ is Trp with substitution at position(s) other than C(4) wherein the substitution comprises halo, —CN, —$NO_2$, —$CONH_2$, —O—$C_{1-6}$ alkyl, —OH, $C_{1-6}$ alkyl, $C_{3-6}$ cycloalkyl, $C_{3-6}$ heterocycloalkyl, $C_{6-14}$ aryl, or $C_{6-14}$ heteroaryl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, or $C_{6-14}$ heteroaryl is optionally substituted.

In some embodiments, $X_1$ is a hydrophobic or hydrophilic amino acid. In some embodiments, $X_1$ is an unnatural (non-proteinogenic), hydrophobic or hydrophilic amino acid with structural similarity to Met.

In some embodiments, $X_1$ has the structure of —N(R)—CH(R)—C(=O)—. In some embodiments, R is selected from, but not limited to, hydrogen, halo, —CN, —OH, $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted. For example, in one embodiment, $X_1$ is selected from the group consisting of unsubstituted or substituted Ala, Leu, Val, Ile, and Nle. In certain embodiments, $X_1$ is substituted Nle such as, e.g., N-Me-Nle

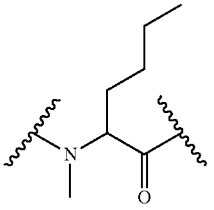 [SMILES: *C(=O)C(CCCC)N(*)C]

N-Me-Nle(6-OH) (),

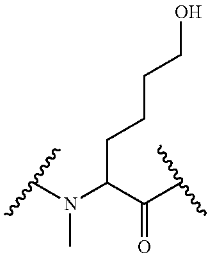 [SMILES: *C(=O)C(CCCCO)N(*)C]

N-Me-Nle (5,5-DiMe) ()

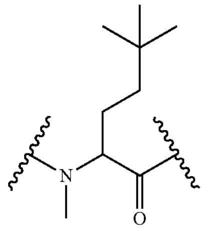 [SMILES: *C(=O)C(CCC(C)(C)C)N(*)C]

N-Me-Nle(6-O-Bz) ()

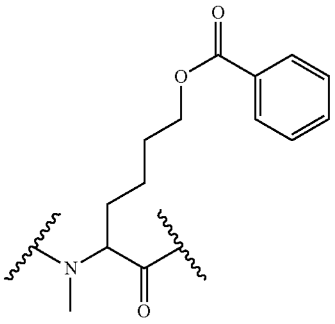 [SMILES: *C(=O)C(CCCCOC(=O)c1ccccc1)N(*)C]

In certain embodiments, $X_1$ is a substituted Ala such as, e.g., N-Me-beta-cyclohexyl-L-alanine (N-Me-Ala (beta-cyclohexyl), or N-Me-Cha) (

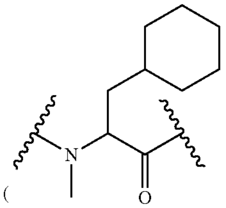

),

N-Me-beta-cyclobutyl Ala (N-Me-Ala (beta-cyclobutyl)) (

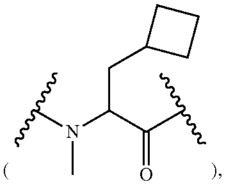 [SMILES: *C(=O)C(CC1CCC1)N(*)C]

), or N-Me-cyclopentyl Ala (N-Me-Ala (cyclopentyl)) (

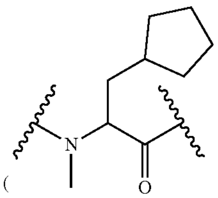

).

In some embodiments, $X_2$ is a hydrophobic or hydrophilic amino acid. In some embodiments, $X_2$ is an unnatural (non-proteinogenic), hydrophobic amino acid with structural similarity to Phe.

In some embodiments, $X_2$ has the structure of —NH—CH(R)—C(=O)—$NH_2$. In some embodiments, R is selected from, but not limited to, hydrogen, halo, —CN, —OH, $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted. For example, in one embodiment, R in $X_2$ is selected from unsubstituted or substituted phenyl, benzyl, 1-adamantyl, 1-naphthyl, 2-naphthyl, 1-anthryl, 2-anthryl, 3-anthryl, phenol, and indole. In certain embodiments, $X_2$ is selected from the group consisting of unsubstituted or substituted Phe-$NH_2$, Trp-$NH_2$, and Nal-$NH_2$. For example, in one embodiment, $X_2$ is 1-Nal-$NH_2$ (

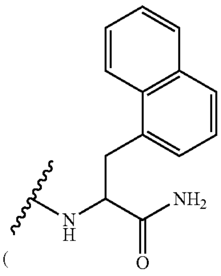

).

In another embodiment, $X_2$ is 2-Nal-$NH_2$ (

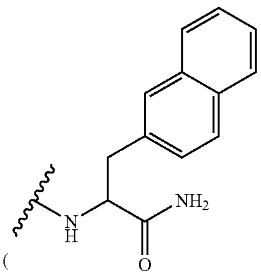

).

In certain embodiments, the peptidomimetic comprises the sequence of formula (1A):

(1A)

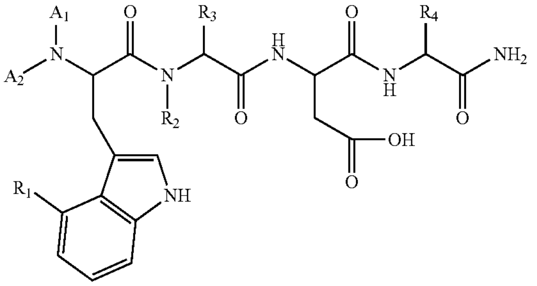

wherein $A_1$ is hydrogen or optionally substituted $C_{1-6}$ alkyl, $A_2$ is hydrogen or a bond connecting the sequence of formula (1A) to the remainder of the peptidomimetic, $R_1$ is selected from the group consisting of hydrogen, halo, —CN, —$NO_2$, —$CONH_2$, —O—$C_{1-6}$ alkyl, —OH, $C_{1-6}$ alkyl, $C_{3-6}$ cycloalkyl, and $C_{3-6}$ heterocycloalkyl, wherein the $C_{1-6}$ alkyl, —O—$C_{1-6}$ alkyl, $C_{3-6}$ cycloalkyl, or $C_{3-6}$ heterocycloalkyl is optionally substituted, $R_2$ is selected from the group consisting of hydrogen, halo, —CN, —OH, and $C_{1-6}$ alkyl, wherein the $C_{1-6}$ alkyl is optionally substituted, $R_3$ is selected from the group consisting of $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted, and $R_4$ is selected from the group consisting of unsubstituted or substituted phenyl, benzyl, 1-adamantyl, 1-naphthyl, 2-naphthyl, 1-anthryl, 2-anthryl, 3-anthryl, phenol, and indole.

In certain embodiments, the peptidomimetic comprises the sequence of formula (1B):

(1B)

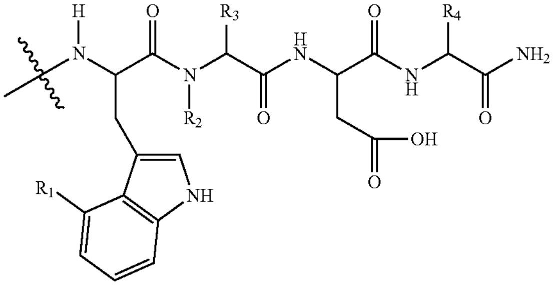

wherein designates the point of attachment of the sequence of formula (1B) to the remainder of the peptidomimetic conjugate, $R_1$ is selected from the group consisting of hydrogen, halo, —CN, —$NO_2$, —$CONH_2$, —O—$C_{1-6}$ alkyl, —OH, $C_{1-6}$ alkyl, $C_{3-6}$ cycloalkyl, and $C_{3-6}$ heterocycloalkyl, wherein the $C_{1-6}$ alkyl, —O—$C_{1-6}$ alkyl, $C_{3-6}$ cycloalkyl, or $C_{3-6}$ heterocycloalkyl is optionally substituted, $R_2$ is selected from the group consisting of hydrogen, halo, —CN, —OH, and $C_{1-6}$ alkyl, wherein the $C_{1-6}$ alkyl is optionally substituted, $R_3$ is selected from the group consisting of $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted, and $R_4$ is selected from the group consisting of unsubstituted or substituted phenyl, benzyl, 1-adamantyl, 1-naphthyl, 2-naphthyl, 1-anthryl, 2-anthryl, 3-anthryl, phenol, and indole.

Some exemplary peptidomimetics are included in Table 2 of the Example section below.

Peptidometic Conjugates

Embodiments of the present disclosure provide a peptidomimetic conjugate that is capable of binding to cholecystokinin-2 receptor (CCK2R) expressed on the surface of cells, for example cancer cells in humans and mice, and when chelated with a radionuclide, it may thereby release radiation energy or cytotoxic drugs to targeted cancer cells and other cells (e.g., tumor stromal cells) in the tumor microenvironment; or when labeled with fluorephore molecule, it can be used for imaging cells or tissues that express CCK2R; or when linked to cytotoxic agents, it can be used for killing cells of cancer or tumor or other diseases; or when linked to prosthetic groups, it can be used for labeling of radionuclides. In accordance with aspects of the present disclosure, the peptidomimetic conjugate comprises a chelator (Z) that is connected to a CCK2R targeted peptidomimetics or derivative thereof ($X_0$—$X_1$-Asp-$X_2$) optionally through a linker (L), forming a conjugate of general formula (Z-L-$X_0$—$X_1$-Asp-$X_2$), which can thereby bind to CCK2R and release radiation energy or cytotoxic drug at the tumor site.

Accordingly, one embodiment of the present disclosure provides a peptidomimetic conjugate targeting cholecystokinin 2 receptor (CCK2R), the peptidomimetic conjugate is of general formula (2):

Z-L-$X_0$—$X_1$-Asp-$X_2$ (2)

wherein

- Z is a chelator capable of chelating a radionuclide, one or multiple cytotoxic agents, one or multiple prosthetic groups, or one or multiple fluorophore molecules,
- L is a linker, or absent,
- $X_0$ is Trp, or Trp with substitution, wherein the substitution is preferably at C(4) position, and
- $X_1$ and $X_2$ are independently natural or unnatural (non-proteinogenic) amino acids.

In some embodiments, Z is any chelator described herein, and L is any linker described herein.

In some embodiments, $X_0$ is Trp without C(4) modification. In some embodiments, $X_0$ is Trp with C(4) substitution wherein the C(4) position is substituted by halo, —CN, —$NO_2$, —$CONH_2$, —O—$C_{1-6}$ alkyl, —OH, $C_{1-6}$ alkyl, $C_{3-6}$ cycloalkyl, $C_{3-6}$ heterocycloalkyl, $C_{6-14}$ aryl, or $C_{6-14}$ heteroaryl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, or $C_{6-14}$ heteroaryl is optionally substituted.

In some embodiments, $X_1$ has the structure of —N(R)—CH(R)—C(=O)—, and $X_2$ has the structure of —NH—CH(R)—C(=O)—$NH_2$. In some embodiments, R is selected from, but is not limited to, hydrogen, halo, —CN, —OH, $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted. For example, in one embodiment, R in $X_2$ is selected from unsubstituted or substituted phenyl, benzyl, 1-adamantyl, 1-naphthyl, 2-naphthyl, 1-anthryl, 2-anthryl, 3-anthryl, phenol, and indole. For example, in one embodiment, $X_1$ is selected from the group consisting of unsubstituted or substituted Ala, Leu, Ile, and Nle. In another embodiment, $X_2$ is selected from the group consisting of unsubstituted or substituted Phe-$NH_2$, Trp-$NH_2$, and Nal-$NH_2$.

According to one embodiment, the present disclosure provides a peptidomimetic conjugate that is of formula (3):

(3)

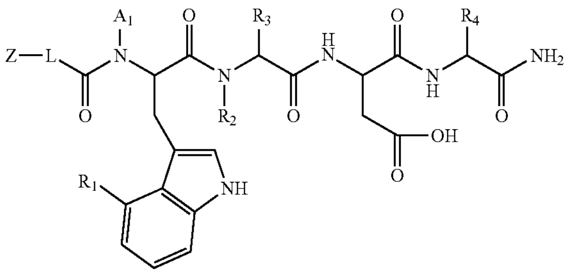

wherein

- $A_1$ is hydrogen or optionally substituted $C_{1-6}$ alkyl,
- L is a linker, or absent,
- $R_1$ is selected from the group consisting of hydrogen, halo, —CN, —$NO_2$, —$CONH_2$, —OH, —O—$C_{1-6}$ alkyl, $C_{1-6}$ alkyl, $C_{3-6}$ cycloalkyl, and $C_{3-6}$ heterocycloalkyl, wherein the $C_{1-6}$ alkyl, —O—$C_{1-6}$ alkyl, $C_{3-6}$ cycloalkyl, or $C_{3-6}$ heterocycloalkyl is optionally substituted,
- $R_2$ is selected from the group consisting of hydrogen, halo, —CN, —OH, and $C_{1-6}$ alkyl, wherein the $C_{1-6}$ alkyl is optionally substituted,
- $R_3$ is selected from the group consisting of $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted,
- $R_4$ is selected from the group consisting of unsubstituted or substituted phenyl, pyridine, benzyl, 1-adamantyl, 1-naphthyl, 2-naphthyl, 1-anthryl, 2-anthryl, 3-anthryl, phenol, and indole, and
- Z is a chelator capable of chelating a radionuclide, one or multiple cytotoxic agents, one or multiple prosthetic groups, or one or multiple fluorophore molecules.

According to another embodiment of the present disclosure, the peptidomimetic conjugate has the structure of formula (4):

(4)

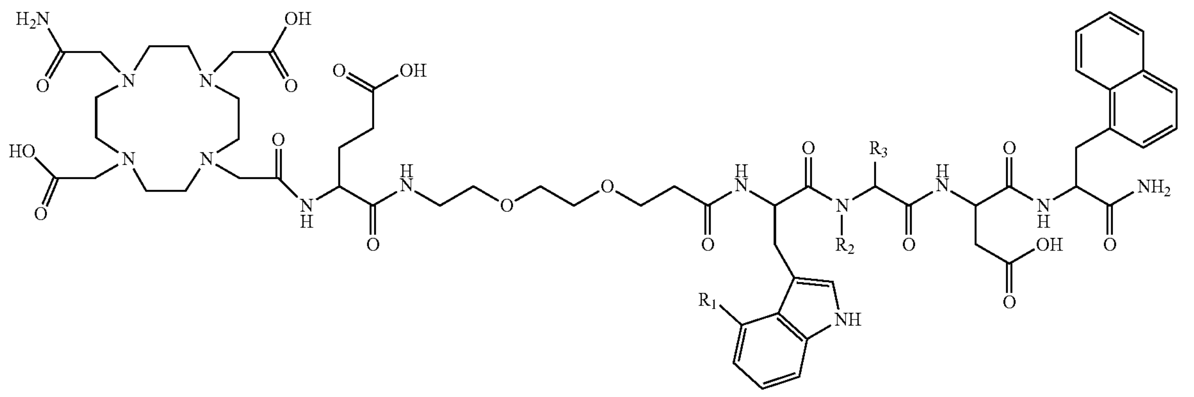

wherein $R_1$ is selected from the group consisting of $C_{1-6}$ alkyl, cyano, —$NO_2$, —$CONH_2$, —OH, halo, —O—$C_{1-6}$ alkyl, $C_{1-6}$ alkyl, and hydroxy, $R_2$ is hydrogen, or substituted or unsubstituted $C_{1-6}$ alkyl, and $R_3$ is selected from the group consisting of $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted.

For example, in some embodiments, $R_1$ is selected from the group consisting of cyano, halo, and hydroxyl. In some embodiments, $R_1$ is selected from the group consisting of cyano and halo. In some embodiments, $R_3$ is selected from the group consisting of butyl, isobutyl, sec-butyl, pentyl, cyclopentyl, and methyl-cyclopentyl. In some embodiments, $R_2$ is methyl.

Chelators

In certain embodiments, the chelator (or chelating agent) comprised by a CCK2R targeted peptidomimetic or a CCK2R targeted peptidomimetic conjugate of the present disclosure may be used for radiolabeling (be chelated with or complexed with) the peptidomimetic or peptidomimetic conjugate with a radionuclide, which can be used for any of imaging, diagnostics, or therapeutic purposes. For example, the chelator may be radiolabeled or complexed with a radionuclide that is used for medical imaging, diagnosis and/or therapy of cancer or tumor, such as those malignancies having CCK2R expression.

In the context of the present disclosure, suitable chelators include, but are not limited to, DOTA (1,4,7,10-tetraazacyclododecane-1,4,7,10-tetraacetic acid), DOTA-NHS-ester, p-SCN-Bn-DOTA (C-DOTA), DOTAGA (2-[1,4,7,10-tetraazacyclododecane]-pentanedioic acid), DOTAGA-anhydride, DO2A (4,11-bis(carboxymethyl)-1,4,8,11-tetraazabicyclo[6.6.2]hexadecan), CB-DO2A (4,10-bis (carboxymethyl)-1,4,7,10-tetraazabicyclo[5.5.2] tetradecane), DPDP (N,N'-dipyridoxylethylendiamine-N,N'-diacetate-5,5'-bis(phosphat)), ITC-MX (1-p-Isothiocyanatobenzyl-methyl-diethylenetriaminepentaacetic acid), TCMC (1,4,7,10-tetrakis (carbamoylmethyl)-1,4,7,10-tetraazacyclododecane), p-SCN-Bn-TCMC (S-2-(4-Isothiocyanatobenzyl)-1,4,7,10-tetraaza-1,4,7,10-tetra(2-carbamoylmethyl)cyclododecane), 3p-C-DEPA (2-[(carboxymethyl)]-[5-(4-nitrophenyl-1-[4,7,10-tris-(carboxymethyl)-1,4,7,10-tetraazacyclododecan-1-yl]pentan-2-yl)-amino]acetic acid), 3p-C-DEPA-NCS (2,2',2''-(10-(2-(bis(carboxymethyl) amino)-5-(4-isothiocyanatophenyl)pentyl)-1,4,7,10-tetraazacyclododecane-1,4,7-triyl)triacetic acid), p-$NH_2$-Bn-Oxo-DO3A (1-Oxa-4,7,10-tetraazacyclododecane-5-S-(4-aminobenzyl)-4,7,10-triacetic acid), TETA (1,4,8,11-tetraazacyclotetradecane 1,4,8,11-tetraacetic acid), BAT (bis-amino-bis-thiol), p-$NH_2$-Bn-TE3A (2-(4-aminobenzyl)-1,4,7,10-tetraazacyclododecane-1,4,7-triacetic acid), CDTA (cyclohexyl-1,2-diaminetetraacetic acid), CPTA (4-(1,4,8,11-tetraazacyclotetradec-1-yl)-methylbenzoic acid), C-TETA, CB-TE2A (4,11-bis-(carboxymethyl)-1,4,8,11-tetraazabicyclo[6.6.2]-hexadecane), CB-TE1A1P (1,4,8,11-tetraazabicyclohexadecane-4-acetic acid-11-methanephosphonic acid), CB-TE2P (1,4,8,11-tetraazacyclotetradecane-1,8-di(methanephosphonic acid)), MM-TE2A, DM-TE2A, TE2A (4,11-bis(carboxymethyl)-1,4,8,11-tetraaza-bicyclo [6.6.2]hexadecane), TMT (terpyridine-bis(methyleneamine) tetraacetic acid), TRITA (1,4,7,10-tetraazacyclotridecan-N, N',N'',N'''-tetraacetic acid), TTHA (triethylenetetraamine-hexaacetic acid), Diamsar (1,8-Diamino-3,6,10,13,16,19-hexaazabicyclo[6,6,6]-eicosane), SarAr (1-N-(4-Aminobenzyl)-3,6,10,13,16,19-hexaazabicyclo[6.6.6]-eicosane-1,8-diamine), AmBaSar, BaBaSar, NOTA (1,4,7-triazacyclononane-1,4,7-triacetic acid), p-SCN-Bn-NOTA (2-S-(4-Isothiocyanatobenzyl)-1,4,7-triazacyclononane-1,4,7-triacetic acid), NODA (1,4,7-triazacyclononane-1,4-diacetic acid), NODASA (1,4,7-triazacyclononan-1-succinic acid-4,7-diacetic acid), NODAGA (1-(1-carboxy-3-carboxypropyl)-4,7-(carboxy)-1,4,7-triazacyclononane), NETA ({4-[2-(bis-carboxymethylamino)-ethyl]-7-carboxymethyl-[1,4,7]triazonan-1-yl}-acetic acid), NETA-monoamide, C-NE3TA-NCS (7-[2-({carboxymethyl}[{4-isothiocyanatophenyl}methyl]amino)ethyl]-1,4,7-triazacyclononane-1,4-diacetic acid), C-NETA-NCS (4-isothiocyanatobenzyl-1-oxa-4,7,10-triazacyclododecane-N,N',N''-triacetic acid), 3p-C-NETA (4-[2-(bis-carboxymethylamino)-5-(4-nitrophenyl)-entyl])-7-carboxymethyl-triazonan-1-yl acetic acid), TACN-TM (N,N',N"-tris (2-mercaptoethyl)-1,4,7-triazacyclononane), DTPA (diethylenetriaminepentaacetic acid), p-SCN-Bn-DTPA (),

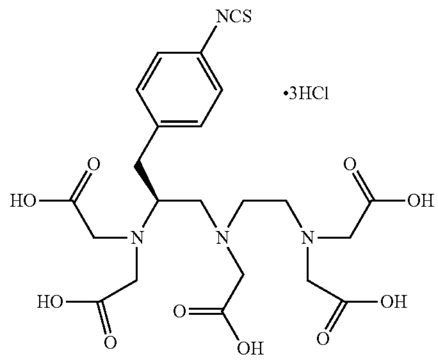

p-SCN-Bn-1B-DTPA, p-SCN-Bn-1B4M-DTPA, CHX-A"-DTPA (2-(p-isothiocyanatobenzyl)-cyclohexyldiethylenetriaminepentaacetic acid), p-SCN-Bn-CHX-A"-DTPA ([(R)-2-Amino-3-(4-isothiocyanatophenyl) propyl]-trans-(S,S)-cyclohexane-1,2-diamine-pentaacetic acid), BAPTA (1,2-bis (o-aminophenoxy) ethane-N,N,N',N'-tetraacetic acid)), TRAP (1,4,7-triazacyclononane 1,4,7-tris[methyl (2-carboxyethyl)phosphinic acid]), AAZTA (1,4-bis(hydroxycarbonyl methyl)-6-[bis(hydroxylcarbonyl methyl)] amino-6-methylperhydro-1,4-diazepine), NOPO (3-(((4,7-bis ((hydroxy(hydroxymethyl)phosphoryl)methyl)-1,4,7-triazonan-1-yl)methyl)(hydroxy)phosphoryl)propanoic acid), $H_2$dedpa (1,2-[[6-(carboxy)-pyridin-2-yl]-methylamino]ethane), $H_4$octapa (N,N'-bis(6-carboxy-2-pyridylmethyl)-ethylenediamine-N,N'-diacetic acid), $H_2$azapa (N,N'-[1-benzyl-1,2,3-triazole-4-yl]methyl-N,N'-[6-(carboxy) pyridin-2-yl]-1,2-diaminoethane), $H_5$decapa (N,N"-[[6-(carboxy)pyridin-2-yl]methyl]-diethylenetriamine-N,N',N"-triacetic acid), p-SCN-Bn-$H_4$octapa ()

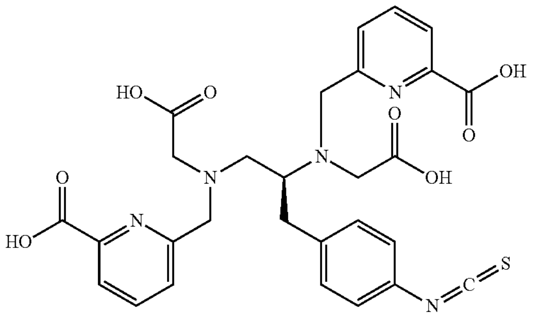 [SMILES: O=C(O)CN(Cc1cccc(C(=O)O)n1)C[C@H](Cc1ccc(N=C=S)cc1)N(CC(=O)O)Cc1cccc(C(=O)O)n1]

EDTA (ethylenediamine-N,N'-tetraacetic acid), EGTA (ethyleneglykol-O,O-bis(2-aminoethyl)-N,N,N',N'-tetraacetic acid), HBED (N,N'-bis(2-hydroxybenzyl)-ethylenediamine-N,N'-diacetic acid), HBED-CC (N,N'-bis[2-hydroxy-5-(carboxyethyl)benzyl]ethylenediamine-N,N'-diacetic acid), (HBED-CC) TFP, HEDTA (hydroxyethyldiaminetriacetic acid), HP-DOA3 (1-(p-nitrobenzyl)-1,4,7,10-tetraazacyclodecan-4,7,10-triacetate), 6-hydrazinyl-N-methylpyridine-3-carboxamide, $H_2$macropa (N,N'-bis[(6-carboxy-2-pyridin) methyl]-4,13-diaza-18-crown-6), $H_2$macropa-NCS, $H_2BZ_2$macropa, $H_2BZ_2$macropa, $H_2$BZmacropa-NCS, THP (4-amino-4-{2-[(3-hydroxy-1,6-dimethyl-4-oxo-1,4-dihydro-pyridin-2-ylmethyl)-carbamoyl]-ethyl} heptanedioic acid bis-[(3-hydroxy-1,6-dimethyl-4-oxo-1,4-dihydro-pyridin-2-ylmethyl)-amide]), SHBED (N,N'-bis(2-hydroxy-5-sulfobenzyl)-ethylenediamine-N,N'-diacetic acid), CP256 (4-acetylamino-4-[2-[(3-hydroxy-1,6-dimethyl-4-oxo-1,4-dihydro-pyridin-2-ylmethyl)-carbamoyl]-ethyl]-heptanedioic acid bis-[(3-hydroxy-1,6-dimethyl-4-oxo-1,4-dihydro-pyridin-2-ylmethyl)-amide]), 2,3-EIOPO (3-hydroxypyridin-2-one), PCTA (3,6,9,15-tetraazabicyclo [9.3.1]-pentadeca-1 (15), 11,13-triene-3,6,9-triacetic acid), p-SCN-Bn-PCTA (3,6,9,15-Tetraazabicyclo[9.3.1]pentadeca-1 (15), 11,13-triene-4-S-(4-isothiocyanatobenzyl)-3,6, 9-triacetic acid), OCTAPA (N,NO-bis(6-carboxy-2-pyridylmethyl)-ethylenediamine-N,NO-diacetic acid), DATA ((6-pentanoic acid)-6-(amino)methy-1,4-diazepinetriacetate), DFO (N'-[5-[acetyl(hydroxy)aminopentyl]-N-[5-[[4-[5-aminopentyl-(hydroxy)amino]-4-oxobutanoyl]amino]pentyl]-N-hydroxybutandiamide), p-SCN-Bn-DFO (1-(4-isothiocyanatophenyl)-3-[6, 17-dihydroxy-7,10,18,21-tetraoxo-27-(N-acetylhydroxylamino)-6,11,17, 22-tetraazaheptaeicosine] thiourea), $H_6$phospha (N,N'-(methylenephosphonate)-N,N'-[6-(methoxycarbonyl)pyridin-2-yl]-methyl-1,2-diaminoethane), HEHA (1,4,7,10,13, 16-hexaazacyclohexadecane-N,N',N",N"',N"",N""'-hexaacetic acid), p-SCN-Bn-HEHA (2-(4-Isothicyanatobenzyl)-1,2,7,10,13-hexaazacyclooctadecane-1,4,7,10,13,16-hexaacetic acid), PEPA (1,4,7,10,13-pentaazacyclopentadecane-N,N',N",N"', N""-pentaacetic acid), p-SCN-Bn-PEPA (2-[Bis(carboxymethyl)amino] ethyl-[2-[Bis(carboxymethyl)amino]-3-(4-isothiocyanatophenyl)propyl]amino]acetic acid), crown (2,2',2",2"'-(1,10-dioxa-4,7,13,16-tetraazacyclooctadecane-4,7,13,16-tetrayl) tetraacetic acid), MACROPA (4-amino-6-[[6-[(6-carboxypyridin-2-yl)methyl]-1,4,10,13-tetraoxa-7,16-diazacyclooctadec-7-yl]methyl]pyridine-2-carboxylic acid), MACROPA-NCS, pypa, py4pa (6,6'-(((azanediylbis(ethane-2,1-diyl))bis((carboxymethyl)azanediyl))bis(methylene)) dipicolinic acid), noneunpa (6,6'-(((oxybis(ethane-2,1-diyl)) bis((carboxymethyl)azanediyl))bis(methylene))dipicolinic acid), DOTAM (2,2',2",2"'-(1,4,7,10-tetraazacyclododecane-1,4,7,10-tetrayl)tetraacetamide), DO3AM (2-(4,7,10-tris(2-amino-2-oxoethyl)-1,4,7,10-tetraazacyclododecan-1-yl)acetic acid), DOTPI (1,4,7,10-tetraazacyclododecane-1, 4,7,10-tetrakis[methylene(2-carboxyethylphosphinic acid)]), S-2-(4-isothiocyanatobenzyl)-1,4,7,10-tetraazacyclododecane tetraacetic acid, $mas_3$ (mercaptoacetyl-triserine), and derivatives thereof. Further chelators include, but not limited to, diamidedithiols ($N_2S_2$), triamidethiols ($N_3S$), tetraamines ($N_4$), hydrazinonicotinic acid (HYNIC), ethylendiamine-N,N'-diacetic acid (EDDA), tricine, desferrioxamine, deferiprone, and derivatives thereof.

In certain embodiments, the chelator that may be used in the invention disclosed herein includes, but is not limited to,

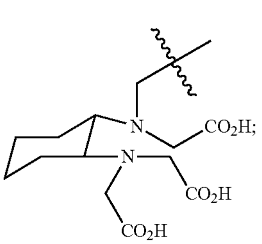

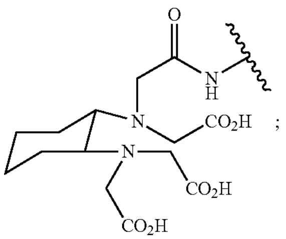

-continued
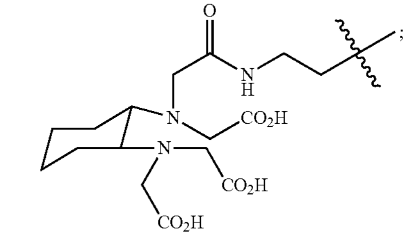
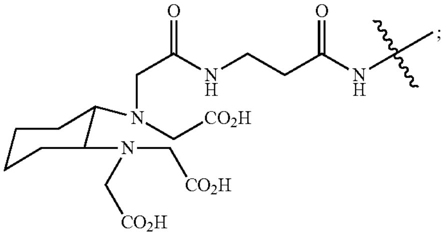
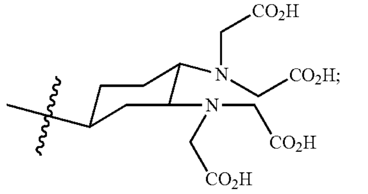
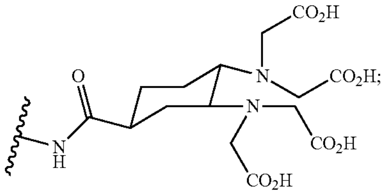
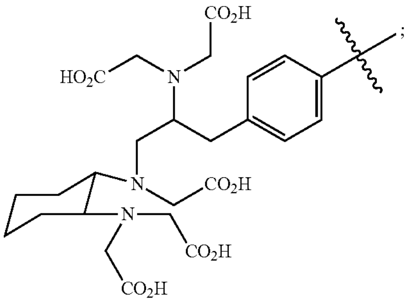
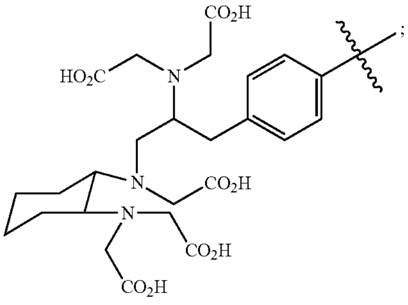
-continued
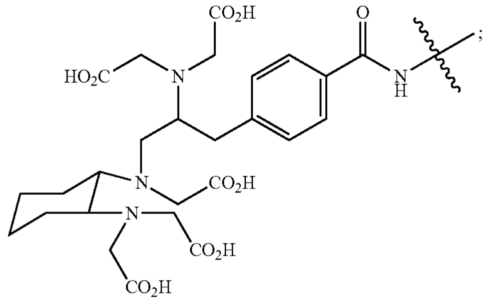
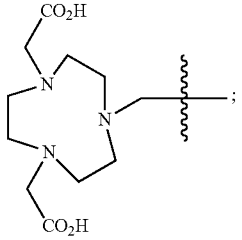
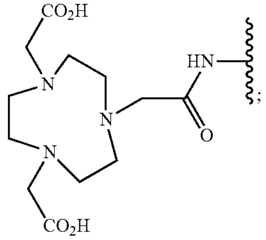
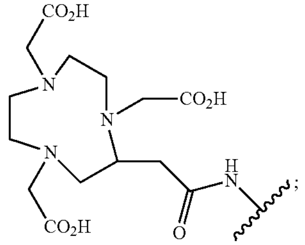
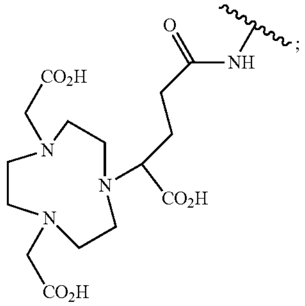
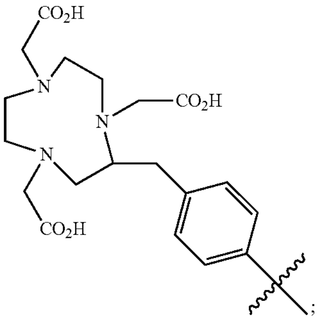

-continued
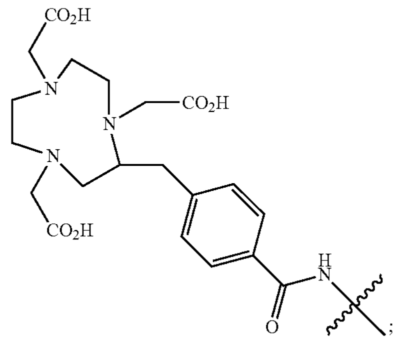
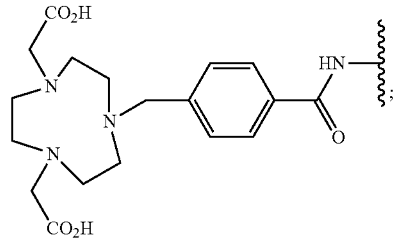
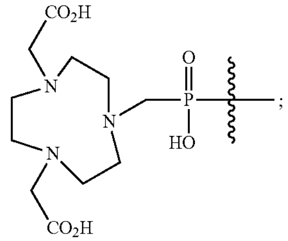
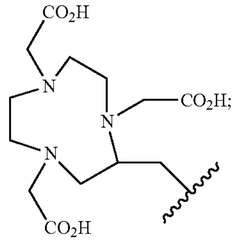
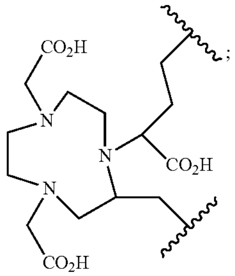
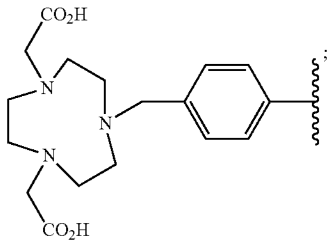
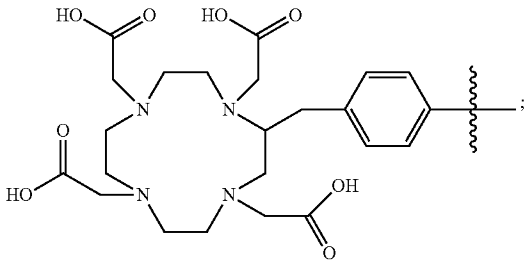
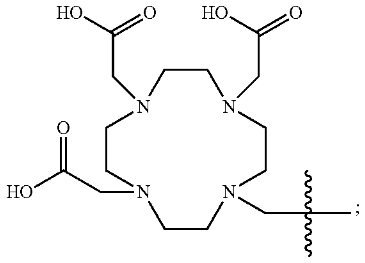
-continued
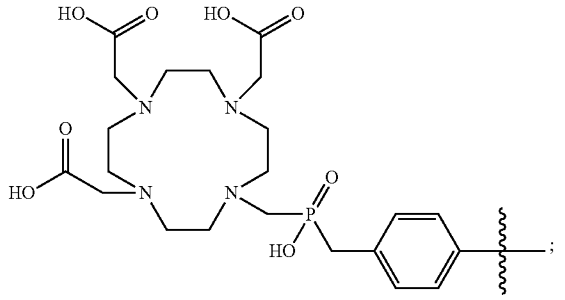
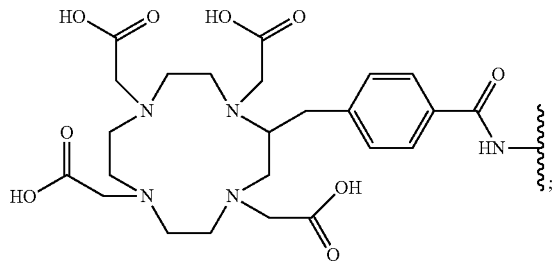
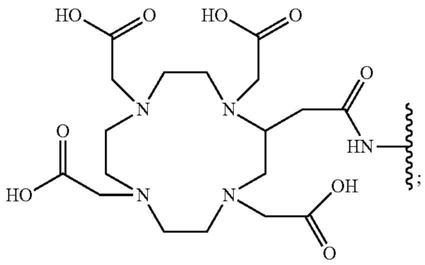
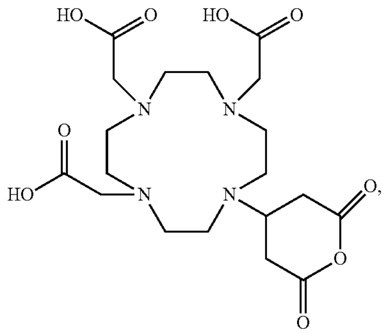
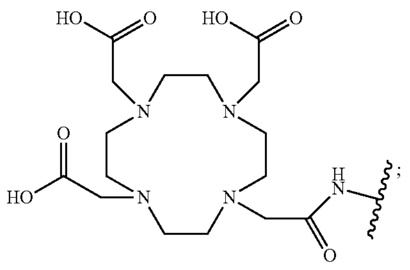

-continued
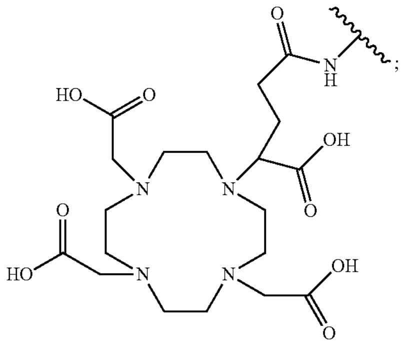
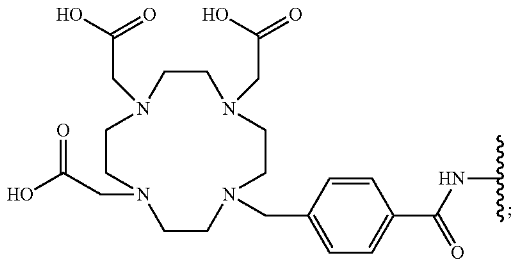
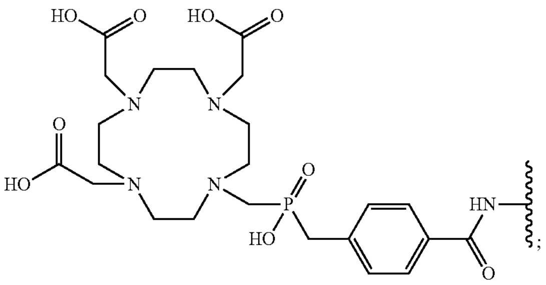
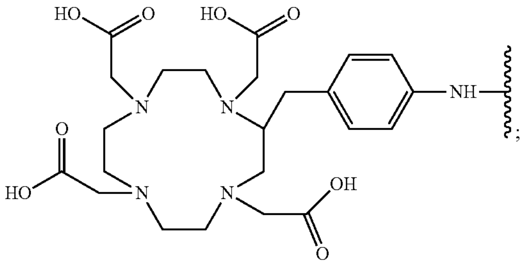
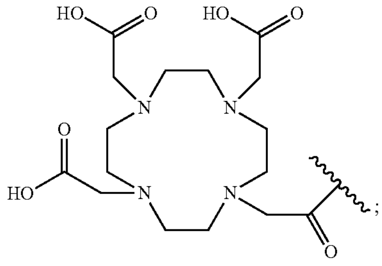
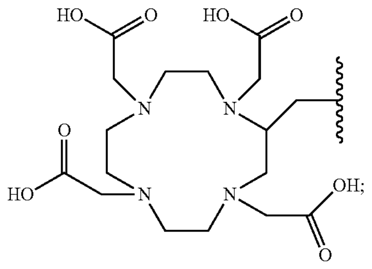
-continued
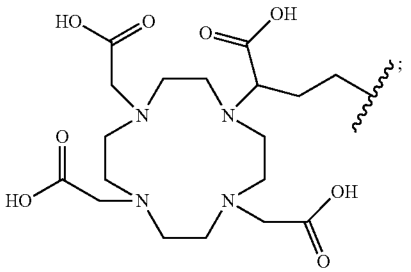
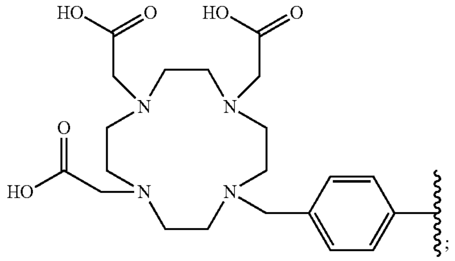
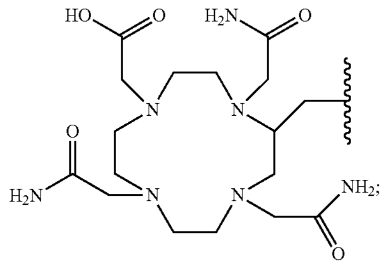
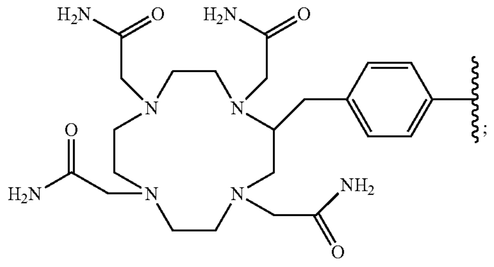
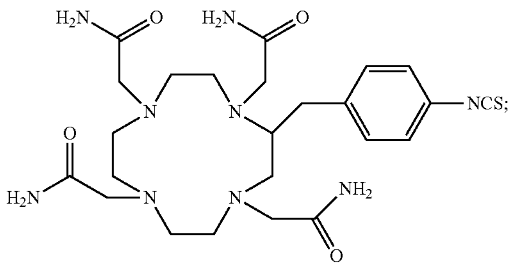
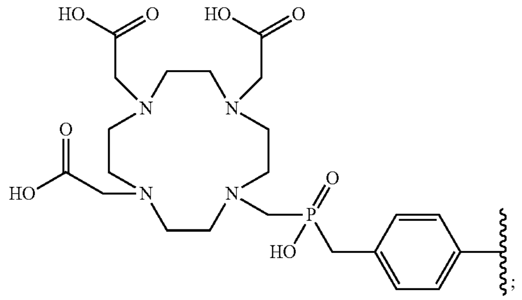

-continued
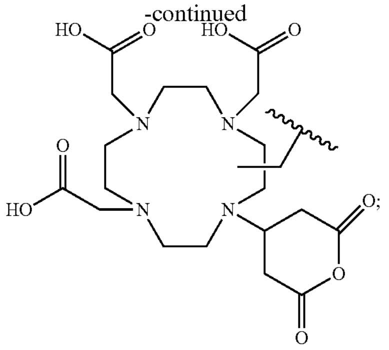
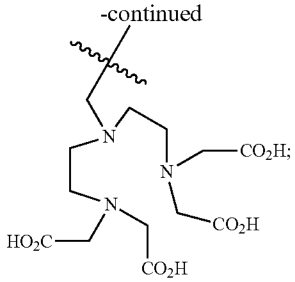
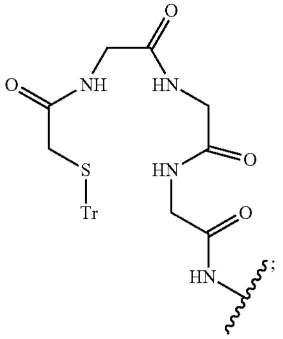
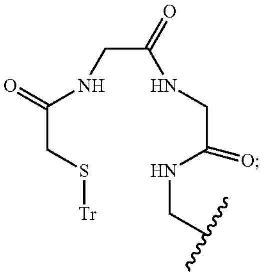
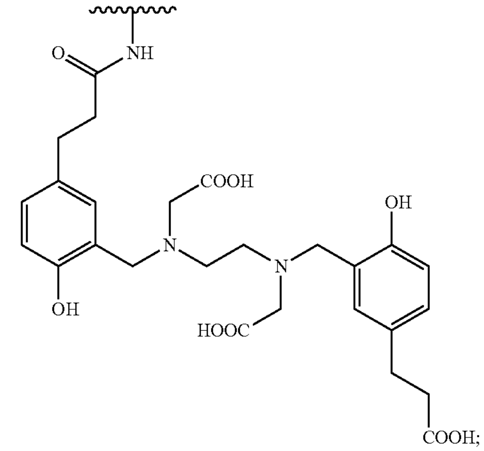
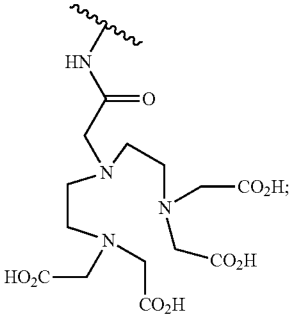
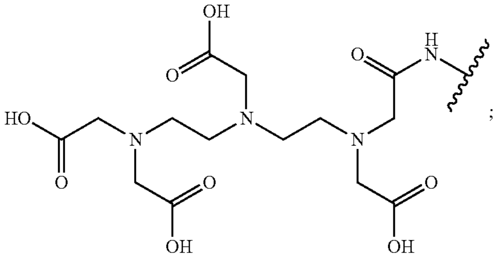
;
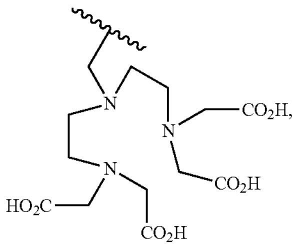
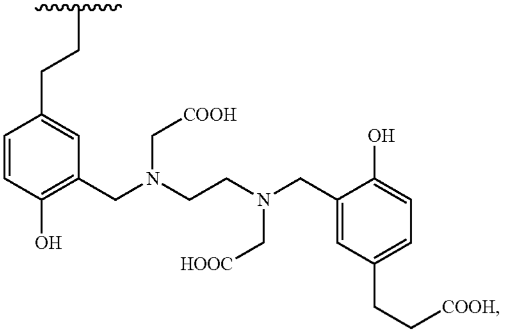
and -continued

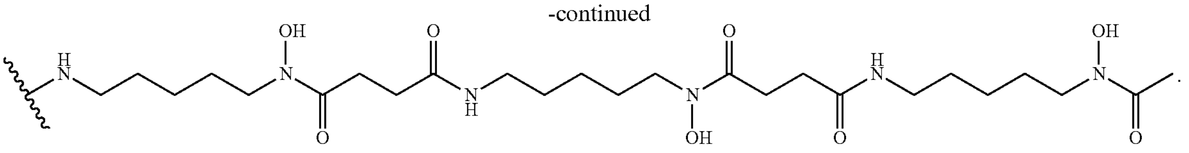

In some embodiments, the chelator that may be used in the invention disclosed herein can comprise the following structure:

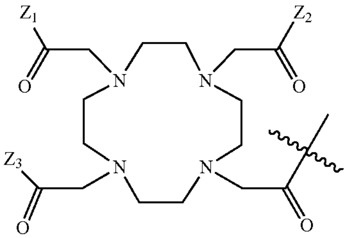

wherein $Z_1$, $Z_2$ and $Z_3$ are independently —$NH_2$ or —OH. For example, in one such embodiment, the chelator comprises

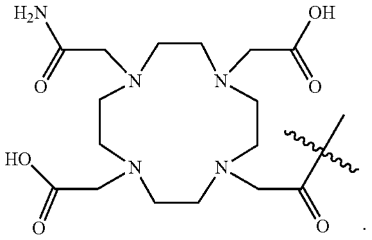 [SMILES: *C(=O)CN1CCN(CC(=O)O)CCN(CC(N)=O)CCN(CC(=O)O)CC1]

In another embodiment, the chelator comprises

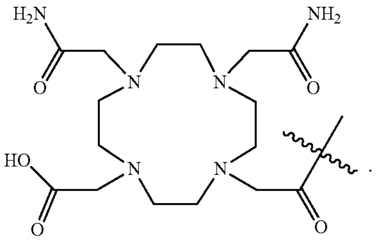

In yet another embodiment, the chelator comprises

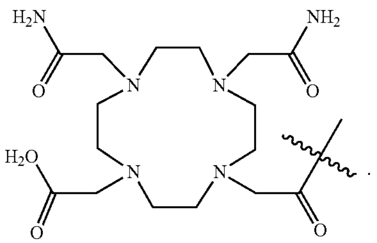 [SMILES: *C(=O)CN1CCN(CC(N)=O)CCN(CC(N)=O)CCN(CC(=O)O)CC1]

In still another embodiment, the chelator comprises

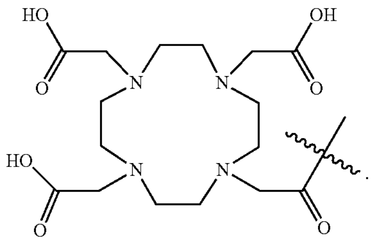 [SMILES: *C(=O)CN1CCN(CC(=O)O)CCN(CC(=O)O)CCN(CC(=O)O)CC1]

In certain embodiments, the chelator that may be used in the invention disclosed herein includes derivatives of 1,4,7,10-tetraazacyclododecan such as, e.g., DOTA ( 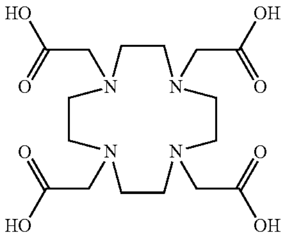 ), ( 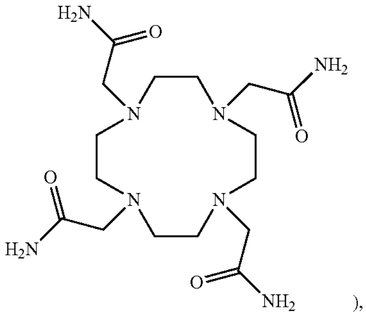 ),

DOTAM ( 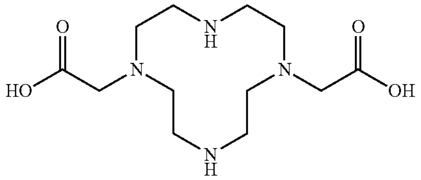 ),

DO2A

-continued ( 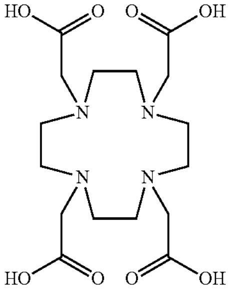 ),

DOTAGA ( 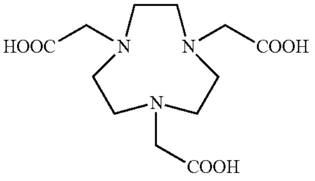 ),

NOTA ( 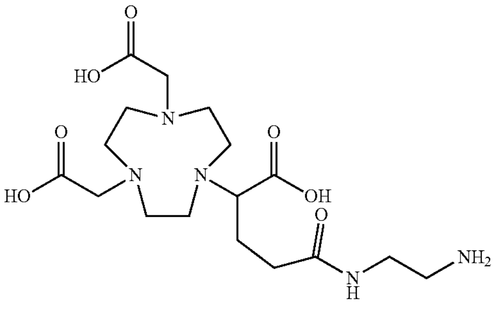 ), and

NODAGA ( 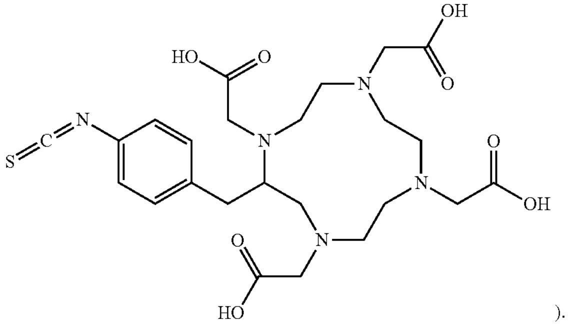 ).

p-SCN-Bn-DOTA

Illustrative chelators include, but are not limited to, those described in, for example, U.S. Pat. Nos. 10,874,753 and 12,049,518; US 2022/0339304; US2022/0401592; WO 2023/191839, US 2023/0348553, WO2024/061483, US2024/0091390, FWO2023/173174, and WO 2023/201435, the contents of which are expressly incorporated herein.

Although a person skilled in the art would use any chelators in the peptidomimetic conjugate comprising the CCK2R targeted peptidomimetic disclosed in the present invention, a preferred chelator of the present disclosure is a Pb-specific chelator (PSC) comprising

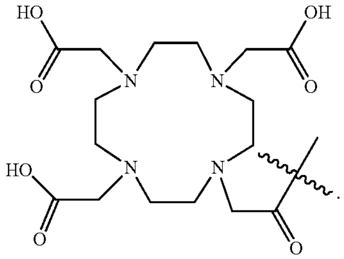 [SMILES: *C(=O)CN1CCN(CC(=O)O)CCN(CC(=O)O)CCN(CC(=O)O)CC1].

Cytotoxic Agent

Cytotoxic agents (or cytotoxic molecules) can be linked to the CCK2R targeted peptidomimetics disclosed herein directly or through linkers, and form peptidomimetic conjugates. The cytotoxic agents that can be used in peptidomimetic conjugates disclosed herein may be auristatins, maytansinoids, tubulysins, calicheamicins, duocarmycins, pyrrolobenzodiazepines, TLR agonists, STING agonists, or topoisomerase inhibitors. Non-limiting examples of cytotoxic agents that can be used in the peptidomimetic conjugates disclosed herein include, but are not limited to, monomethyl auristatin E, monomethyl auristatin F, mertansine, ravtansine, tubulysin A, calicheamicin-gamma1, duocarmycin, PBD, TLR7/8, diABZI STING agonist-2, and exatecan.

Prosthetic Group

According to certain embodiments, a prosthetic group can be conjugated or linked to the peptidomimetic disclosed herein. A prosthetic group can be used for radiolabeling a biomolecule, such as a peptide, a peptidomimetic, a protein, or an antibody. Radionuclides that can be labeled using a prosthetic group include, but are not limited to, $^{18}$F. Non-limiting examples of prosthetic groups that can be used in the peptidomimetic conjugates disclosed herein include 6-[$^{18}$F]fluoronicotinic acid, 4-[$^{18}$F]fluorobenzoic acid, and $BF_3$. For example, Dillemuth et al. describe a rapid cleavage of 6-[$^{18}$F]fluoronicotinic acid prosthetic group that can be used for radiolabeling biomolecules (Dillemuth et al. EJNMMI Radiopharmacy And Chemistry, (2025) 10:40). U.S. Pat. No. 12,427,209 describes $BF_3$ for radiolabeling of $^{18}$F to biomolecules. Each of these is incorporated by reference in its entirety.

Radionuclides

According to certain embodiments, the peptidomimetic conjugate described herein comprises a chelator that is complexed (chelated) with a radionuclide, and which may be a radionuclide that provides a therapeutic effect, and/or that is useful for imaging and/or diagnosis. In some embodiments, the radionuclide comprises an alpha particle-emitting radionuclide. In other embodiments, the radionuclide comprises a beta particle emitting radionuclide. In other embodiments, the radionuclide comprises a gamma ray emitting radionuclide. In some embodiments, the radionuclide comprises a positron-emitting radionuclide. In some embodiments, the radionuclide is divalent.

In some embodiments, the radionuclide is selected from the group consisting of $^{212}$Pb, $^{67}$Cu, $^{64}$Cu, $^{89}$Zr, $^{90}$Y, $^{109}$Pd, $^{111}$Ag, $^{149}$Pm, $^{153}$Sm, $^{166}$Ho, $^{99m}$Tc, $^{67}$Ga, $^{68}$Ga, $^{111}$In, $^{90}$Y, $^{177}$Lu, $^{186}$Re, $^{188}$Re, $^{197}$Au, $^{198}$Au, $^{199}$Au, $^{105}$Rh, $^{165}$Ho, $^{161}$Tb, $^{149}$Pm, $^{44}$Sc, $^{47}$Sc, $^{70}$As, $^{71}$As, $^{72}$As, $^{73}$As, $^{74}$As, $^{76}$As, $^{77}$As, $^{212}$Pb, $^{212}$Bi, $^{213}$Bi, $^{225}$Ac, $^{117m}$Sn, $^{67}$Ga, $^{201}$Tl, $^{123}$I, $^{131}$I, $^{160}$Gd, $^{148}$Nd, $^{89}$Sr, and $^{211}$At. In some embodiments, radionuclide is selected from the group consisting of $^{18}$F (as $^{18}$F-AlF), $^{43}$Sc, $^{44}$Sc, $^{51}$Mn, $^{61}$Cu, $^{64}$Cu, $^{67}$Cu, $^{68}$Ga, $^{86}$Y, $^{89}$Zr, $^{99m}$Tc, $^{18}$F, $^{76}$B, $^{77}$Br, $^{111}$In, $^{123}$I, $^{124}$I, $^{125}$I, $^{152}$Tb, $^{15}$Tb, $^{212}$Pb and $^{203}$Pb.

In certain embodiments, the radionuclide is selected from the group consisting of therapeutic radionuclides suitable for therapeutic use: $^{47}$Sc, $^{67}$Cu, $^{89}$Sr, $^{90}$Y, $^{131}$I, $^{153}$Sm, $^{149}$Tb, $^{161}$Tb, $^{177}$Lu, $^{186}$Re, $^{188}$Re, $^{211}$At, $^{212}$Pb, $^{212}$Bi, $^{223}$Ra, $^{224}$Ra, $^{225}$Ac, $^{226}$Th, and $^{227}$Th.

In certain embodiments, the radionuclide is selected from the group consisting of radionuclides suitable for medical imaging use: $^{18}$F (as $^{18}$F-AlF), $^{111}$In, $^{203}$Pb, $^{212}$Pb, $^{61}$Cu, $^{64}$Cu, $^{68}$Ga, $^{86}$Y, $^{89}$Zr, and other medical radionuclides useful for medical imaging.

In certain embodiments, the radionuclide is $^{67}$Cu, $^{177}$Lu, $^{186}$Re, $^{188}$Re, $^{211}$At, $^{212}$Pb, $^{224}$Ra, $^{225}$Ac or other medical radionuclide useful for treating cancer or tumor.

In one embodiment, the radionuclide may be a lead radionuclide that is any one selected from the group consisting of Pb-196, Pb-197, Pb-198, Pb-199, Pb-200, Pb-201, Pb-202, Pb-203, Pb-205, Pb-209, Pb-210, Pb-211, Pb-212, Pb-213, Pb-214, Pb-215, and Pb-216. According to certain embodiments, the lead radionuclide that is chelated with a chelator, for example a Pb-specific chelator (PSC), comprises any of Pb-203 ($^{203}$Pb) or Pb-212 ($^{212}$Pb). Pb-203 allows detection of targeted cells with single-photon emission computed tomography (SPECT) for diagnostic imaging, whereas Pb-212 is suitable for delivering therapeutic doses of radiation to cancer cells as well as being used for SPECT imaging.

In another embodiment, the radionuclide may be a copper radionuclide that is any selected from the group consisting of Cu-55, Cu-56, Cu-57, Cu-58, Cu-59, Cu-60, Cu-61, Cu-62, Cu-63, Cu-64, Cu-65, Cu-66, Cu-67, Cu-68, Cu-69, Cu-70, Cu-71, Cu-72, Cu-73, Cu-74, Cu-75, Cu-76, Cu-77, Cu-78, Cu-79, Cu-80, Cu-81, Cu-82, Cu-83, and Cu-84. According to certain embodiments, the copper radionuclide that is conjugated by a chelator comprises any of Cu-61, Cu-64 or Cu-67.

Linkers (L)

Any suitable linker known to those skilled in the art in view of the present disclosure can be used herein. The linkers can contain, for example, a substituted or unsubstituted alkyl, a substituted or unsubstituted heteroalkyl moiety, a substituted or unsubstituted aryl or heteroaryl, an ethylene glycol linker, a polyethylene glycol (PEG) linker, a linker comprising ethylene glycol or PEG that is linked to amino acid or amino acids, a substituted or unsubstituted amino acid, a substituted or unsubstituted peptide linker, a sugar-based linker, or a cleavable linker, such as a disulfide linkage or a protease cleavage site such as valine-citrulline-p-aminobenzyl (PAB). For example, in certain embodiments, the linker can comprise an ethylene glycol group or a polyethylene glycol group that has been modified on either end or both ends.

In some embodiments, the linker comprises a polyethylene glycol (PEG) moiety, such as (—$CH_2$—$CH_2$—O—) 1-10. For example, according to certain embodiments, the linker can comprise a polyethylene glycol moiety that is formed from a modified PEG to provide for covalent bonding on either end or both ends, such as amino-polyethylene glycol-acid, having from 1 to 10 ethylene glycol groups, such as any of 1, 2, 3, 4, 5, 6, 7, 8, 9 or 10 ethylene glycol groups, such as 2 ethylene glycol groups, and having an amino group on one end of the linker and an acid group on the other (e.g. $NH_2$—($CH_2CH_2$—O)—$(CH_2)_m$—C(=O)OH, where n and m are 1-10). The linker formed from the modified PEG may comprise the formula —$NH_2$—$(CH_2CH_2O)_n$—$(CH_2)_m$—C(=O)—, where n and m are independently 1-10, such as independently any of 1, 2, 3, 4, 5, 6, 7, 8, 9 or 10. In one embodiment, m is 1-2, and n is 1-10, such as 1-8, 1-6, 1-4, 2-4, and even 4.

According to certain embodiments, the linkers used in the present invention may improve the retention of the peptidomimetic conjugate on the cell surface. According to certain embodiments, the linkers may improve the internalization of the composition into cells. According to certain embodiments, the linker may improve the retention of the peptidomimetic conjugate in tumors for more precise delivery of radiation or cytotoxic agents to the tumor cells or cancer cells.

For example, in one embodiment, the linker (L) used in the peptidomimetic conjugate disclosed herein comprises any structure selected from the group consisting of:

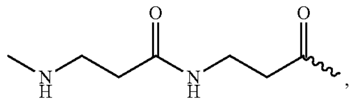
,

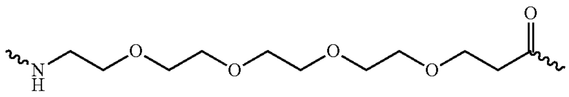
,

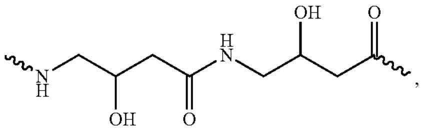
,

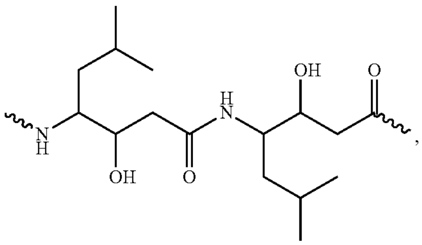
,

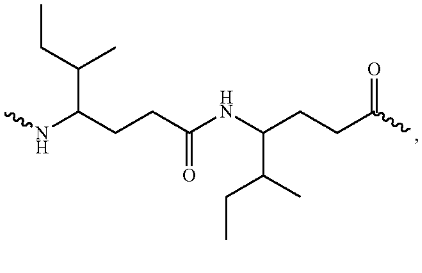
,

-continued

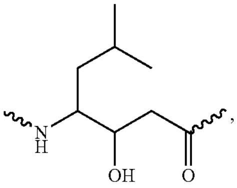,

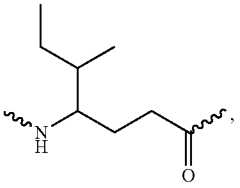, and

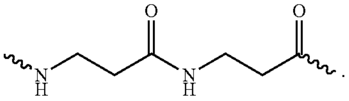.

The linker, as described herein, may comprise an amino acid, such as Gly, Ala, Gin, Glu, His, in L- or D-form, or an amino acid polymer consisting of one or more of these amino acids, or any other chemical moiety, such as ethylene glycol or polyethylene glycol (PEG) or a carbohydrate, as well as aminohexanoyl or aminobenzoyl or piperidine moieties. In some embodiments the linker can be 6-aminohexanoic acid, 4-aminobutyric acid, 4-amino-1-carboxymethylpiperidine (Pip linker), or urea or another chemical moiety that allows introducing a functional group in the peptidomimetic. In some embodiments the linker is a combination of the above-mentioned linkers. In one embodiment, the linker (L) further comprises up to six D-form amino acids. For example, in one embodiment, the linker (L) has the structure of

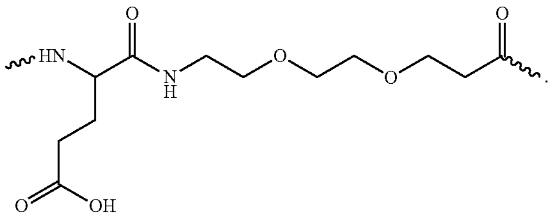.

Some exemplary linkers (L) are also listed in Table 1.

TABLE 1

| Exemplary linkers | | |
|---|---|---|
| Linker | Description | Structure |
| Linker 1 | PEG2 | 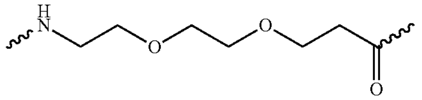 |
| Linker 2 | PEG4 | 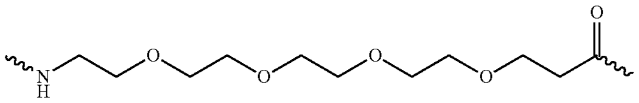 |
| Linker 3 | dGlu-PEG2 | 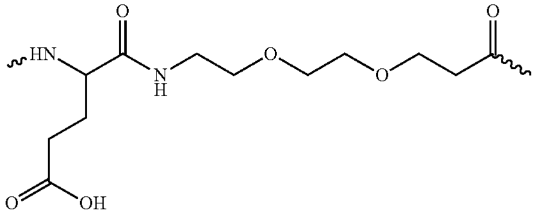 |
| Linker 4 | dGlu-PEG4 | 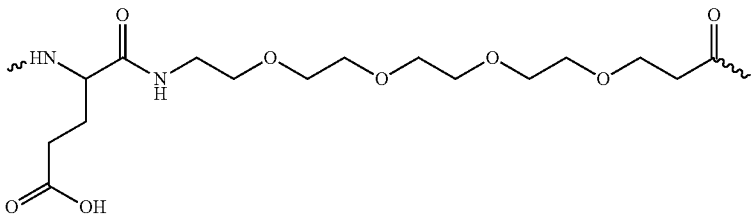 |
| Linker 5 | (Gabob)2 | 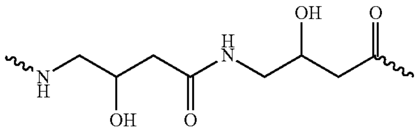 |

TABLE 1-continued

| Exemplary linkers | | |
|---|---|---|
| Linker | Description | Structure |
| Linker 6 | (Sta)2 | 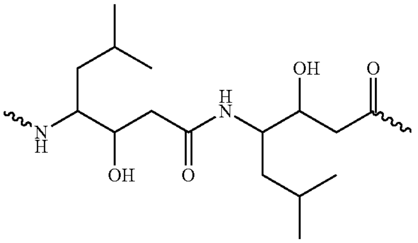 |
| Linker 7 | (MHA)2 | 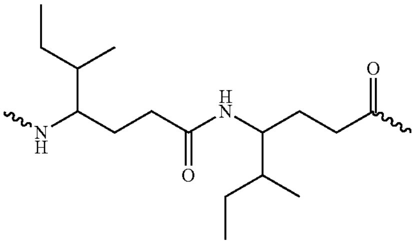 |
| Linker 8 | Sta | 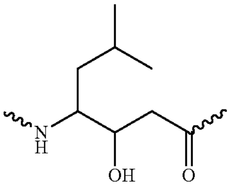 |
| Linker 9 | MHA | 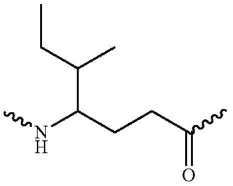 |
| Linker 10 | dGlu-Gabob-Gabob | 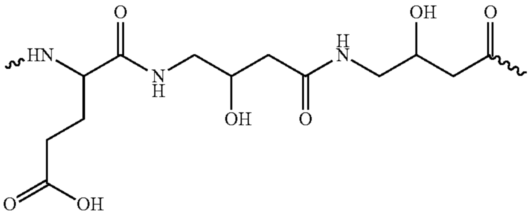 |
| Linker 11 | βAla-βAla | 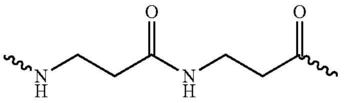 |

Pharmaceutical Formulation

The radiolabeled peptidomimetic conjugates or radiopharmaceutical compounds described herein can be administered in a radiopharmaceutical formulation suitable for delivery to a human subject, such as for example via intravenous, intramuscular, topical or subcutaneous administration, and may be in form of an aqueous solution (e.g. saline solution) containing the radiolabeled conjugate in a concentration sufficient for one or more of diagnostic (imaging) and therapeutic purposes, as well as optional radioprotectants and/or antioxidants, buffers, etc. The radiolabeled conjugate may be prepared in phosphate-buffered saline (PBS) with or without radioprotectants including any one or more of ascorbic acid, sodium acetate, gentisic acid, and ethanol, at concentrations that are suitable for human or animal use.

According to certain embodiments, the radiolabeled peptidomimetic conjugate or radiopharmaceutical compound may be administered intravenously or intraperitoneally by infusion or injection. Solutions of the conjugate or its salts can be prepared in water, isotonic saline, phosphate-buffered saline, optionally mixed with a nontoxic surfactant. Dispersions can also be prepared in glycerol, liquid polyethylene glycols, triacetin, and mixtures thereof and in oils. In certain embodiments, the final solution contains ethanol from 0 to 20% v/v. In certain embodiments, the final pH of the solution is 4-8. In certain embodiments, the conjugate is administered with certain amino acids or other chemical compounds that help reduce the uptake of radioactive compound in the kidneys or other non-tumor tissues or organs. In certain embodiments, the amino acids are lysine and arginine. According to certain embodiments, a preparation containing the conjugate contains a preservative excipient to prevent the growth of microorganisms.

According to one embodiment, a formulation of the peptidomimetic conjugate described herein may be provided in lyophilized form, such as for example for storage of the conjugate prior to labelling and administration. For example, an aqueous solution of the conjugate may be prepared with additional formulation components such as buffers, radioprotectants, or other excipients, and the solution may be lyophilized (freeze dried) to provide for storage of the conjugate formulation. According to certain embodiments, the lyophilized formulation can be stored under vacuum or in an inert atmosphere. The lyophilized formulation can be reconstituted prior to administration, such as for example by combining with a sterile aqueous solution, to form a liquid composition. According to certain embodiments, an aqueous solution provided to reconstitute the lyophilized formulation may also optionally include components, such as any of buffers, radioprotectants, or other components to stabilize the composition, and/or to improve administration. According to certain embodiments, the reconstituted formulation can be chelated with a radionuclide selected for treatment or imaging. The formulations may also comprise a radioprotectant, such as chelating agents or sodium ascorbate.

According to certain embodiments, sterile injectable solutions are prepared by incorporating the conjugate in the required amount in the appropriate solvent with various other ingredients enumerated above, as required, followed by filter sterilization.

The dosage of the radiolabeled peptidomimetic conjugates disclosed herein for administrating to a subject may vary depending on age, weight, and condition of the subject. Treatment may be initiated with low dosages and increased until a desired or an optimal effect under the circumstances is reached.

According to certain aspects, a pharmaceutical composition is formulated to be compatible with its intended route of administration. For example, the peptidomimetic conjugate may be introduced directly into the cancer of interest via direct injection. Additionally, examples of routes of administration include oral, parenteral, e.g., intravenous, slow infusion, intradermal, subcutaneous, transdermal (topical), transmucosal, and rectal administration. Such compositions can comprise the conjugate and a pharmaceutically acceptable carrier. As used herein, “pharmaceutically acceptable carrier” is intended to include any and all solvents, dispersion media, coatings, antibacterial and anti-fungal agents, isotonic and absorption delaying agents, chelating agents, compatible with pharmaceutical administration. The use of such media and agents for pharmaceutically active substances is well known in the art.

According to certain embodiments, solutions or suspensions can include the following components: a sterile diluent such as water for injection, saline solution (e.g., phosphate buffered saline (PBS)), fixed oils, a polyol (for example, glycerol, propylene glycol, and liquid polyethylene glycol, and the like), glycerine, or other synthetic solvents; antibacterial and antifungal agents such as parabens, chlorobutanol, phenol, ascorbic acid, thimerosal, and the like; antioxidants such as ascorbic acid, gentisic acid, sodium bisulfite; chelating agents such as EDTA, DTPA, DMSA, DMPS; buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and by the use of surfactants. In many cases, it is preferable to include isotonic agents, for example, sugars, polyalcohols such as mannitol or sorbitol, and sodium chloride in the composition. The parenteral preparation can be enclosed in ampules, disposable syringes, or multiple dose vials made of glass or plastic.

According to certain aspects, it may be advantageous to formulate compositions in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms of the invention are dependent upon the amount of a compound necessary to produce the desired effect(s). The amount of a compound necessary can be formulated in a single dose, or can be formulated in multiple dosage units. Treatment may require a one-time dose, or may require repeated doses.

Diagnostic and Therapeutic Uses

Embodiments of the present disclosure provide methods of targeting cells expressing CCK2R, the methods comprise administering a radiolabeled peptidomimetic compound comprising the CCK2R targeted peptidomimetic conjugate as described herein.

Embodiments of the present disclosure further provide methods of imaging and/or diagnosing a subject having a disorder that is associated with aberrant CCK2R expression, the method comprising administering to the subject a radiolabeled peptidomimetic compound comprising the CCK2R targeted peptidomimetic conjugate described herein, and imaging the subject. Thus, aspects of the present disclosure provide methods for imaging or diagnosing a cancer or tumor in a subject in need thereof, by administering a radiopharmaceutical compound that is chelated with a radionuclide described herein to the subject, and imaging cells or organs or tissues having the radiolabeled peptidomimetic conjugate bound thereto. That is, when the peptidomimetic conjugate is labeled with a radionuclide that is suitable for medical imaging purposes, the radiolabeled peptidomimetic conjugate can be administered to a subject and will accumulate at target sites to which the binding moiety is selective. Imaging techniques such as single photon emission computed tomography (SPECT) imaging or positron emission topography (PET) imaging can be performed to view the accumulation of the radiolabeled peptidomimetic conjugate at target sites, which may be indicative of a location of cancer cells or tumor cells, such as cancer cells or tumor cells expressing CCK2R on the cell surface.

According to certain aspects, $^{203}$Pb (Pb-203) and $^{212}$Pb (Pb-212) may be suitable for imaging processes such as SPECT, to provide for imaging and diagnosing of the presence or extent of cancer and/or tumors in a subject.

In one embodiment, the present disclosure provides a method of imaging or diagnosing a subject suffering from a cancer associated with aberrant expression of CCK2R, the method comprising administering the peptidomimetic conjugate as described herein to the subject, wherein the peptidomimetic conjugate is chelated with a lead radionuclide $^{203}$Pb or $^{212}$Pb, and imaging the subject.

One aspect of the present disclosure provide methods for imaging or diagnosing a cancer or tumor or cancer cells or tumor cells in a subject in need thereof, by administering a fluorophore-labeled peptidomimetic conjugate described herein to the subject, and imaging cells or organs or tissues having the fluorophore labeled peptidomimetic conjugate bound thereto. That is, when the peptidomimetic conjugate is labeled with a fluorophore that is suitable for imaging purposes, the fluorophore-labeled peptidomimetic conjugate can be administered to a subject systematically or locally and will accumulate at target sites to which the binding moiety is selective. Fluorescence imaging can be performed to view the accumulation of the fluorophore-labeled peptidomimetic conjugate at target sites, which may be indicative of a location of cancer cells or tumor cells expressing CCK2R on the cell surface.

Furthermore, according to certain embodiments, a method of treating a subject having a disorder that is associated with aberrant CCK2R expression is disclosed herein; the method comprises administering to the subject a radiolabeled compound comprising the CCK2R targeted peptidomimetic conjugate disclosed in the present invention.

Thus, the present disclosure provides methods of treatment of cancer or tumor in a subject in need thereof, by administering a peptidomimetic conjugate comprising the CCK2R targeted peptidomimetic which is chelated with a radionuclide to the subject, in therapeutically effective amounts that are sufficient to treat the subject. That is, when the peptidomimetic conjugate is chelated with (or radiolabeling with) a radionuclide that is suitable for therapeutic purposes, the radiolabelled peptidomimetic conjugate can be administered to a subject and will accumulate at target sites to which the binding moiety is selective, such as to tumor cells expressing CCK2R. The radiation emitted by the radiolabelled peptidomimetic conjugate bound to the target cells may provide a cell killing effect that is selective for the target cells, thereby providing treatment.

According to certain aspects, $^{212}$Pb (Pb-212) may be used in the present invention as the radionuclide that is able to kill cancer cells, thus providing treatment of cancer and/or tumors in a subject. According to certain aspects, $^{67}$Cu (Cu-67), $^{177}$Lu (Lu-177), $^{211}$At (At-211), or $^{225}$Ac (Ac-225) may be used in the present invention as the radionuclide that is able to kill cancer cells, thus providing treatment of cancer and/or tumors in a subject.

For example, in one embodiment, the present disclosure provides a method of treating a subject suffering from a cancer associated with aberrant expression of CCK2R, the method comprising administering the peptidomimetic conjugate as described herein, as chelated with a lead radionuclide $^{212}$Pb, to the subject, in a dosage sufficient to kill cancer cells or tumor cells.

According to one embodiment, the present disclosure provides methods of treatment of cancer in a subject in need thereof, by administering a peptidomimetic conjugate comprising one or multiple cytotoxic agents and the CCK2R targeted peptidomimetic disclosed herein to the subject, wherein the one or multiple cytotoxic agents is/are covalently linked to the CCK2R targeted peptidomimetic, in a therapeutically effective amount that is sufficient to treat the subject. That is, when the peptidomimetic conjugate is linked with one or multiple cytotoxic agents that is/are suitable for therapeutic purposes, the cytotoxic agent-labeled peptidomimetic conjugate can be administered to a subject and will accumulate at target cells expressing CCK2R on the cell surface.

According to one embodiment, the present disclosure further provides a method of diagnosing and treating a subject suffering from a cancer or a tumor associated with expression of CCK2R, the method comprising: diagnosing the subject by administering the peptidomimetic conjugate as described herein to the subject, as chelated with a lead radionuclide $^{203}$Pb or $^{61}$Cu or $^{64}$Cu, and imaging cells or tissues or organs having the radiolabelled peptidomimetic conjugate bound thereto to diagnose the subject as being afflicted with the cancer or tumor, and treating the subject diagnosed as being afflicted by the cancer or tumor, by administering the peptidomimetic conjugate as described herein, as chelated with a lead radionuclide $^{212}$Pb or $^{67}$Cu, in a dosage sufficient to kill cancer cells or tumor cells. According to another embodiment, the radionuclides that can be used in the present invention comprise $^{68}$Ga for imaging, and $^{177}$Lu, $^{211}$At and $^{225}$Ac for therapeutic purposes.

In one embodiment, the cell or tissue or organ of a subject is imaged using single-photon emission computed tomography (SPECT) imaging, optionally in combination with computed tomography (CT) imaging. In one embodiment, the cell or tissue or organ of a subject is imaged using positron emission tomography (PET) imaging, optionally in combination with computed tomography (CT) imaging.

According to certain embodiments, the cancer or tumor in a subject that can be treated with the peptidomimetic conjugates or the radiopharmaceutical compounds disclosed herein is associated with CCK2R expression. For example, the cancer or tumor may be selected from the group consisting of thyroid cancer such as medullary thyroid carcinomas (MTC), lung cancers such as small cell lung cancer (SCLC), gastrointestinal tumours, tumours of the nervous system such as astrocytomas and meningiomas, ovarian cancers, gastrointestinal cancers, colorectal cancer (CRC), neuroendocrine tumours, gastroenteropancreatic tumours, neuroblastomas, tumours of the reproductive system such as breast carcinomas, endometrial cancer, ovarian cancers, prostate cancer, testicular germ cell tumor, insulinomas, vipomas, bronchial and ileal carcinoids, leiomyosarcomas, leiomyomas, and granulosa cell tumours.

In one embodiment, the cancer is any of colorectal cancer (CRC), small cell lung cancer (SCLC), medullary thyroid cancer (MTC), ovarian cancer, testicular germ cell tumor, prostate cancer, breast cancer, and endometrial cancer.

In certain embodiments, the radiopharmaceutical compound or peptidomimetic conjugate disclosed herein is administered intravenously or parenterally. In certain embodiments, the radiopharmaceutical compound or peptidomimetic conjugate is administered in a single dose. In certain embodiments, the radiopharmaceutical compound or peptidomimetic conjugate is administered in multiple doses. In certain embodiments, the radiopharmaceutical compound or peptidomimetic conjugate is administered sequentially daily for several days. In certain embodiments, the radiopharmaceutical compound or peptidomimetic conjugate is administered once per week for 1 month. In certain embodiments, the radiopharmaceutical compound or peptidomimetic conjugate is administered once per week for up to 6 months. In certain embodiments, the radiopharmaceutical compound or peptidomimetic conjugate is administered once every four weeks for up to 6 months. In certain embodiments, the radiopharmaceutical compound or peptidomimetic conjugate is administered once every six, seven, or eight weeks for up to 6 months. For example, the radiopharmaceutical or peptidomimetic conjugate is administered once every eight weeks for up to four cycles or up to eight cycles.

In certain embodiments, the radiopharmaceutical compound or peptidomimetic conjugate is administered in a dose from 0.1 mCi to 1 mCi for medical imaging. In certain embodiments, the radiopharmaceutical compound or peptidomimetic conjugate is administered in a dose of up to 10 mCi for medical imaging. In certain embodiments, the radiopharmaceutical compound or peptidomimetic conjugate is administered in a dose of up to 50 mCi for medical imaging. In certain embodiments, the radiopharmaceutical compound or peptidomimetic conjugate is administered in a dose from 0.1 mCi to 1 mCi for medical treatment of cancer or tumor. In certain embodiments, the radiopharmaceutical compound or peptidomimetic conjugate is administered in a dose of up to 5 mCi for medical treatment of cancer or tumor. In certain embodiments, the radiopharmaceutical compound or peptidomimetic conjugate is administered in a dose of up to 10 mCi for medical treatment of cancer or tumor. In certain embodiments, the radiopharmaceutical compound or peptidomimetic conjugate is administered in a dose of up to 100 mCi for medical treatment of cancer or tumor. In certain embodiments, the radiopharmaceutical compound or peptidomimetic conjugate is administered in a dose of up to 200 mCi for medical treatment of cancer or tumor. In certain embodiments, the radiopharmaceutical compound or peptidomimetic conjugate is administered in a dose of up to 500 mCi for medical treatment of cancer or tumor. In certain embodiments, the radiopharmaceutical compound or peptidomimetic conjugate is administered in a single dose. In certain embodiments, the radiopharmaceutical compound or peptidomimetic conjugate is administered in multiple doses over multiple months of time.

According to certain embodiments, the radiopharmaceutical compound or peptidomimetic conjugate disclosed herein can be administered in combination with one or more additional anti-cancer agents, and/or with other radiopharmaceutical compound or peptidomimetic conjugate. The one or more additional anti-cancer agents can be administered before, simultaneously with, or after administering the radiopharmaceutical compound or peptidomimetic conjugate disclosed herein.

Preparation of Binding Peptidomimetics and Conjugates

An exemplary embodiment of synthesis of a CCK2R targeted peptidomimetic and creation of the conjugate is provided herein, for purposes of illustration.

Solid Phase Peptide Synthesis of PSVCCK2R-13 on Fmoc-Rink MBHA Resin

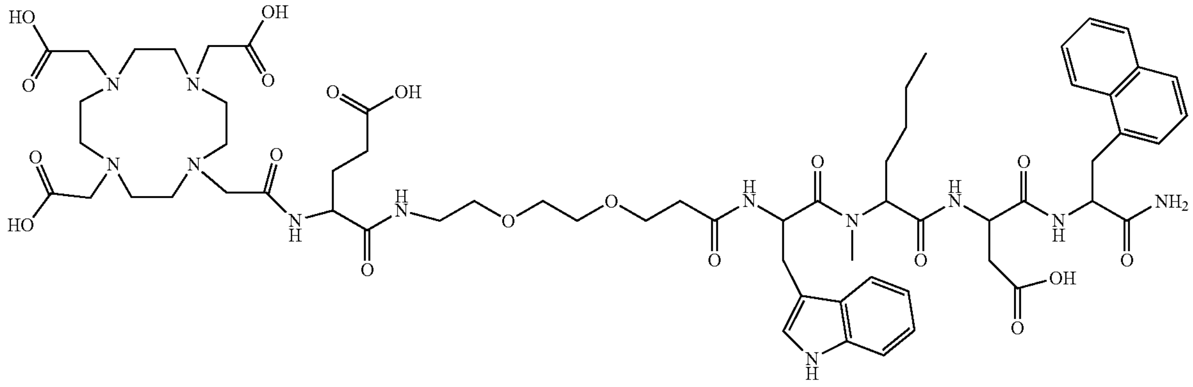 [SMILES: CCCCC(C(=O)NC(CC(=O)O)C(=O)NC(Cc1cccc2ccccc12)C(N)=O)N(C)C(=O)C(Cc1c[nH]c2ccccc12)NC(=O)CCOCCOCCNC(=O)C(CCC(=O)O)NC(=O)CN1CCN(CC(=O)O)CCN(CC(=O)O)CCN(CC(=O)O)CC1]

PSVCCK2R-13 was synthesized on a 100 μMol scale using a CEM Liberty Prime 2.0 microwave assisted automated peptide synthesizer (Mathews, NC) utilizing pyrollidine to remove Fmoc and DIC/Oxyma Pure double couplings for all amino acids at 90° C. with microwave heating. Upon synthesis completion, the peptidomimetics was washed with DCM and methanol to remove DMF and dry the resin. The peptidomimetics was then removed from the resin and side chain deprotected using a cleavage cocktail of TFA/H2O/TIS (95/2.5/2.5%) for two hours followed by precipitation in ice cold diethyl-ether for approximately 30 minutes. The precipitate was centrifuged at 4000 rpm for 10 minutes at 4° C. and the supernatant decanted. The crude peptidomimetics was reconstituted in ultrapure water and placed on dry ice to freeze. Once frozen, the crude peptidomimetics were placed on a Labconco Freezone 2.5 L freeze dryer to lyophilize. The lyophilized peptidomimetics were reconstituted in ultrapure water and purified to homogeneity with a Teledyne ISCO ACCQPrep 150 preparative RP-HPLC system by injecting the crude material onto a Teledyne ISCO RediSep C18, 5 μm column (10×250 mm) eluted with 0.1 v/v % TFA using a 20-50 v/v % ACN gradient at 18.9 mL/min over 30 min while monitoring absorbance at 214 nm (peptide backbone) and 280 nm (aromatic amino acids). The peak corresponding to the product was collected and pooled from multiple runs, lyophilized, and stored at −20° C. Purified peptidomimetics were reconstituted in water and quantified by UV absorbance at 280 nm to determine isolated yield. Purified peptidomimetics were characterized by LC-MS (FIG. 1) on an Agilent 1200 series HPLC interfaced with an Agilent 1956B LC/MSD SL MS by injecting peptidomimetics onto an Agilent Zorbax Eclipse XBD-C18 analytical column (4.6×150 cm) eluted at 0.7 mL/min with 0.1 v/v % TFA and an acetonitrile gradient of 5-80 v/v % over 10 minutes. Mass spectral data was obtained in the positive mode. MS: 659.0 m/z (M+2H) observed 1316.0, 1317.6 m/z (M+H) observed 1316.6, calculated 1316.5.

Solid Phase Peptide Synthesis of PSVCCK2R-42 on Fmoc-Rink MBHA Resin

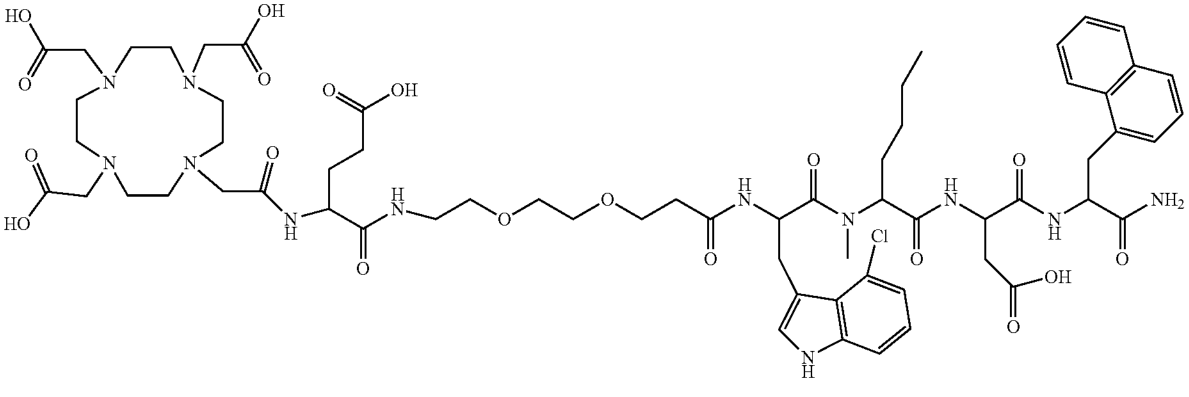 [SMILES: CCCCC(C(=O)NC(CC(=O)O)C(=O)NC(Cc1cccc2ccccc12)C(N)=O)N(C)C(=O)C(Cc1c[nH]c2cccc(Cl)c12)NC(=O)CCOCCOCCNC(=O)C(CCC(=O)O)NC(=O)CN1CCN(CC(=O)O)CCN(CC(=O)O)CCN(CC(=O)O)CC1]

Figure 2:
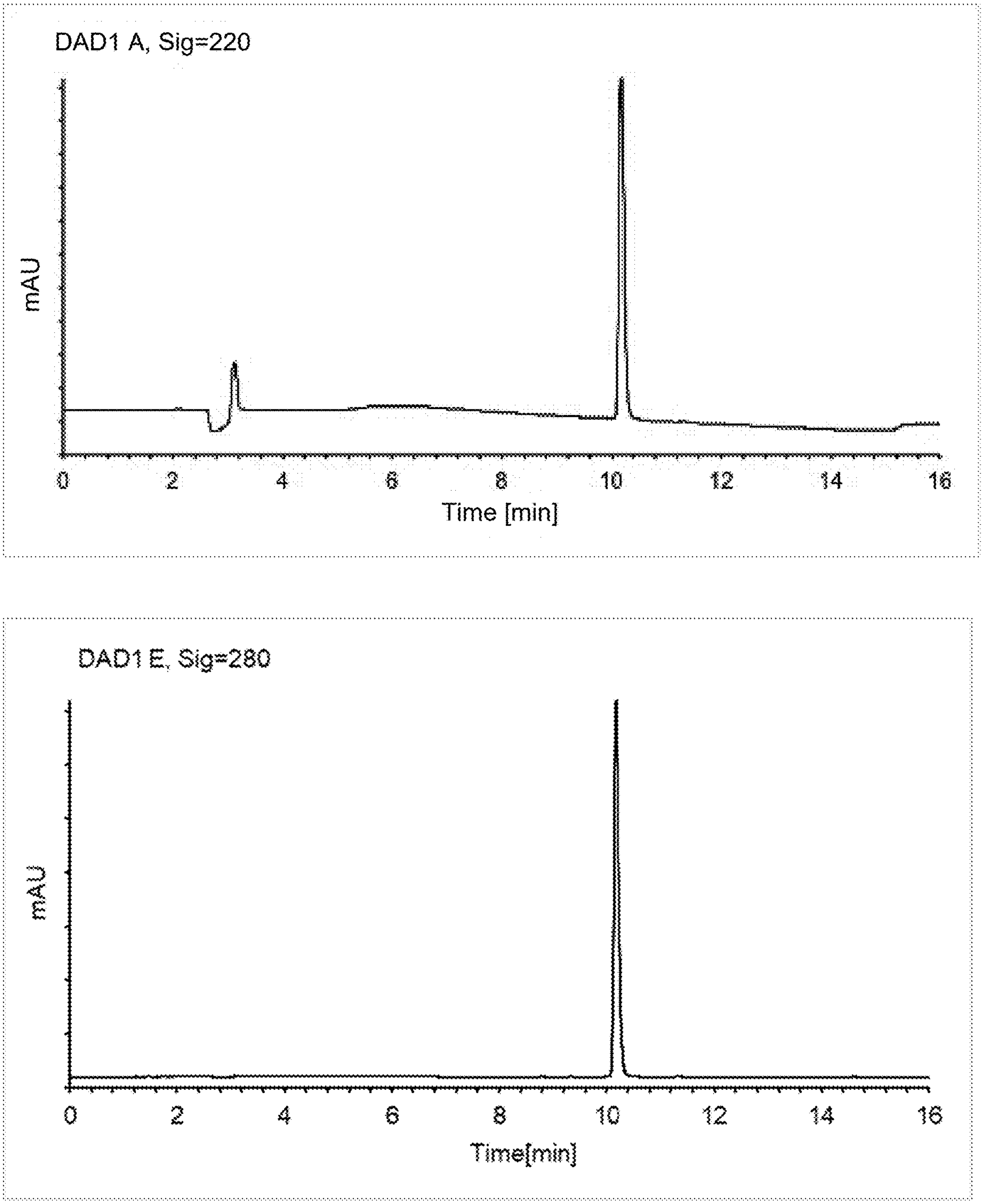
FIG. 2 shows the LC-MS Characterization Data for PSV-CCK2R-42.
Figure 2:
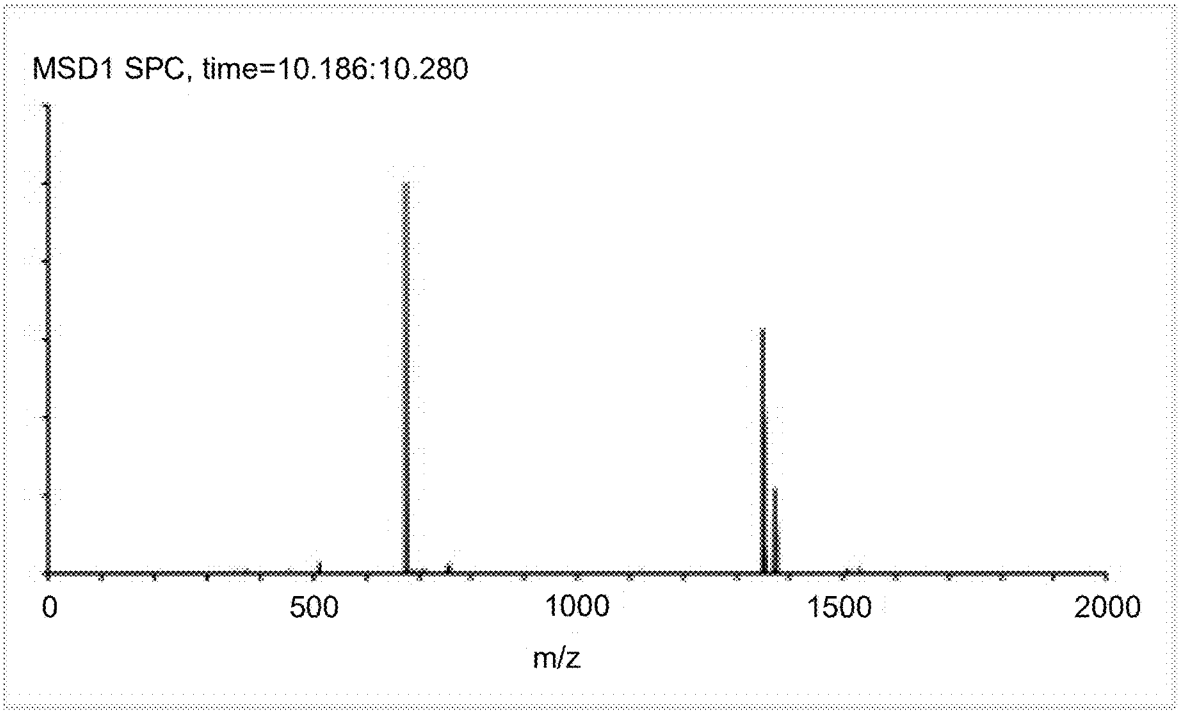
Figure 3:
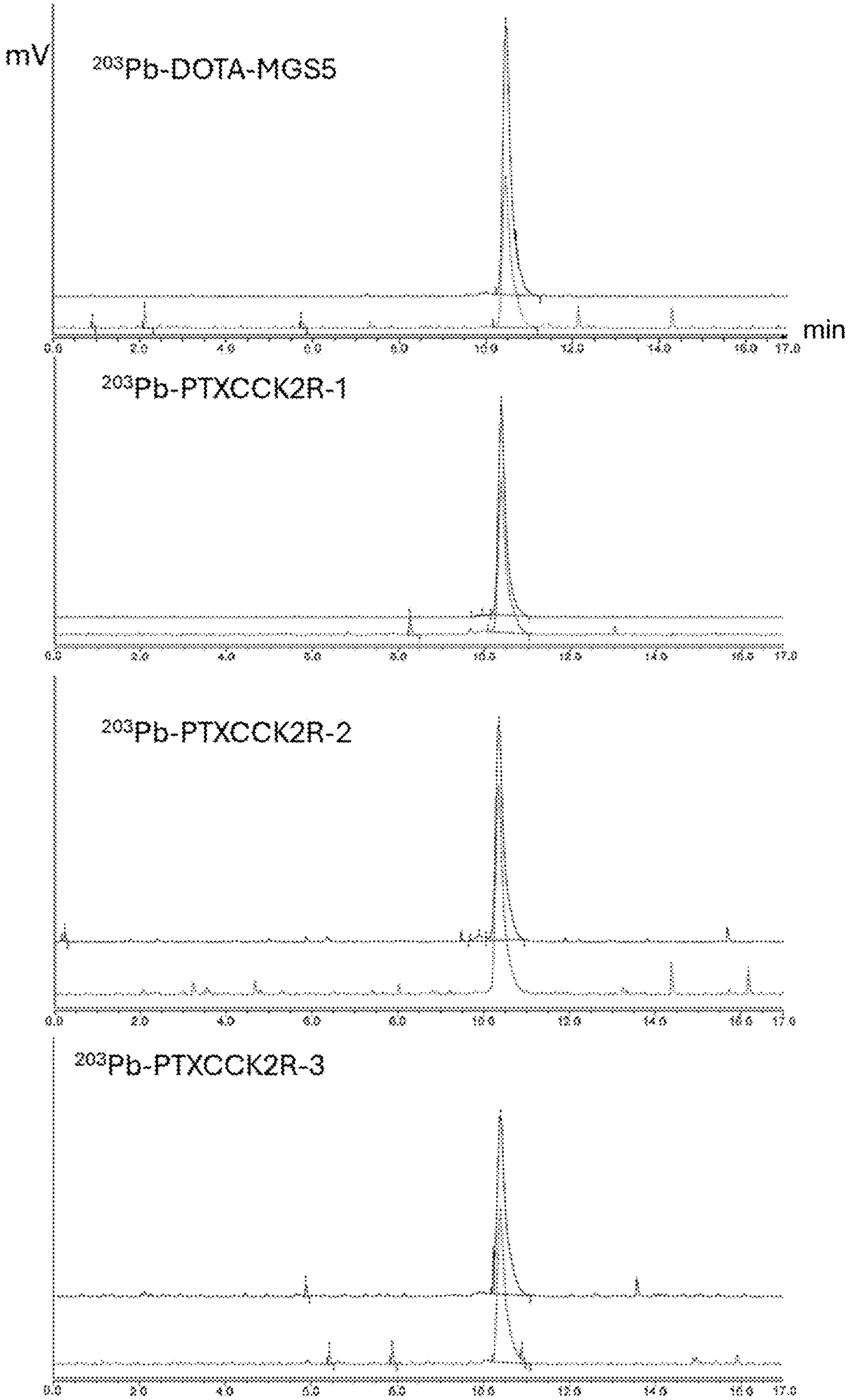
FIG. 3 shows the radiochemical purity at the end of synthesis (EOS) (top trace of the radio-chromatograms) and 20-hour serum stability (bottom trace, dotted line) by Radio-HPLC of $^{203}$Pb-labeled CCK2R targeted peptidomimetic conjugates.
Figure 3:
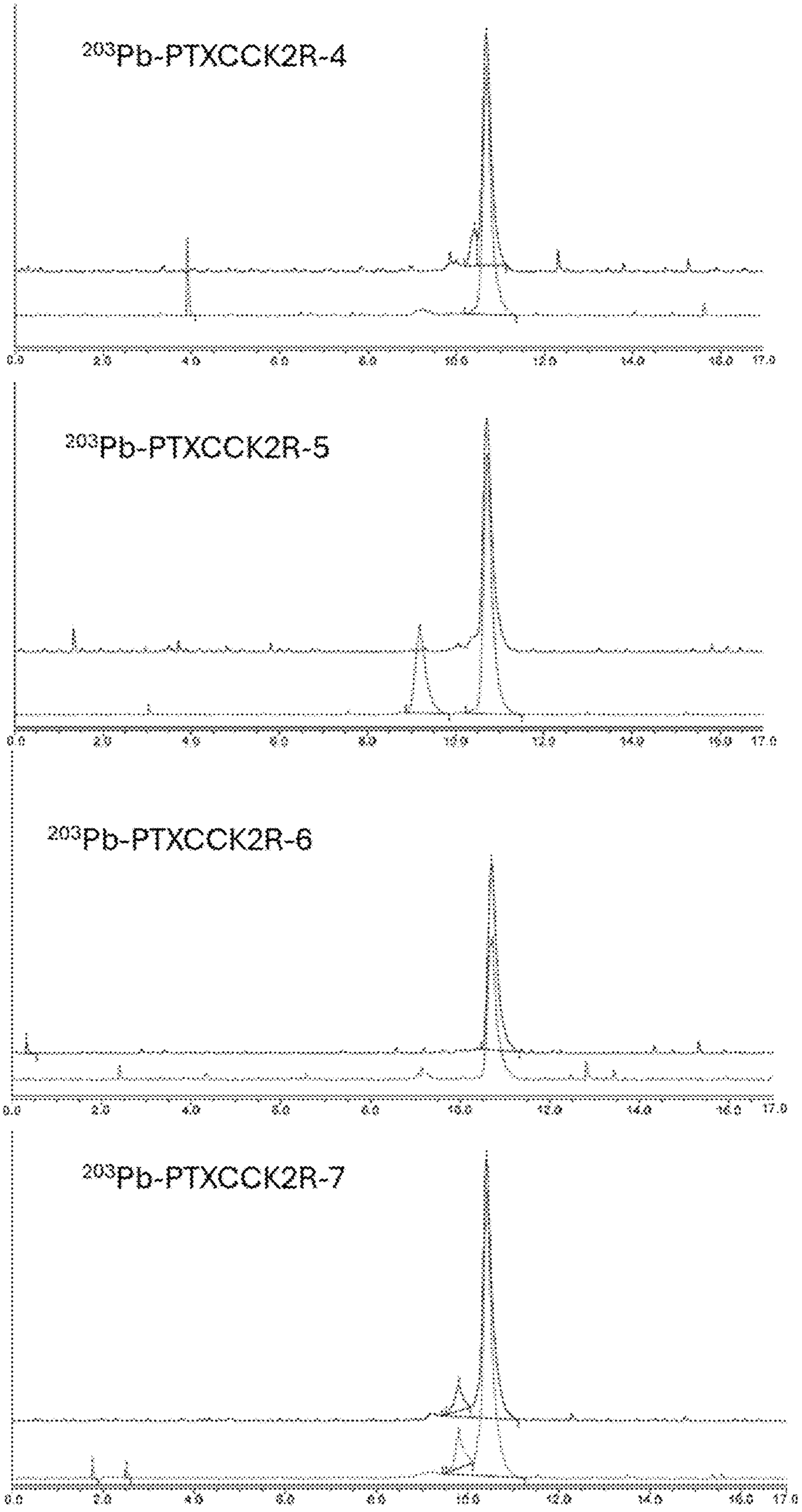
Figure 3:
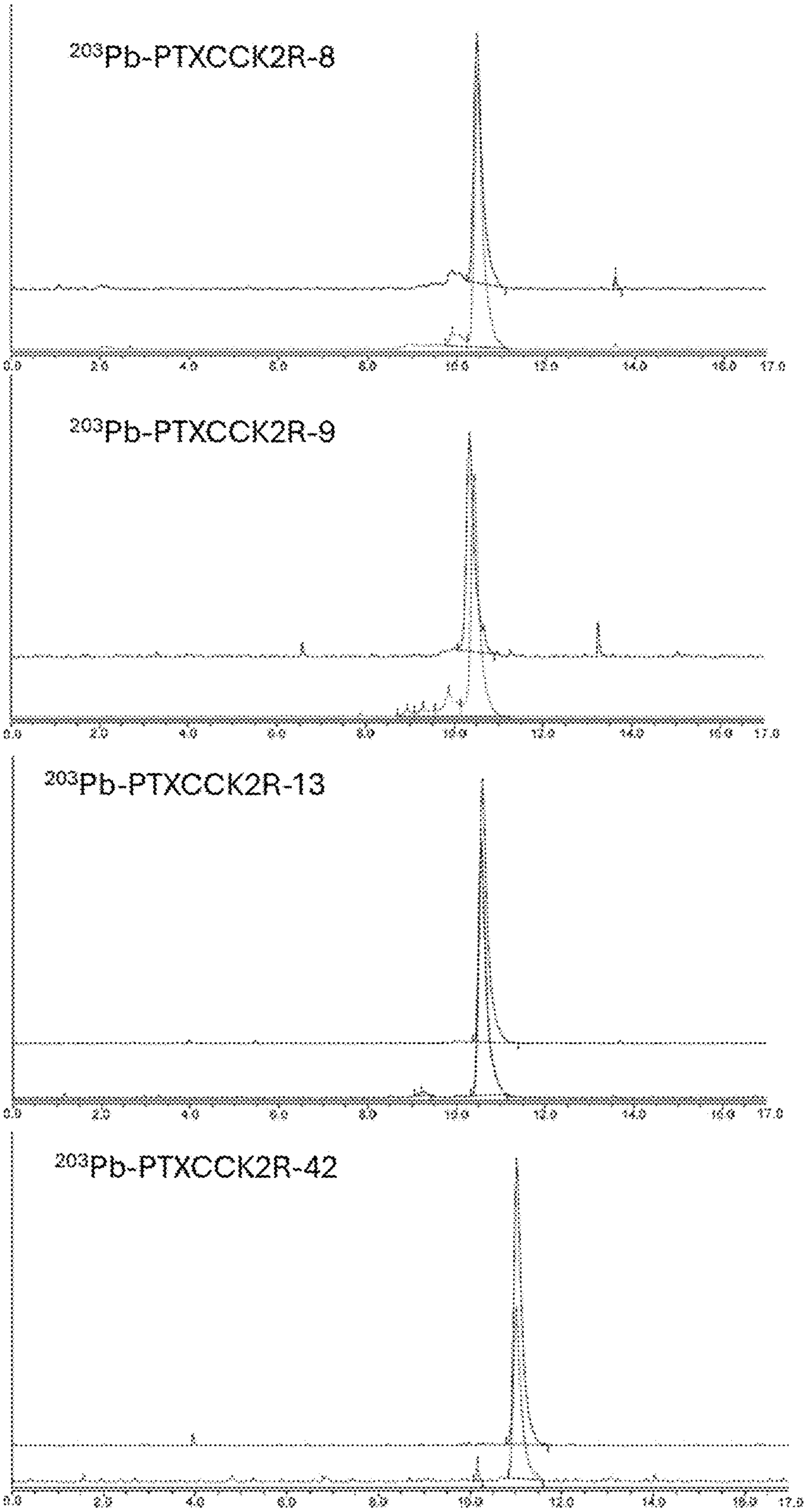
Figure 3:
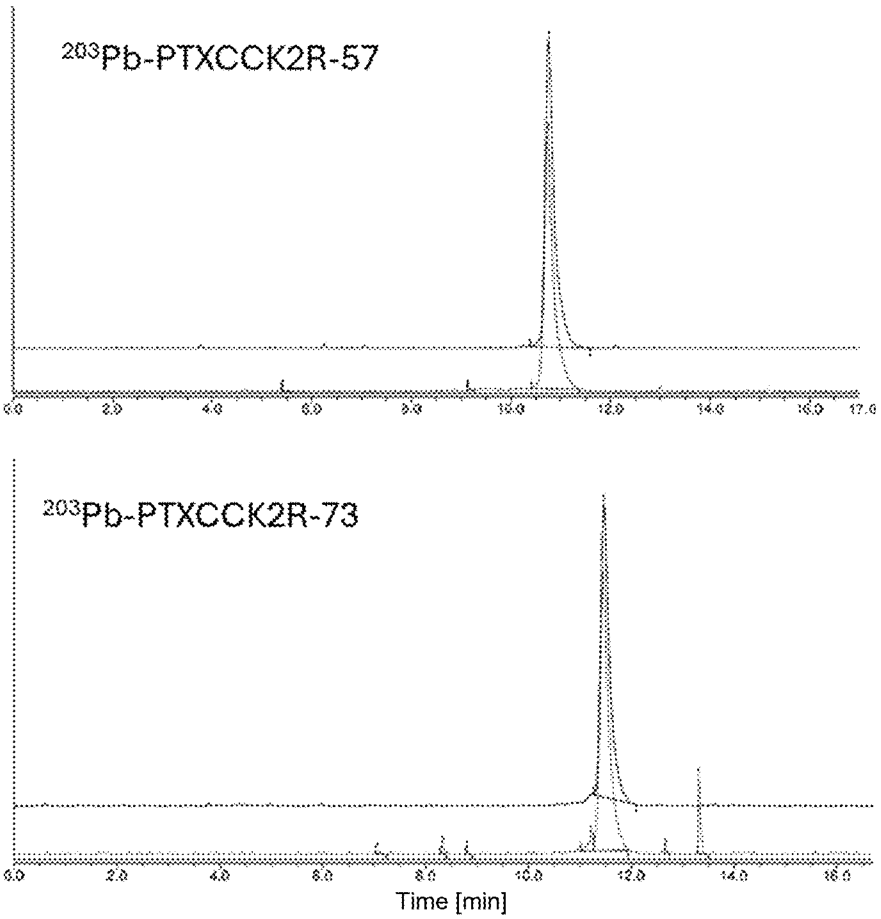

PSVCCK2R-42 was synthesized on a 100 μMol scale using a CEM Liberty Prime 2.0 microwave assisted automated peptide synthesizer (Mathews, NC) utilizing pyrollidine to remove Fmoc and DIC/Oxyma Pure double couplings for all amino acids at 90° C. with microwave heating. Upon synthesis completion, the peptidomimetics was washed with DCM and Methanol to remove DMF and dry the resin. The peptidomimetics was then removed from the resin and side chain deprotected using a cleavage cocktail of TFA/H2O/TIS (95/2.5/2.5%) for two hours followed by precipitation in ice cold diethyl-ether for approximately 30 minutes. The precipitate was centrifuged at 4000 rpm for 10 minutes at 4° C. and the supernatant decanted. The crude peptidomimetics was reconstituted in ultrapure water and placed on dry ice to freeze. Once frozen, the crude peptidomimetics were placed on a Labconco Freezone 2.5 L freeze dryer to lyophilize. The lyophilized peptidomimetics were reconstituted in ultrapure water and purified to homogeneity with a Teledyne ISCO ACCQPrep 150 preparative RP-HPLC system by injecting the crude material onto a Teledyne ISCO RediSep C18, 5 μm column (10×250 mm) eluted with 0.1 v/v % TFA using a 20-50 v/v % ACN gradient at 18.9 mL/min over 30 min while monitoring absorbance at 214 nm (peptide backbone) and 280 nm (aromatic amino acids). The peak corresponding to the product was collected and pooled from multiple runs, lyophilized, and stored at −20° C. Purified peptidomimetics were reconstituted in water and quantified by UV absorbance at 280 nm to determine isolated yield. Purified peptidomimetics were characterized by LC-MS (FIG. 2) on an Agilent 1200 series HPLC interfaced with an Agilent 1956B LC/MSD SL MSD by injecting peptidomimetics onto an Agilent Zorbax Eclipse XBD-C18 analytical column (4.6×150 cm) eluted at 0.7 mL/min with 0.1 v/v % TFA and an acetonitrile gradient of 5-80 v/v % over 10 minutes. Mass spectral data was obtained in the positive mode. PSVCCK2R-42 MS: 675.9 m/z (M+2H) observed 1349.8, 1350.6 m/z (M+H) observed 1349.6, calculated 1350.9.

A list of control (reference) compounds and CCK2R targeted peptidomimetics developed in the present invention is provided in Table 2. Modifications are described in reference to the formula (3):

(3)

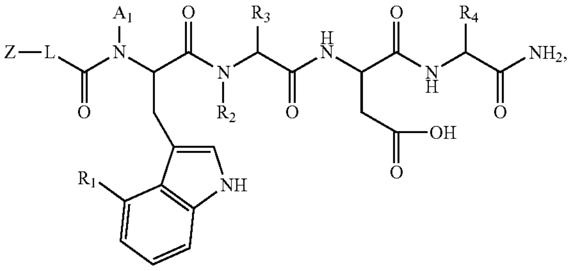

in which text in bold refers to the chelator (Z), text in italic refers to the linker (L), and the remaining structure is the CCK2R targeted peptidomimetic.

TABLE 2

| CCK2R Targeted Peptidomimetics Conjugates | | | | | | | |
|---|---|---|---|---|---|---|---|
| Compound ID | Compound Sequence | SEQ ID NO: | $A_1$ | $R_1$ | $R_2$ | $R_3$ | $R_4$ |
| DOTA-MGS5 | DOTA-dGlu-Ala-Tyr-Gly-Trp-N-Me-Nle-Asp-1-Nal-$NH_2$ | 1 | —H | —H | —$CH_3$ | 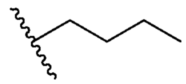 [SMILES: *CCCC] | 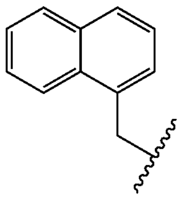 [SMILES: *Cc1cccc2ccccc12] |

TABLE 2-continued

CCK2R Targeted Peptidomimetics Conjugates

| Compound ID | Compound Sequence | SEQ ID NO: | $A_1$ | $R_1$ | $R_2$ | $R_3$ | $R_4$ |
|---|---|---|---|---|---|---|---|
| PSVCCK2R-1 | PSC-dGlu-Ala-Tyr-Gly-Trp-N-Me-Nle-Asp-1-Nal-$NH_2$ | 2 | —H | —H | —$CH_3$ | 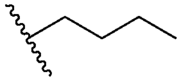 [SMILES: *CCCC] | 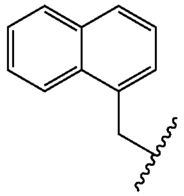 [SMILES: *Cc1cccc2ccccc12] |
| PSVCCK2R-2 | PSC-βAla-βAla-dGlu-Ala-Tyr-Gly-Trp-N-Me-Nle-Asp-1-Nal-$NH_2$ | 3 | —H | —H | —$CH_3$ | 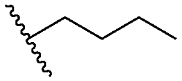 [SMILES: *CCCC] | 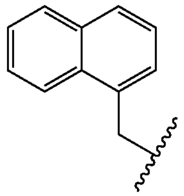 [SMILES: *Cc1cccc2ccccc12] |
| PSVCCK2R-3 | PSC-$PEG_2$-dGlu-Ala-Tyr-Gly-Trp-N-Me-Nle-Asp-1-Nal-$NH_2$ | 4 | —H | —H | —$CH_3$ | 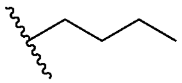 [SMILES: *CCCC] | 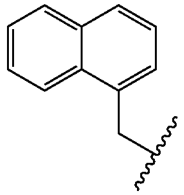 [SMILES: *Cc1cccc2ccccc12] |
| PSVCCK2R-4 | PSC-βAla-Trp-N-Me-Nle-Asp-1-Nal-$NH_2$ | n.a. | —H | —H | —$CH_3$ | 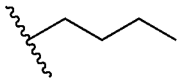 [SMILES: *CCCC] | 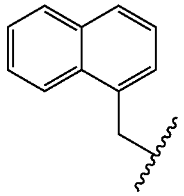 [SMILES: *Cc1cccc2ccccc12] |
| PSVCCK2R-5 | PSC-βAla-βAla-Trp-N-Me-Nle-Asp-1-Nal-$NH_2$ | 5 | —H | —H | —$CH_3$ | 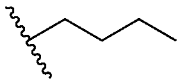 [SMILES: *CCCC] | 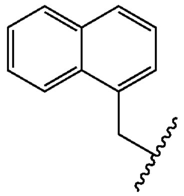 [SMILES: *Cc1cccc2ccccc12] |
| PSVCCK2R-6 | PSC-βAla-βAla-βAla-Trp-N-Me-Nle-Asp-1-Nal-$NH_2$ | 6 | —H | —H | —$CH_3$ | 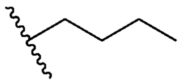 [SMILES: *CCCC] | 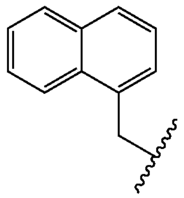 [SMILES: *Cc1cccc2ccccc12] |
| PSVCCK2R-7 | DOTA-βAla-βAla-dGlu-Ala-Tyr-Gly-Trp-N-Me-Nle-Asp-1-Nal-$NH_2$ | 7 | —H | —H | —$CH_3$ | 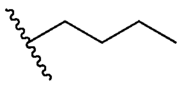 [SMILES: *CCCC] | 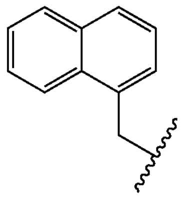 [SMILES: *Cc1cccc2ccccc12] |

TABLE 2-continued

CCK2R Targeted Peptidomimetics Conjugates

| Compound ID | Compound Sequence | SEQ ID NO: | $A_1$ | $R_1$ | $R_2$ | $R_3$ | $R_4$ |
|---|---|---|---|---|---|---|---|
| PSVCCK2R-8 | DOTA-$PEG_2$-dGlu-Ala-Tyr-Gly-Trp-N-Me-Nle-Asp-1-Nal-$NH_2$ | 8 | —H | —H | —$CH_3$ | 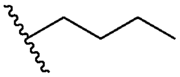 [SMILES: *CCCC] | 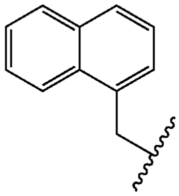 [SMILES: *Cc1cccc2ccccc12] |
| PSVCCK2R-9 | PSC-dGlu-$PEG_2$-dGlu-Ala-Tyr-Gly-Trp-N-Me-Nle-Asp-1-Nal-$NH_2$ | 9 | —H | —H | —$CH_3$ | 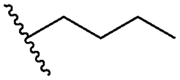 [SMILES: *CCCC] | 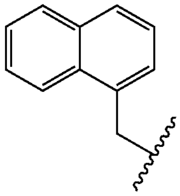 [SMILES: *Cc1cccc2ccccc12] |
| PSVCCK2R-10 | PSC-$PEG_2$-dGlu-Ala-Tyr-Gly-Trp-N-Me-Nle-Asp-2-Nal-$NH_2$ | 10 | —H | —H | —$CH_3$ | 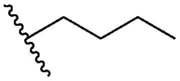 [SMILES: *CCCC] | 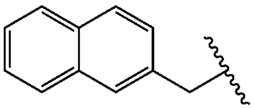 [SMILES: *Cc1ccc2ccccc2c1] |
| PSVCCK2R-11 | PSC-$PEG_2$-dGlu-Ala-Tyr-Gly-Trp(N-Me)-N-Me-Nle-Asp-1-Nal-$NH_2$ | 11 | —H | —H | —$CH_3$ | 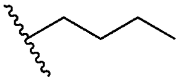 [SMILES: *CCCC] | 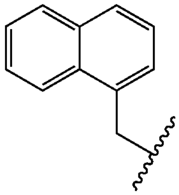 [SMILES: *Cc1cccc2ccccc12] |
| PSVCCK2R-12 | PSC-$PEG_2$-dGlu-Ala-Tyr-Gly-N-Me-Trp-N-Me-Nle-Asp-1-Nal-$NH_2$ | 12 | —$CH_3$ | —H | —$CH_3$ | 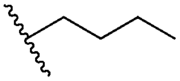 | 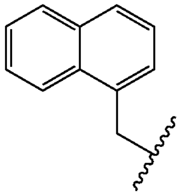 [SMILES: *Cc1cccc2ccccc12] |
| PSVCCK2R-13 | PSC-dGlu-$PEG_2$-Trp-N-Me-Nle-Asp-1-Nal-$NH_2$ | n.a. | —H | —H | —$CH_3$ | 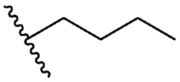 [SMILES: *CCCC] | 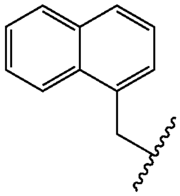 [SMILES: *Cc1cccc2ccccc12] |
| PSVCCK2R-15 | PSC-$PEG_2$-dGlu-Ala(CN)-Tyr-Gly-Trp-N-Me-Nle-Asp-1-Nal-$NH_2$ | 13 | —H | —H | —$CH_3$ | 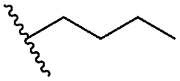 | 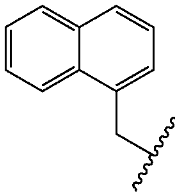 |

TABLE 2-continued

| CCK2R Targeted Peptidomimetics Conjugates | | | | | | | |
|---|---|---|---|---|---|---|---|
| Compound ID | Compound Sequence | SEQ ID NO: | $A_1$ | $R_1$ | $R_2$ | $R_3$ | $R_4$ |
| PSVCCK2R-16 | PSC-$PEG_2$-dGlu-Ala-Phe(5-F)-Gly-Trp-N-Me-Nle-Asp-1-Nal-$NH_2$ | 14 | —H | —H | —$CH_3$ | 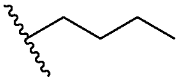 [SMILES: *CCCC] | 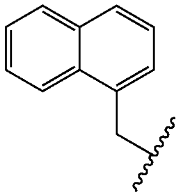 [SMILES: *Cc1cccc2ccccc12] |
| PSVCCK2R-17 | PSC-$PEG_2$-dGlu-Ala-Tyr(3,5-bis-I)-Gly-Trp-N-Me-Nle-Asp-1-Nal-$NH_2$ | 15 | —H | —H | —$CH_3$ | 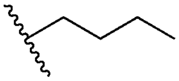 [SMILES: *CCCC] | 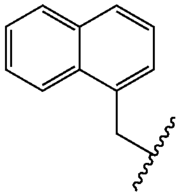 [SMILES: *Cc1cccc2ccccc12] |
| PSVCCK2R-18 | PSC-$PEG_2$-dGlu-Ala-Tyr(3-I)-Gly-Trp-N-Me-Nle-Asp-1-Nal-$NH_2$ | 16 | —H | —H | —$CH_3$ | 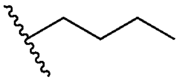 [SMILES: *CCCC] | 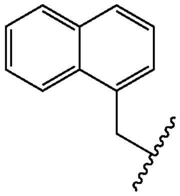 [SMILES: *Cc1cccc2ccccc12] |
| PSVCCK2R-19 | PSC-$PEG_2$-dGlu-Ala-Tyr(3,5-bis-F)-Gly-Trp-N-Me-Nle-Asp-1-Nal-$NH_2$ | 17 | —H | —H | —$CH_3$ | 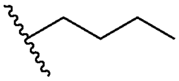 [SMILES: *CCCC] | 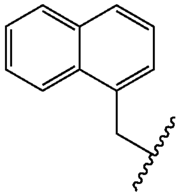 [SMILES: *Cc1cccc2ccccc12] |
| PSVCCK2R-20 | PSC-$PEG_2$-dGlu-Ala-Phe(4-Br)-Gly-Trp-N-Me-Nle-Asp-1-Nal-$NH_2$ | 18 | —H | —H | —$CH_3$ | 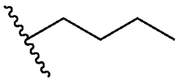 [SMILES: *CCCC] | 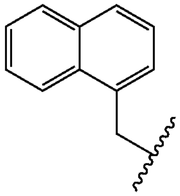 [SMILES: *Cc1cccc2ccccc12] |
| PSVCCK2R-21 | PSC-$(Gabob)_2$-βAla-Trp-N-Me-Nle-Asp-1-Nal-$NH_2$ | n.a. | —H | —H | —$CH_3$ | 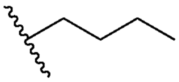 [SMILES: *CCCC] | 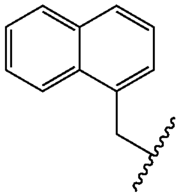 [SMILES: *Cc1cccc2ccccc12] |
| PSVCCK2R-22 | PSC-(Sta)2-βAla-Trp-N-Me-Nle-Asp-1-Nal-$NH_2$ | n.a. | —H | —H | —$CH_3$ | 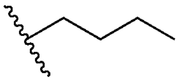 [SMILES: *CCCC] | 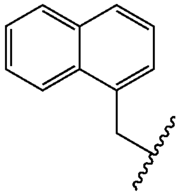 [SMILES: *Cc1cccc2ccccc12] |

TABLE 2-continued

CCK2R Targeted Peptidomimetics Conjugates

| Compound ID | Compound Sequence | SEQ ID NO: | $A_1$ | $R_1$ | $R_2$ | $R_3$ | $R_4$ |
|---|---|---|---|---|---|---|---|
| PSVCCK2R-23 | PSC-(MHA)2-βAla-Trp-N-Me-Nle-Asp-1-Nal-$NH_2$ | n.a. | —H | —H | —$CH_3$ | 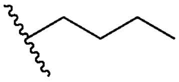 [SMILES: *CCCC] | 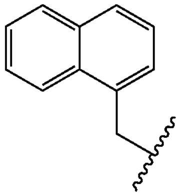 [SMILES: *Cc1cccc2ccccc12] |
| PSVCCK2R-24 | PSC-$PEG_2$-dGlu-Ala-Phe(4-CN)-Gly-Trp-N-Me-Nle-Asp-1-Nal-$NH_2$ | 19 | —H | —H | —$CH_3$ | 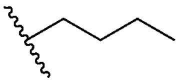 [SMILES: *CCCC] | 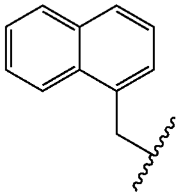 [SMILES: *Cc1cccc2ccccc12] |
| PSVCCK2R-25 | PSC-Sta-βAla-Trp-N-Me-Nle-Asp-1-Nal-$NH_2$ | n.a. | —H | —H | —$CH_3$ | 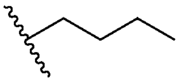 [SMILES: *CCCC] | 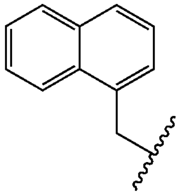 [SMILES: *Cc1cccc2ccccc12] |
| PSVCCK2R-26 | PSC-MHA-βAla-Trp-N-Me-Nle-Asp-1-Nal-$NH_2$ | n.a. | —H | —H | —$CH_3$ | 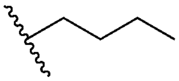 [SMILES: *CCCC] | 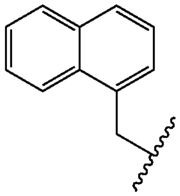 [SMILES: *Cc1cccc2ccccc12] |
| PSVCCK2R-27 | PSC-βGlu-βGlu-βAla-Trp-N-Me-Nle-Asp-1-Nal-$NH_2$ | 20 | —H | —H | —$CH_3$ | 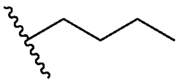 [SMILES: *CCCC] | 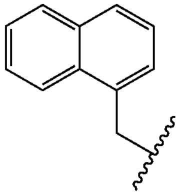 [SMILES: *Cc1cccc2ccccc12] |
| PSVCCK2R-28 | PSC-dGlu-$PEG_2$-Trp(N-Me)-N-Me-Nle-Asp-1-Nal-$NH_2$ | n.a. | —H | —H | —$CH_3$ | 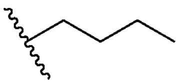 [SMILES: *CCCC] | 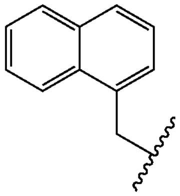 [SMILES: *Cc1cccc2ccccc12] |
| PSVCCK2R-29 | PSC-dGlu-$PEG_2$-bhTrp-N-Me-Nle-Asp-1-Nal-$NH_2$ | n.a. | —H | | —$CH_3$ | 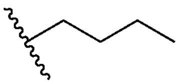 [SMILES: *CCCC] | 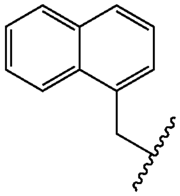 [SMILES: *Cc1cccc2ccccc12] |

TABLE 2-continued

CCK2R Targeted Peptidomimetics Conjugates

| Compound ID | Compound Sequence | SEQ ID NO: | $A_1$ | $R_1$ | $R_2$ | $R_3$ | $R_4$ |
|---|---|---|---|---|---|---|---|
| PSVCCK2R-30 | PSC-dGlu-PEG$_2$-Trp(6-Cl)-N-Me-Nle-Asp-1-Nal-NH$_2$ | n.a. | —H | —H | —$CH_3$ | 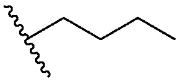 [SMILES: *CCCC] | 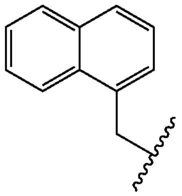 [SMILES: *Cc1cccc2ccccc12] |
| PSVCCK2R-31 | PSC-dGlu-PEG$_2$-Tpi-N-Me-Nle-Asp-1-Nal-NH$_2$ | n.a. | | | —$CH_3$ | 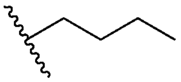 [SMILES: *CCCC] | 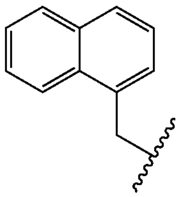 [SMILES: *Cc1cccc2ccccc12] |
| PSVCCK2R-32 | PSC-dGlu-PEG$_2$-Tic-N-Me-Nle-Asp-1-Nal-NH$_2$ | n.a. | | | —$CH_3$ | 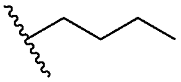 [SMILES: *CCCC] | 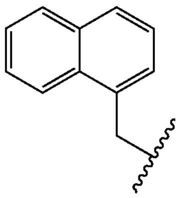 [SMILES: *Cc1cccc2ccccc12] |
| PSVCCK2R-33 | PSC-dGlu-PEG$_2$-Bta-N-Me-Nle-Asp-1-Nal-NH$_2$ | n.a. | H | | —$CH_3$ | 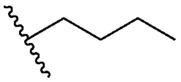 [SMILES: *CCCC] | 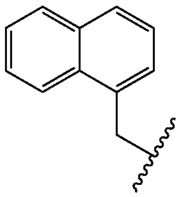 [SMILES: *Cc1cccc2ccccc12] |
| PSVCCK2R-34 | PSC-dGlu-PEG$_2$-Bip-N-Me-Nle-Asp-1-Nal-NH$_2$ | n.a. | H | | —$CH_3$ | 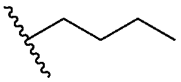 [SMILES: *CCCC] | 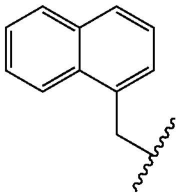 [SMILES: *Cc1cccc2ccccc12] |
| PSVCCK2R-35 | PSC-dGlu-PEG$_2$-Bpa-N-Me-Nle-Asp-1-Nal-NH$_2$ | n.a. | H | | —$CH_3$ | 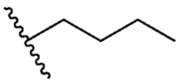 [SMILES: *CCCC] | 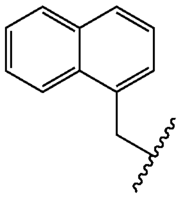 [SMILES: *Cc1cccc2ccccc12] |
| PSVCCK2R-36 | PSC-dGlu-PEG$_2$-Ala(4-Pyr)-N-Me-Nle-Asp-1-Nal-NH$_2$ | n.a. | H | | —$CH_3$ | 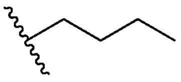 [SMILES: *CCCC] | 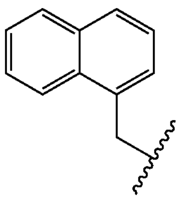 [SMILES: *Cc1cccc2ccccc12] |

TABLE 2-continued

CCK2R Targeted Peptidomimetics Conjugates

| Compound ID | Compound Sequence | SEQ ID NO: | $A_1$ | $R_1$ | $R_2$ | $R_3$ | $R_4$ |
|---|---|---|---|---|---|---|---|
| PSVCCK2R-37 | PSC-dGlu-PEG$_2$-Ala(3-Pyr)-N-Me-Nle-Asp-1-Nal-NH$_2$ | n.a. | H | | —CH$_3$ | 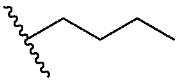 [SMILES: *CCCC] | 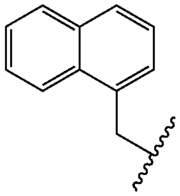 [SMILES: *Cc1cccc2ccccc12] |
| PSVCCK2R-38 | PSC-dGlu-PEG$_2$-Tyr(3-F)-N-Me-Nle-Asp-1-Nal-NH$_2$ | n.a. | H | | —CH$_3$ | 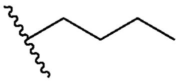 [SMILES: *CCCC] | 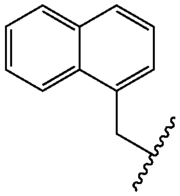 [SMILES: *Cc1cccc2ccccc12] |
| PSVCCK2R-39 | PSC-dGlu-PEG$_2$-Trp(6-OMe)-N-Me-Nle-Asp-1-Nal-NH$_2$ | n.a. | —H | —H | —CH$_3$ | 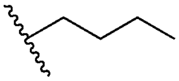 [SMILES: *CCCC] | 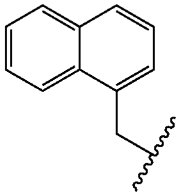 [SMILES: *Cc1cccc2ccccc12] |
| PSVCCK2R-40 | PSC-dGlu-PEG$_2$-1-Nal-N-Me-Nle-Asp-1-Nal-NH$_2$ | n.a. | —H | | —CH$_3$ | 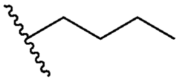 [SMILES: *CCCC] | 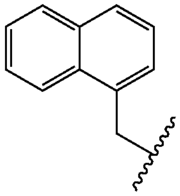 [SMILES: *Cc1cccc2ccccc12] |
| PSVCCK2R-41 | PSC-dGlu-PEG$_2$-2-Nal-N-Me-Nle-Asp-1-Nal-NH$_2$ | n.a. | —H | | —CH$_3$ | 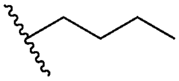 [SMILES: *CCCC] | 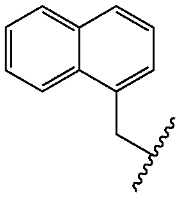 [SMILES: *Cc1cccc2ccccc12] |
| PSVCCK2R-42 | PSC-dGlu-PEG$_2$-Trp(4-Cl)-N-Me-Nle-Asp-1-Nal-NH$_2$ | n.a. | —H | —Cl | —CH$_3$ | 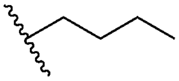 [SMILES: *CCCC] | 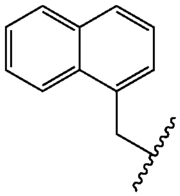 [SMILES: *Cc1cccc2ccccc12] |
| PSVCCK2R-43 | PSC-dGlu-PEG$_4$-Trp-N-Me-Nle-Asp-1-Nal-NH$_2$ | n.a. | —H | —H | —CH$_3$ | 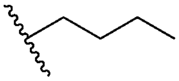 [SMILES: *CCCC] | 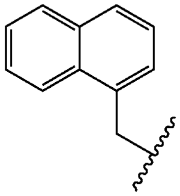 [SMILES: *Cc1cccc2ccccc12] |

TABLE 2-continued

CCK2R Targeted Peptidomimetics Conjugates

| Compound ID | Compound Sequence | SEQ ID NO: | $A_1$ | $R_1$ | $R_2$ | $R_3$ | $R_4$ |
|---|---|---|---|---|---|---|---|
| PSVCCK2R-44 | PSC-dGlu-PEG$_2$-Trp(5-CN)-N-Me-Nle-Asp-1-Nal-NH$_2$ | n.a. | —H | —H | —$CH_3$ | 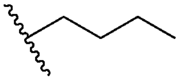 [SMILES: *CCCC] | 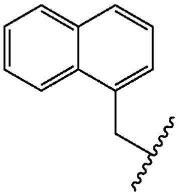 [SMILES: *Cc1cccc2ccccc12] |
| PSVCCK2R-45 | PSC-dGlu-PEG$_2$-Trp-N-Me-Nle-Glu-1-Nal-NH$_2$ | n.a. | —H | —H | — $CH_3$ | 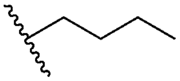 [SMILES: *CCCC] | 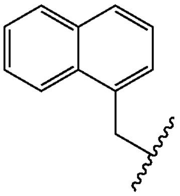 [SMILES: *Cc1cccc2ccccc12] |
| PSVCCK2R-46 | PSC-dGlu-PEG$_2$-Trp-N-Me-Nle-Gla-1-Nal-NH$_2$ | n.a. | —H | —H | —$CH_3$ | 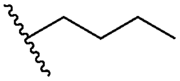 [SMILES: *CCCC] | 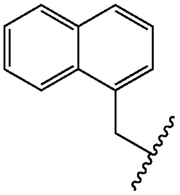 [SMILES: *Cc1cccc2ccccc12] |
| PSVCCK2R-47 | PSC-dGlu-PEG$_2$-IGL-N-Me-Nle-Asp-1-Nal-NH$_2$ | n.a. | H | | —$CH_3$ | 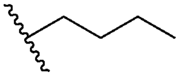 [SMILES: *CCCC] | 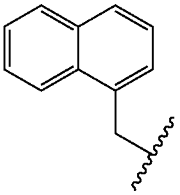 [SMILES: *Cc1cccc2ccccc12] |
| PSVCCK2R-48 | PSC-dGlu-PEG$_2$-Trp-N-Me-Nle-a-Me-Glu-1-Nal-NH$_2$ | n.a. | —H | —H | —$CH_3$ | 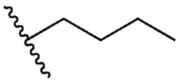 [SMILES: *CCCC] | 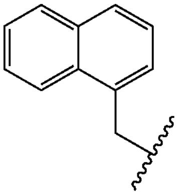 [SMILES: *Cc1cccc2ccccc12] |
| PSVCCK2R-49 | PSC-dGlu-PEG$_2$-Trp-N-Me-Nle(6-OH)-Asp-1-Nal-NH$_2$ | n.a. | —H | —H | —$CH_3$ | 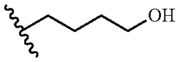 [SMILES: *CCCCO] | 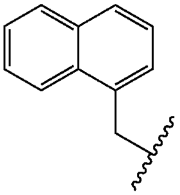 [SMILES: *Cc1cccc2ccccc12] |
| PSVCCK2R-50 | PSC-dGlu-PEG$_2$-Trp-N-Me-Nle(6-O-Bz)-Asp-1-Nal-NH$_2$ | n.a. | —H | —H | —$CH_3$ | 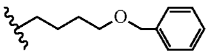 | 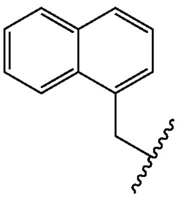 [SMILES: *Cc1cccc2ccccc12] |

TABLE 2-continued

| CCK2R Targeted Peptidomimetics Conjugates | | | | | | | |
|---|---|---|---|---|---|---|---|
| Compound ID | Compound Sequence | SEQ ID NO: | $A_1$ | $R_1$ | $R_2$ | $R_3$ | $R_4$ |
| PSVCCK2R-51 | PSC-dGlu-$PEG_2$-Trp-N-Me-Ala(cyclohexyl)-Asp-1-Nal-$NH_2$ | n.a. | —H | —H | —$CH_3$ | 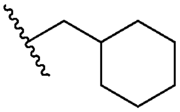 [SMILES: *CC1CCCCC1] | 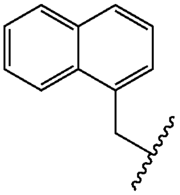 [SMILES: *Cc1cccc2ccccc12] |
| PSVCCK2R-52 | PSC-dGlu-$PEG_2$-Trp-N-Me-Ala(beta-cyclobutyl)-Asp-1-Nal-$NH_2$ | n.a. | —H | —H | —$CH_3$ | 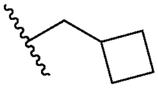 [SMILES: *CC1CCC1] | 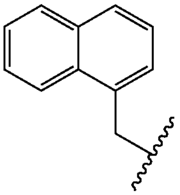 [SMILES: *Cc1cccc2ccccc12] |
| PSVCCK2R-53 | PSC-dGlu-$PEG_2$-Trp-N-Me-Ala(cyclopentyl)-Asp-1-Nal-$NH_2$ | n.a. | —H | —H | —$CH_3$ | 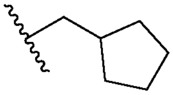 [SMILES: *CC1CCCC1] | 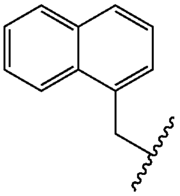 [SMILES: *Cc1cccc2ccccc12] |
| PSVCCK2R-54 | PSC-dGlu-$PEG_2$-Trp-N-Me-Nle(5,5-DiMe)-Asp-1-Nal-$NH_2$ | n.a. | —H | —H | —$CH_3$ | 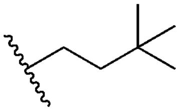 [SMILES: *CCC(C)(C)C] | 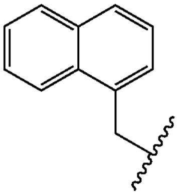 [SMILES: *Cc1cccc2ccccc12] |
| PSVCCK2R-55 | PSC-dGlu-$PEG_2$-Trp-N-Me-Nle-Aad-1-Nal-$NH_2$ | n.a. | —H | —H | —$CH_3$ | 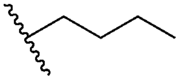 [SMILES: *CCCC] | 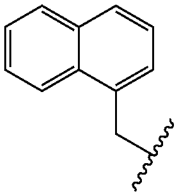 [SMILES: *Cc1cccc2ccccc12] |
| PSVCCK2R-56 | PSC-dGlu-$PEG_2$-Trp-N-Me-Nle-Asu-1-Nal-$NH_2$ | n.a. | —H | —H | —$CH_3$ | 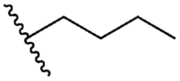 [SMILES: *CCCC] | 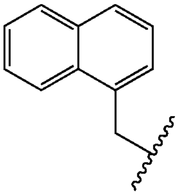 [SMILES: *Cc1cccc2ccccc12] |
| PSVCCK2R-57 | DOTA-dGlu-$PEG_4$-Trp-N-Me-Nle-Asp-1-Nal-$NH_2$ | n.a. | —H | —H | —$CH_3$ | 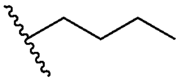 [SMILES: *CCCC] | 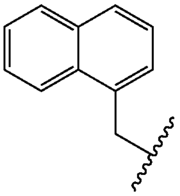 [SMILES: *Cc1cccc2ccccc12] |

TABLE 2-continued

| CCK2R Targeted Peptidomimetics Conjugates | | | | | | | |
|---|---|---|---|---|---|---|---|
| Compound ID | Compound Sequence | SEQ ID NO: | $A_1$ | $R_1$ | $R_2$ | $R_3$ | $R_4$ |
| PSVCCK2R-58 | PSC-dGlu-Trp-N-Me-Nle-Asp-1-Nal-$NH_2$ | n.a. | —H | —H | —$CH_3$ | 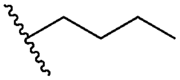 [SMILES: *CCCC] | 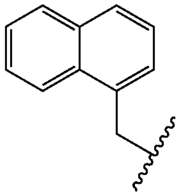 [SMILES: *Cc1cccc2ccccc12] |
| PSVCCK2R-59 | PSC-dGlu-$(Gabob)_2$-Trp-N-Me-Nle-Asp-1-Nal-$NH_2$ | n.a. | —H | —H | —$CH_3$ | 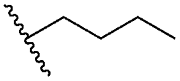 [SMILES: *CCCC] | 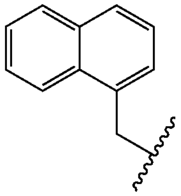 [SMILES: *Cc1cccc2ccccc12] |
| PSVCCK2R-60 | PSC-dGlu-$PEG_2$-Trp(4-Aza)-N-Me-Nle-Asp-1-Nal-$NH_2$ | n.a. | H | | —$CH_3$ | 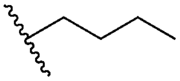 [SMILES: *CCCC] | 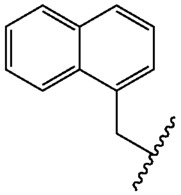 [SMILES: *Cc1cccc2ccccc12] |
| PSVCCK2R-61 | PSC-dGlu-$PEG_2$-Trp(7-Aza)-N-Me-Nle-Asp-1-Nal-$NH_2$ | n.a. | H | | —$CH_3$ | 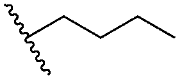 [SMILES: *CCCC] | 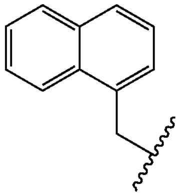 [SMILES: *Cc1cccc2ccccc12] |
| PSVCCK2R-62 | PSC-dGlu-$PEG_2$-Ala(3-Pry)-N-Me-Nle-Asp-1-Nal-$NH_2$ | n.a. | H | | —$CH_3$ | 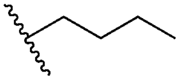 [SMILES: *CCCC] | 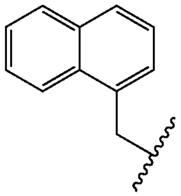 [SMILES: *Cc1cccc2ccccc12] |
| PSVCCK2R-63 | PSC-dGlu-$PEG_2$-Trp(5-Cl) -N-Me-Nle-Asp-1-Nal-$NH_2$ | n.a. | —H | —H | —$CH_3$ | 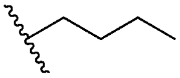 | 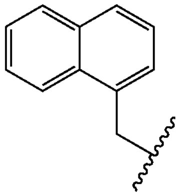 [SMILES: *Cc1cccc2ccccc12] |
| PSVCCK2R-64 | PSC-dGlu-$PEG_2$-Trp(2-Me)-N-Me-Nle-Asp-1-Nal-$NH_2$ | n.a. | —H | —H | —$CH_3$ | 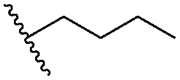 [SMILES: *CCCC] | 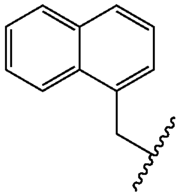 [SMILES: *Cc1cccc2ccccc12] |

TABLE 2-continued

| CCK2R Targeted Peptidomimetics Conjugates | | | | | | | |
|---|---|---|---|---|---|---|---|
| Compound ID | Compound Sequence | SEQ ID NO: | $A_1$ | $R_1$ | $R_2$ | $R_3$ | $R_4$ |
| PSVCCK2R-65 | PSC-dGlu-PEG$_2$-Trp(4-CN)-N-Me-Nle-Asp-1-Nal-NH$_2$ | n.a. | —H | —CN | —$CH_3$ | 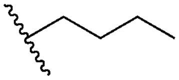 [SMILES: *CCCC] | 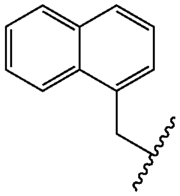 [SMILES: *Cc1cccc2ccccc12] |
| PSVCCK2R-66 | PSC-dGlu-PEG$_2$-Trp(4-Me)-N-Me-Nle-Asp-1-Nal-NH$_2$ | n.a. | —H | —$CH_3$ | —$CH_3$ | 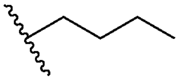 [SMILES: *CCCC] | 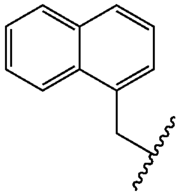 [SMILES: *Cc1cccc2ccccc12] |
| PSVCCK2R-67 | PSC-dGlu-PEG$_2$-Trp(4-Br)-N-Me-Nle-Asp-1-Nal-NH$_2$ | n.a. | —H | —Br | —$CH_3$ | 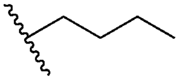 [SMILES: *CCCC] | 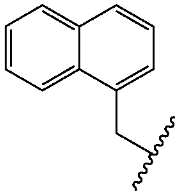 [SMILES: *Cc1cccc2ccccc12] |
| PSVCCK2R-68 | PSC-dGlu-PEG$_2$-Trp(4-Cl)-Trp(4-Cl)-N-Me-Nle-Asp-1-Nal-NH$_2$ | n.a. | —H | —Cl | —$CH_3$ | 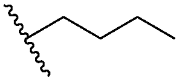 [SMILES: *CCCC] | 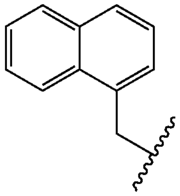 [SMILES: *Cc1cccc2ccccc12] |
| PSVCCK2R-69 | PSC-dGlu-PEG$_2$-Trp-Nle(6-OH)-Asp-1-Nal-NH$_2$ | n.a. | —H | —H | —H | 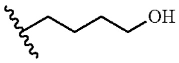 [SMILES: *CCCCO] | 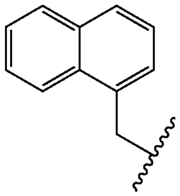 [SMILES: *Cc1cccc2ccccc12] |
| PSVCCK2R-70 | PSC-dGlu-PEG$_2$-Trp(4-F)-N-Me-Nle-Asp-1-Nal-NH$_2$ | n.a. | —H | —F | —$CH_3$ | 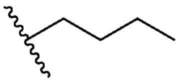 [SMILES: *CCCC] | 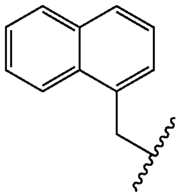 [SMILES: *Cc1cccc2ccccc12] |
| PSVCCK2R-71 | PSC-dGlu-PEG$_2$-Trp-N-Me-Nle-Asp-bh-1-Nal-NH$_2$ | n.a. | —H | —H | —$CH_3$ | 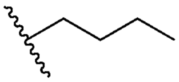 [SMILES: *CCCC] | 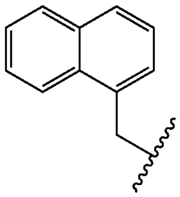 [SMILES: *Cc1cccc2ccccc12] |

TABLE 2-continued

CCK2R Targeted Peptidomimetics Conjugates

| Compound ID | Compound Sequence | SEQ ID NO: | $A_1$ | $R_1$ | $R_2$ | $R_3$ | $R_4$ |
| --- | --- | --- | --- | --- | --- | --- | --- |
| PSVCCK2R-72 | PSC-dGlu-$PEG_2$-Trp(4-CN)-N-Me-Ala(cyclopentyl)-Asp-1-Nal-$NH_2$ | n.a. | —H | —CN | —$CH_3$ | 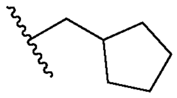 [SMILES: *CC1CCCC1] | 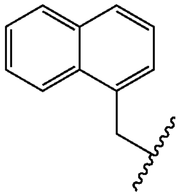 [SMILES: *Cc1cccc2ccccc12] |
| PSVCCK2R-73 | PSC-dGlu-$PEG_2$-Trp(4-Br)-N-Me-Ala(cyclopentyl)-Asp-1-Nal-$NH_2$ | n.a. | — H | —Br | —$CH_3$ | 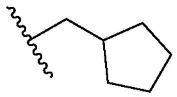 [SMILES: *CC1CCCC1] | 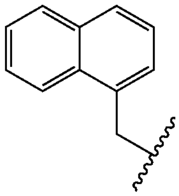 [SMILES: *Cc1cccc2ccccc12] |
| PSVCCK2R-74 | PSC-dGlu-$PEG_2$-Trp(4-OH)-N-Me-Nle-Asp-1-Nal-$NH_2$ | n.a. | —H | —OH | —$CH_3$ | 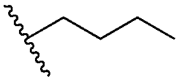 [SMILES: *CCCC] | 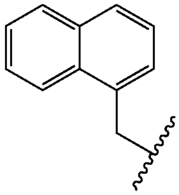 [SMILES: *Cc1cccc2ccccc12] |
| PSVCCK2R-75 | PSC-dGlu-$PEG_2$-Trp(4-OMe)-N-Me-Nle-Asp-1-Nal-$NH_2$ | n.a. | —H | —$OCH_3$ | —$CH_3$ | 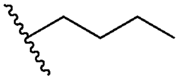 [SMILES: *CCCC] | 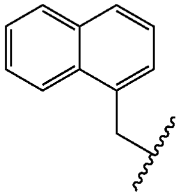 [SMILES: *Cc1cccc2ccccc12] |
| PSVCCK2R-76 | PSC-dGlu-$PEG_2$-Trp(4-Cl)-N-Me-Ala(cyclopentyl)-Asp-1-Nal-$NH_2$ | n.a. | —H | —Cl | —$CH_3$ | 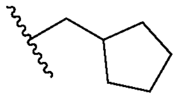 [SMILES: *CC1CCCC1] | 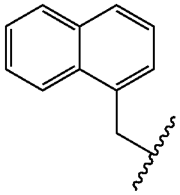 [SMILES: *Cc1cccc2ccccc12] |
| PSVCCK2R-77 | PSC-dGlu-$PEG_2$-Trp(4-I)-N-Me-Nle-Asp-1-Nal-$NH_2$ | n.a. | —H | —I | —$CH_3$ | 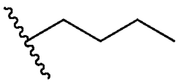 | 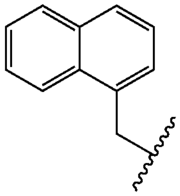 [SMILES: *Cc1cccc2ccccc12] |
| PSVCCK2R-78 | PSC-dGlu-$PEG_2$-Trp(4-$NO_2$)-N-Me-Nle-Asp-1-Nal-$NH_2$ | n.a. | —H | —$NO_2$ | —$CH_3$ | 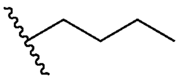 [SMILES: *CCCC] | 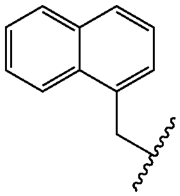 [SMILES: *Cc1cccc2ccccc12] |

TABLE 2-continued

CCK2R Targeted Peptidomimetics Conjugates

| Compound ID | Compound Sequence | SEQ ID NO: | $A_1$ | $R_1$ | $R_2$ | $R_3$ | $R_4$ |
|---|---|---|---|---|---|---|---|
| PSVCCK2R-79 | PSC-dGlu-$PEG_2$-Trp(4-I)-N-Me-Ala(cyclopentyl)-Asp-1-Nal-$NH_2$ | n.a. | —H | —I | —$CH_3$ | 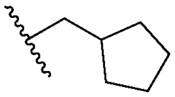 [SMILES: *CC1CCCC1] | 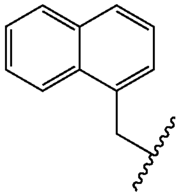 [SMILES: *Cc1cccc2ccccc12] |
| PSVCCK2R-80 | PSC-dGlu-$PEG_2$-Trp(4-$NO_2$)-N-Me-Ala (cyclopentyl)-Asp-1-Nal-$NH_2$ | n.a. | —H | —$NO_2$ | —$CH_3$ | 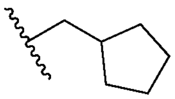 | 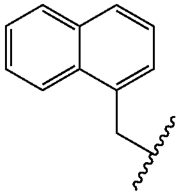 [SMILES: *Cc1cccc2ccccc12] |
| PSVCCK2R-81 | DOTA-dGlu-$PEG_2$-Trp(4-Cl)-N-Me-Nle-Asp-1-Nal-$NH_2$ | n.a. | —H | —Cl | —$CH_3$ | 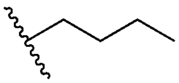 [SMILES: *CCCC] | 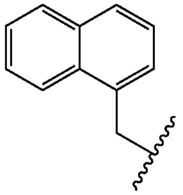 [SMILES: *Cc1cccc2ccccc12] |
| PSVCCK2R-82 | PSC-dGlu-$PEG_2$-Trp(4-$CONH_2$)-N-Me-Nle-Asp-1-Nal-$NH_2$ | n.a. | —H | —$CONH_2$ | —$CH_3$ | 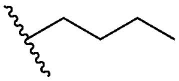 [SMILES: *CCCC] | 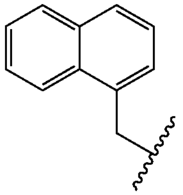 [SMILES: *Cc1cccc2ccccc12] |

Abbreviations:

ac = acetylated n-terminus

Aad = alpha-aminoadipic acid

βAla = β-alanine

6AHA = 6 aminohexanoic acid

12-Ado = 12-aminododecanoic acid

Asu = (S)-2-amino-suberic acid bh-1-Nal = (S)-3-amino-4-(1-naphthyl)butanoic acid MHA = (4R,5S)-4-amino-5-methyl-heptanoic acid Sta = ((35,4S)-4-amino)-3-hydroxy-6-methylheptanoic acid Gabob = 4-amino-3-hydroxybutyric acid Gla = (S)-3-aminopropane-1,1,3-tricarboxylic acid IGL = L-2-indanylglycine bHTrp = L-beta-homotryptophan N-Me-Trp = N-methyl-tryptophan Trp(6-Cl) = Trp(6-choloro)

Tpi = L-1,2,3,4-Tetrahydronorharman-3-carboxylic acid

Tic = L-1,2,3,4-tetrahydroisoquinoline-3-carboxylic acid

Bta = (3-benzothienyl)-L-alanine

Trp(6-OMe) = Trp(6-O-Methyl)

n.a.: not applicable due to less than 4 specifcally defined amino acids under the WIPO standard ST.26

The following examples are provided to further illustrate certain aspects of the present disclosure. These examples are illustrative only and are not intended to limit the scope of the disclosure in any way.

EXAMPLES

Example 1

Materials

A431 human epidermoid carcinoma cells wild type (Cat #KC-0273-DW, not for sale) and stably transfected with human CCKBR gene (A431-CCK2R) were purchased from KYINNO Biotechnology (Cat #KC-3521) and used for all the in vitro and in vivo studies. A431 cells were cultured in DMEM medium supplemented with 10% FBS and 1% penicillin/streptomycin and used for internal control with negative CCK2R expression, and A431-CCK2R cells in DMEM medium supplemented with 10% FBS and 1 μg/mL Puromycin at 37° C. under a humidified condition (5% $CO_2$). [$^{125}$I] (3-iodo-Try$^{12}$, Leu$^{15}$) human gastrin-1 ($^{125}$I-gastrin-1) was purchased from ViTrax (CA, USA) and used for the competitive binding assay. RPMI 1640 medium was supplemented with 0.2% BSA, 25 mM HEPES buffer and 0.3 mM 1,10-phenanthroline and used as binding medium for in vitro assays. All the related chemicals and reagents used for radiolabeling were at trace-metal level and should be HPLC grade.

Radiolabeling CCK2R Targeted Peptidomimetic with Lead-203

$^{203}PbCl_2$ was provided by the University of Alberta (Edmonton, Canada) or Department of Energy through the University of Alabama. The procedure for $^{203}$Pb purification and radiolabeling was established as described in previous publication [1]. In general, approximate 18.5 MBq of purified $^{203}PbCl_2$ was added to the precursor mixture containing 3 nmol of CCK2R targeted peptidomimetic compound and 2 mg/ml of sodium ascorbate in sodium acetate buffer at final pH of 5.3-5.4 for the radiolabeling reaction at 80° C. for 20 min. At the end of synthesis (EOS), the radiochemical yield was >97% and the molar activity of the $^{203}$Pb-labeled CCK2R targeted peptidomimetic was 5.55-6.66 MBq/nmol. The radiolabeled peptidomimetic conjugates were used for in vitro binding or in vivo biodistribution studies.

Radiochemical Purity and Stability

Radiochemical purity (RCP) was determined by iTLC and Radio-HPLC. At EOS, 0.5-1 μL of reaction mixture or $^{203}PbCl_2$ was applied to silica gel strip (2 cm×12 cm) (Agilent, CA) and air-dried for 1-2 min at RT. iTLC strip was developed under mobile phase of 0.1 M sodium citrate for 7 min and the strip was cut in the middle and the top and bottom half strip were counted by the gamma counter. The RCP was calculated as the percentage of the counts from the bottom half strip to the total counts from both the top and bottom halves. Radio-HPLC analysis was conducted on Thermo Scientific Dionex UltiMate 3000 system with a flow-through 105-S model radioactive detector (Corroll & Ramsey, Fort Collin, CO, USA). Binary mobile phases were 5-60% mobile phase B (acetonitrile) over phase A (0.1% TFA in water) over 10 min on Agilent Eclipse XD8-C18 column (4.6×150 mm, 5 μm). Approximate 74-185 kBq of reaction mixture EOS were prepared in ~50-200 UL of HPLC-grade water and injected for HPLC analysis. For stability evaluation, 50-70 μL of radiolabeled peptidomimetic conjugate was added to 0.5 mL of human serum (H4552, SLC19015, Sigma Aldrich) and incubated on the mixer at 37° C. for 20-24 hours. At the end of incubation, serum samples were deproteinated by adding 1.5 volumes of ice-cold acetonitrile and precipitated at 12,000 rpm at 4° C. for 10 min. The supernatant was collected, and another 1 volume of ice-cold acetonitrile was added for precipitation. Approximate 74-185 kBq of the supernatant was diluted using HPLC-grade water to final 200 μL for Radio-HPLC analysis. RCP was determined by the percentage of peak area of the $^{203}$Pb-labeled peptidomimetic by the retention time to the total area of all radio-peaks.

In Vitro Competitive Binding Assay

A431-CCK2R cells were plated into poly-D-lysine-coated 24-well plates (Corning, Cat #356414) at a density of 1.0×10$^5$ cells per well. On day 3, cells at ~80-90% confluence were incubated with $^{125}$I-gastrin-1 (~20,000 CPM) radiotracer and increasing concentrations of CCK2R peptidomimetic conjugates ($10^{-12}$ to $10^{-6}$ M) in binding medium at 37° C. for 2 hours. Cells were then washed twice with ice-cold PBS and cell lysates were collected with 1 mL of 0.5 N NaOH for gamma-counting using an automated gamma counter (PerkinElmer Cobra II; PerkinElmer, Freemont, CA). $IC_{50}$ was determined by nonlinear regression using GraphPad Prism V10 software. The assay was repeated at least 2 times with duplicates of each concentration for each analyte.

Cellular Uptake of $^{203}$Pb-Labeled Peptidomimetics

For the uptake study, A431-CCK2R cells were plated at a density of 1.0×10$^5$ cells/well into poly-D-lysine coated 24-well plate 2-3 days prior to the experiment reaching 80-90% confluence. Cells were incubated with $^{203}$Pb-labeled CCK2R targeted peptidomimetics (~100,000 CPM) in the binding medium for up to 2 hours. Cells were washed two times with cold binding buffer to remove unbound tracer and lysed with 1 mL of 0.5 N NaOH. Cell lysates were collected for gamma-counting. The binding specificity was confirmed by co-incubating the radiolabeled peptidomimetics with an excess amount of cold peptidomimetics at 100 nM. Total uptake of $^{203}$Pb-labeled CCK2R targeted peptidomimetics was presented as the percent of the gamma counts from the cell lysate to the total radiotracer input. The assay was repeated at least 2 times with duplicates for each time point of each analyte.

In Vivo Biodistribution of $^{203}$Pb-Labeled CCK2R Targeted Peptidomimetics

All animal experiments were performed according to the guidelines set by NIH and the animal protocols approved by the IACUC at the University of Iowa. For the biodistribution studies female athymic nu/nu mice (4-6 weeks old) were inoculated with A431-CCK2R cells (2.0×10$^6$ cells/animal) subcutaneously. About 3-4 weeks post inoculation when the tumor xenograft reached ~6-10 mm in any direction, 37-74 kBq of $^{203}$Pb-labeled CCK2R targeted peptidomimetics (molar activity: 5.55-6.66 MBq/nmol) was injected into the tumor-bearing mice via tail vein. To determine the specific CCK2R receptor-mediated tumor targeting mechanism, excess mass of unlabeled peptidomimetics (20 nmol) was co-injected with the $^{203}$Pb-labeled peptidomimetics into mice. At 4 hours and 24 hours post injection, mice were euthanized following the animal protocol and blood, major organs and tissues were collected, weighed and gamma counted. The samples were analyzed and decay-corrected by the reference doses to determine the percentage of injected dose per gram of weight (% ID/g).

Example 2

Figure 4:
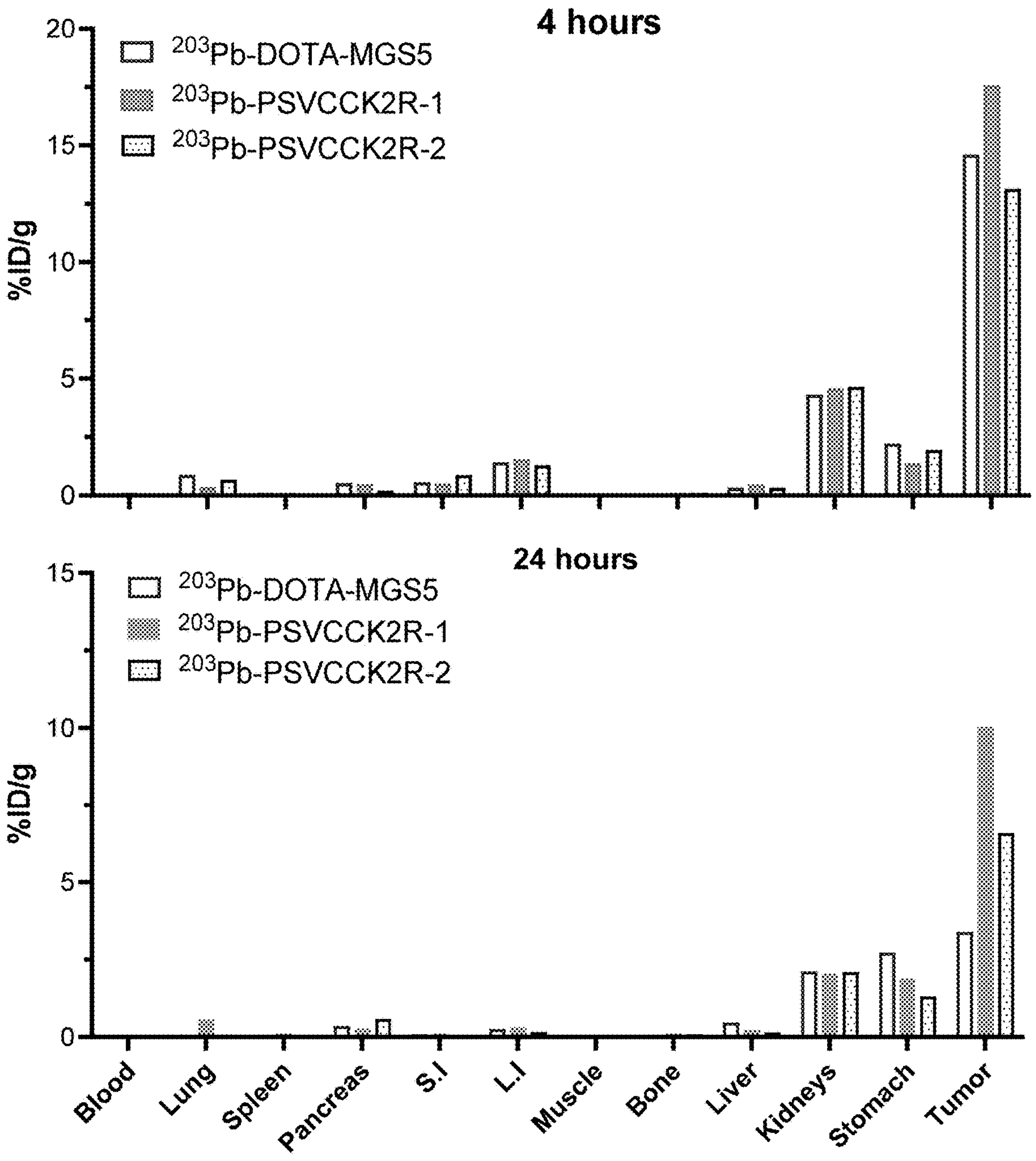
FIG. 4 shows the biodistribution of $^{203}$Pb-labeled CCK2R targeted peptidomimetic conjugates in mice bearing A431-CCK2R xenograft.
Figure 4:
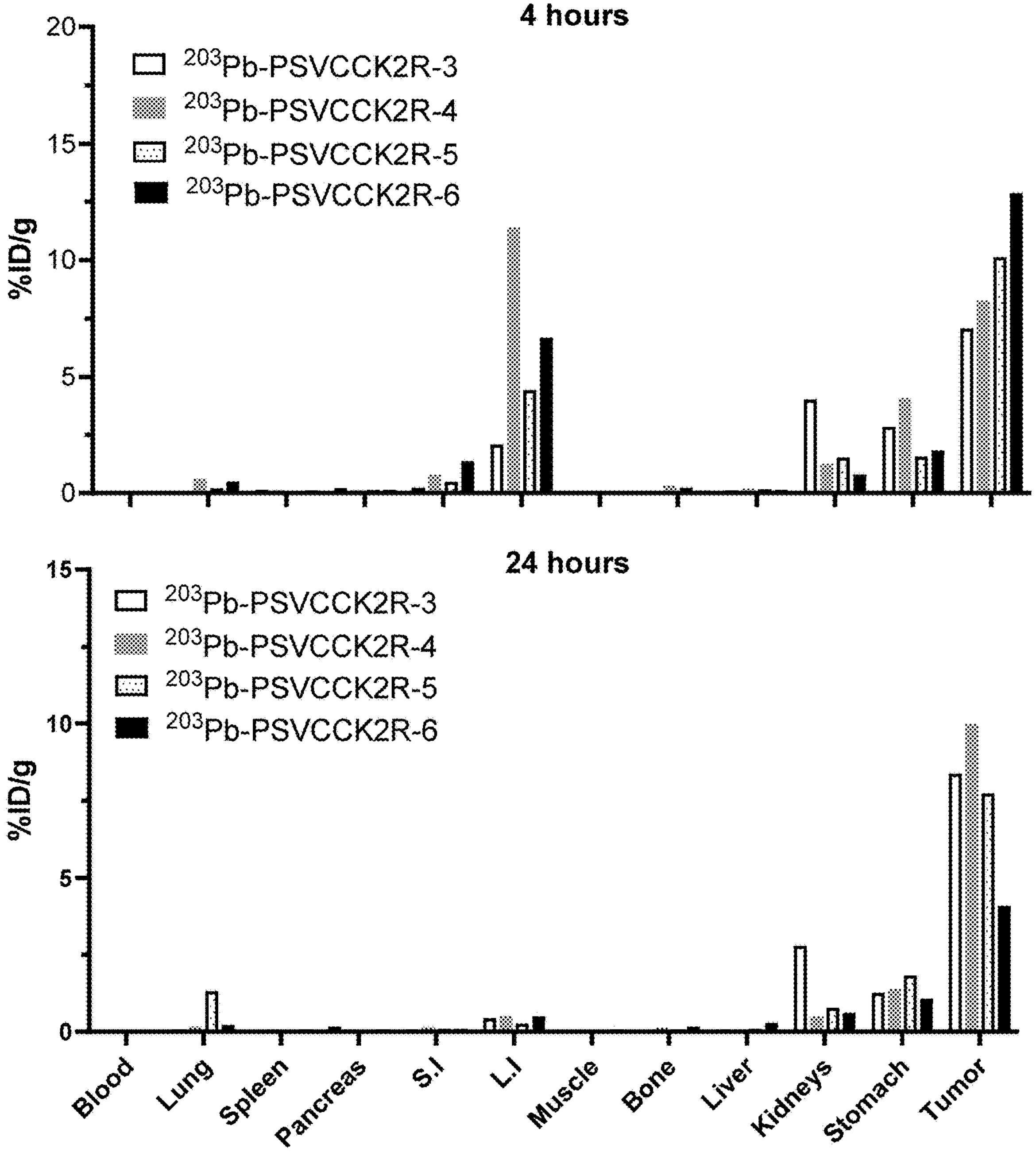
Figure 4:
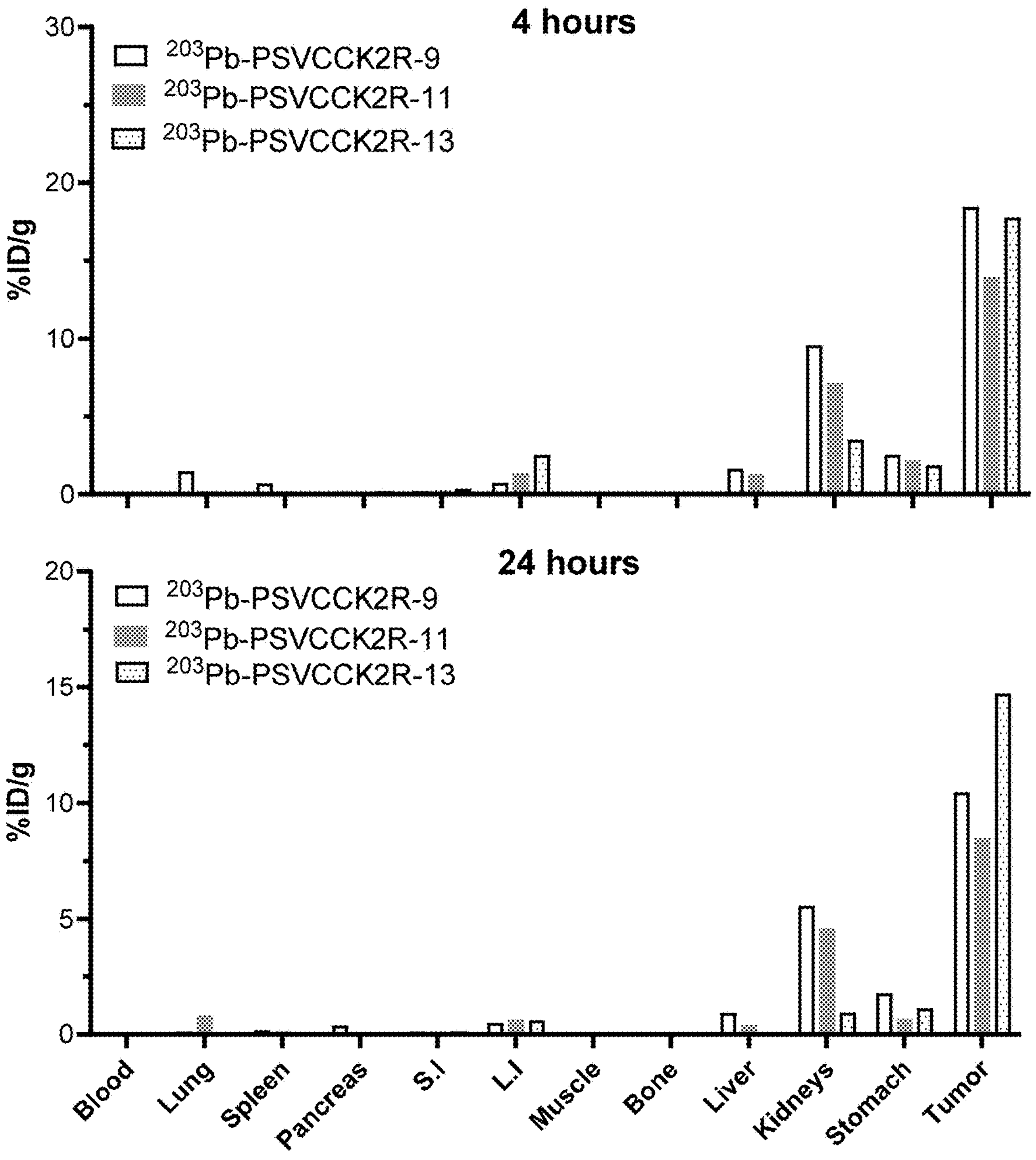
Figure 4:
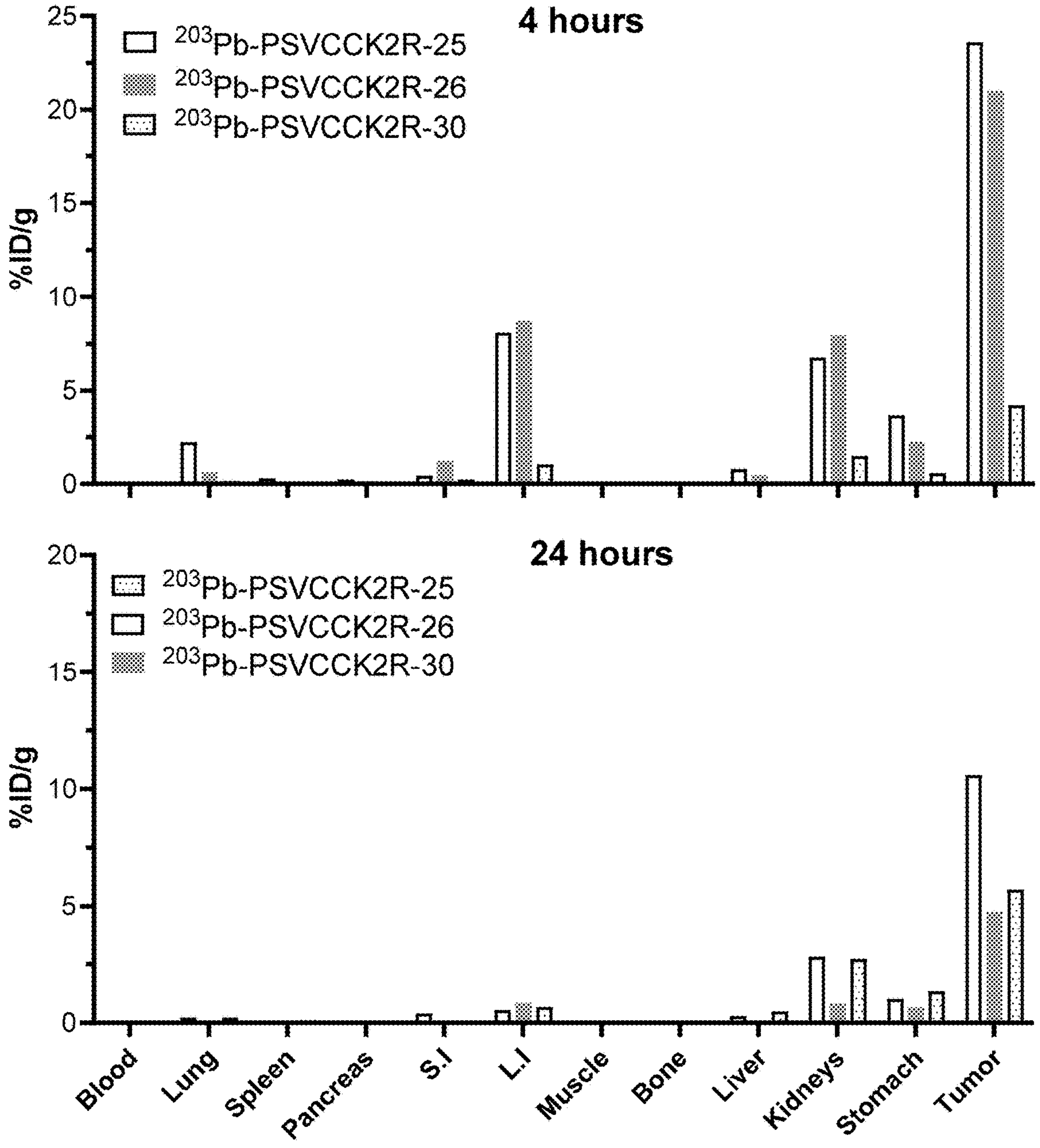
Figure 4:
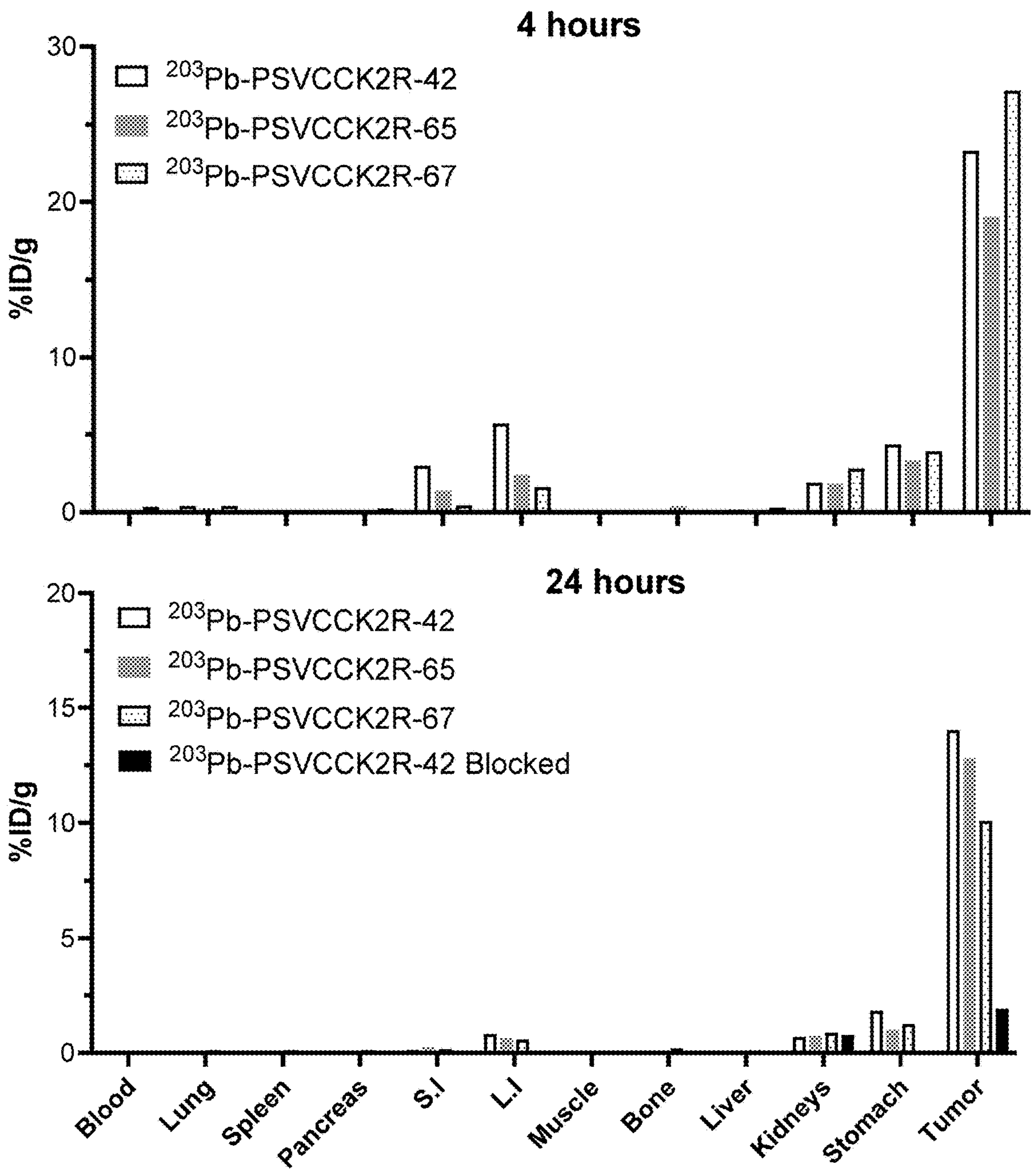
Figure 4:
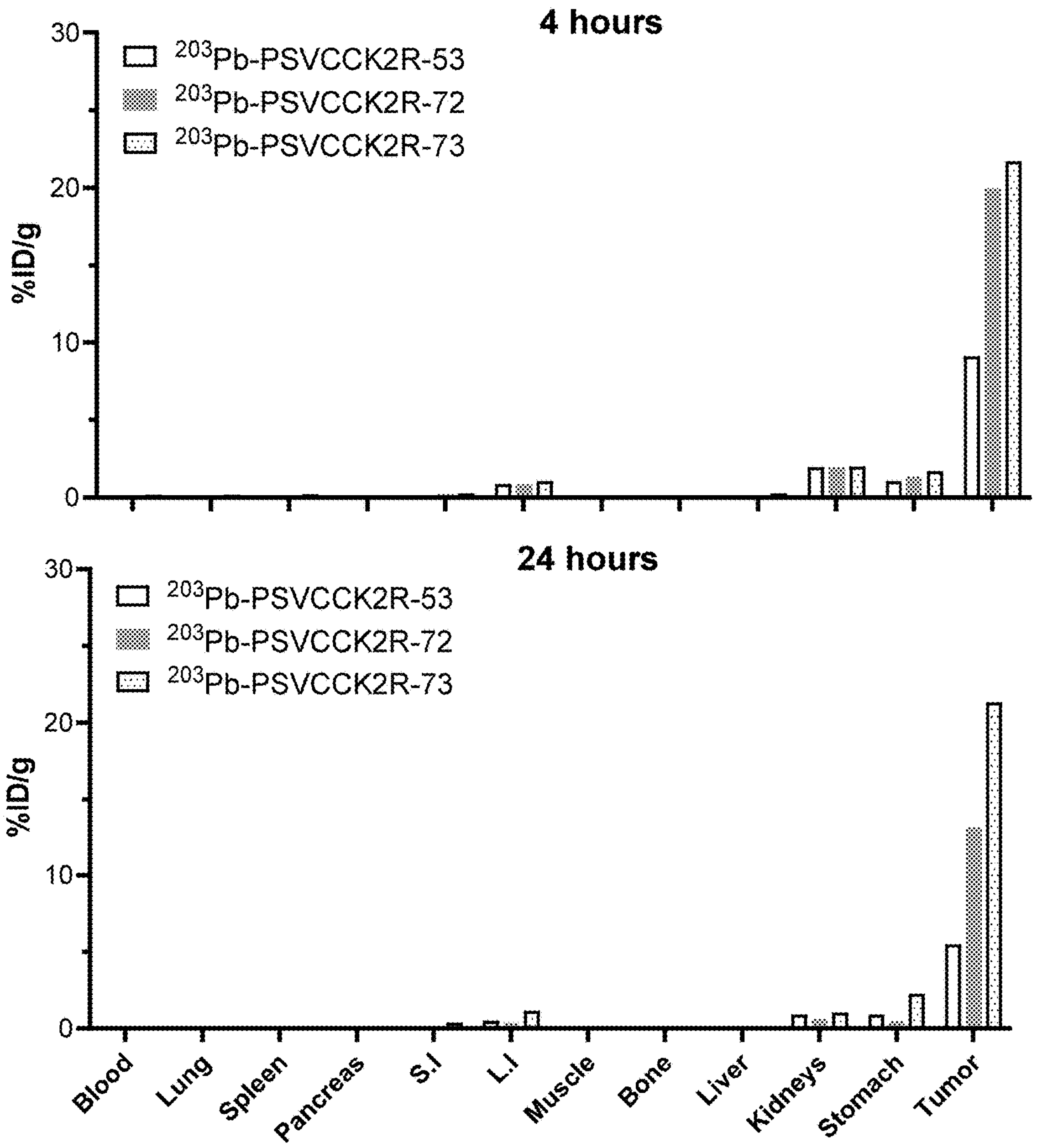

In this Example, DOTA-MGS5 was used as a control compound for internal comparative reference. It was labeled with $^{203}PbCl_2$ reaching over 98% RCY and 95.16% RCP at the end of synthesis (EOS). Further incubation of $^{203}$Pb-DOTA-MGS5 in human serum at 37° C. for 20 hours remained 97.57% stability determined by radio-HPLC (Table 5). The competitive receptor binding of DOTA-MGS5 against $^{125}$I-gastrin-1 demonstrated high binding affinity to A431-CCK2R cell line with $IC_{50}$ of 0.51 nM (Table 3), which is similar to the 0.4 nM of $IC_{50}$ published by Maximilian Klingler's group [2]. The $^{203}$Pb-DOTA-MGS5 bound to A431-CCK2R cells quickly and at 2 hours 80.6% of the total input radioactivity bound to the cells (Table 4), and the majority (80-90%) of the bound radioactivity was internalized into cells (data not shown). Biodistribution showed high tumor uptake of $^{203}$Pb-DOTA-MGS5 at 14.6% ID/g at 4-hour post-injection (p.i.) (FIG. 4). $^{203}$Pb-DOTA-MGS5 was washed out fast from the tumor and at 24-hour p.i. 3.39% ID/g remained in the tumor. Similar to $^{111}$In, $^{68}$Ga- and $^{177}$Lu-DOTA-MGS5, $^{203}$Pb-DOTA-MGS5 rapidly cleared from the body through the kidneys and at 24-hour p.i., only 2.1% ID/g remained in the kidneys. The distribution of $^{203}$Pb-DOTA-MGS5 was low in main organs and tissues except the stomach and pancreas because of the endogenous expression of CCK2R. There was 2.20% and 2.72% ID/g of $^{203}$Pb-DOTA-MGS5 in the stomach for 4-hour and 24-hour, respectively.

TABLE 3

$IC_{50}$ of the CCK2R targeted peptidomimetic conjugates

| Compound | IC50 (nM) |
|---|---|
| DOTA-MGS5 | 0.51 |
| PSVCCK2R-1 | 0.13 |
| PSVCCK2R-2 | 0.17 |
| PSVCCK2R-3 | 0.15 |
| PSVCCK2R-4 | 1.64 |
| PSVCCK2R-5 | 0.65 |
| PSVCCK2R-6 | 0.11 |
| PSVCCK2R-7 | 1.58 |
| PSVCCK2R-8 | 1.17 |
| PSVCCK2R-9 | 1.15 |
| PSVCCK2R-10 | 0.90 |
| PSVCCK2R-11 | 1.19 |
| PSVCCK2R-12 | 140.00 |
| PSVCCK2R-13 | 0.16 |
| PSVCCK2R-21 | 0.0500 |
| PSVCCK2R-22 | 4.74 |
| PSVCCK2R-23 | 1.67 |
| PSVCCK2R-27 | 0.39 |
| PSVCCK2R-28 | 7.96 |
| PSVCCK2R-29 | 357.00 |
| PSVCCK2R-30 | 5.95 |
| PSVCCK2R-32 | 306.00 |
| PSVCCK2R-33 | 5.09 |
| PSVCCK2R-34 | No binding |
| PSVCCK2R-35 | 127.00 |
| PSVCCK2R-36 | No binding |
| PSVCCK2R-37 | No binding |
| PSVCCK2R-38 | 761.00 |
| PSVCCK2R-39 | 417.00 |
| PSVCCK2R-40 | 241.00 |
| PSVCCK2R-41 | 10.00 |
| PSVCCK2R-42 | 0.09 |
| PSVCCK2R-43 | 0.09 |
| PSVCCK2R-44 | No binding |
| PSVCCK2R-45 | 205.00 |
| PSVCCK2R-46 | No binding |
| PSVCCK2R-47 | 78.00 |
| PSVCCK2R-50 | no binding |
| PSVCCK2R-51 | 12.60 |
| PSVCCK2R-52 | 2.80 |
| PSVCCK2R-53 | 1.08 |
| PSVCCK2R-54 | 27.25 |
| PSVCCK2R-55 | 142.65 |

TABLE 3-continued $IC_{50}$ of the CCK2R targeted peptidomimetic conjugates

| Compound | IC50 (nM) |
|---|---|
| PSVCCK2R-56 | 571.00 |
| PSVCCK2R-57 | 0.50 |
| PSVCCK2R-58 | 7.40 |
| PSVCCK2R-59 | 0.30 |
| PSVCCK2R-60 | 8.05 |
| PSVCCK2R-61 | 120.00 |
| PSVCCK2R-62 | no binding |
| PSVCCK2R-63 | 4.90 |
| PSVCCK2R-64 | no binding |
| PSVCCK2R-65 | 0.38 |
| PSVCCK2R-66 | 0.18 |
| PSVCCK2R-67 | 0.30 |
| PSVCCK2R-68 | 2.19 |
| PSVCCK2R-69 | 127.50 |
| PSVCCK2R-70 | 0.29 |
| PSVCCK2R-71 | no binding |
| PSVCCK2R-72 | 0.07 |
| PSVCCK2R-73 | 0.11 |
| PSVCCK2R-75 | 0.49 |
| PSVCCK2R-76 | 1.39 |
| PSVCCK2R-77 | 3.60 |
| PSVCCK2R-78 | 0.11 |

TABLE 4

Two-hour cellular uptake to A431-CCK2R cells at 37° C..

| Compound | 2 h cellular uptake (% of tracer input) |
|---|---|
| $^{203}$Pb-DOTA-MGS5 | 82.0% |
| $^{203}$Pb-PSVCCK2R-1 | 75.0% |
| $^{203}$Pb-PSVCCK2R-2 | 63.3% |
| $^{203}$Pb-PSVCCK2R-3 | 61.5% |
| $^{203}$Pb-PSVCCK2R-4 | 67.5% |
| $^{203}$Pb-PSVCCK2R-5 | 58.5% |
| $^{203}$Pb-PSVCCK2R-6 | 46.5% |
| $^{203}$Pb-PSVCCK2R-7 | 56.2% |
| $^{203}$Pb-PSVCCK2R-8 | 58.7% |
| $^{203}$Pb-PSVCCK2R-9 | 66.4% |
| $^{203}$Pb-PSVCCK2R-10 | 20.6% |
| $^{203}$Pb-PSVCCK2R-11 | 40.5% |
| $^{203}$Pb-PSVCCK2R-12 | 3.4% |
| $^{203}$Pb-PSVCCK2R-13 | 72.5% |
| $^{203}$Pb-PSVCCK2R-21 | 48.1% |
| $^{203}$Pb-PSVCCK2R-22 | 50.1% |
| $^{203}$Pb-PSVCCK2R-23 | 47.1% |
| $^{203}$Pb-PSVCCK2R-25 | 59.8% |
| $^{203}$Pb-PSVCCK2R-26 | 56.1% |
| $^{203}$Pb-PSVCCK2R-27 | 54.5% |
| $^{203}$Pb-PSVCCK2R-28 | 27.1% |
| $^{203}$Pb-PSVCCK2R-30 | 15.2% |
| $^{203}$Pb-PSVCCK2R-33 | 5.0% |
| $^{203}$Pb-PSVCCK2R-41 | 38.3% |
| $^{203}$Pb-PSVCCK2R-42 | 82.6% |
| $^{203}$Pb-PSVCCK2R-43 | 49.2% |
| $^{203}$Pb-PSVCCK2R-51 | 46.8% |
| $^{203}$Pb-PSVCCK2R-52 | 40.4% |
| $^{203}$Pb-PSVCCK2R-53 | 71.4% |
| $^{203}$Pb-PSVCCK2R-57 | 76.5% |
| $^{203}$Pb-PSVCCK2R-58 | 42.6% |
| $^{203}$Pb-PSVCCK2R-59 | 59.0% |
| $^{203}$Pb-PSVCCK2R-60 | 44.6% |
| $^{203}$Pb-PSVCCK2R-63 | 54.6% |
| $^{203}$Pb-PSVCCK2R-65 | 79.0% |
| $^{203}$Pb-PSVCCK2R-66 | 71.6% |
| $^{203}$Pb-PSVCCK2R-67 | 79.5% |
| $^{203}$Pb-PSVCCK2R-68 | 42.9% |
| $^{203}$Pb-PSVCCK2R-70 | 57.0% |
| $^{203}$Pb-PSVCCK2R-72 | 57.3% |
| $^{203}$Pb-PSVCCK2R-73 | 61.1% |

TABLE 4-continued

Two-hour cellular uptake to A431-CCK2R cells at 37° C..

| Compound | 2 h cellular uptake (% of tracer input) |
|---|---|
| $^{203}$Pb-PSVCCK2R-75 | 51.8% |
| $^{203}$Pb-PSVCCK2R-77 | 57.7% |
| $^{203}$Pb-PSVCCK2R-78 | 65.9% |

TABLE 5

Radiochemical purity (RCP, %) of CCK2R targeted peptidomimetics at the end of synthesis (EOS) and 20-hour human serum stability at 37° C. as measured using Radio-HPLC.

| Compound | EOS (%) | 20-hour in serum (%) |
|---|---|---|
| $^{203}$Pb-DOTA-MGS5 | 95.16 | 97.57 |
| $^{203}$Pb-PSVCCK2R-1 | 100 | 96.15 |
| $^{203}$Pb-PSVCCK2R-2 | 96.66 | 95.27 |
| $^{203}$Pb-PSVCCK2R-3 | 94.97 | 94.06 |
| $^{203}$Pb-PSVCCK2R-4 | 95.38 | 88.98 |
| $^{203}$Pb-PSVCCK2R-5 | 96.85 | 71.95 |
| $^{203}$Pb-PSVCCK2R-6 | 95.92 | 95.89 |
| $^{203}$Pb-PSVCCK2R-7 | 92.6 | 89.6 |
| $^{203}$Pb-PSVCCK2R-8 | 98.8 | 93.6 |
| $^{203}$Pb-PSVCCK2R-9 | 92.8 | 82.2 |
| $^{203}$Pb-PSVCCK2R-13 | 100 | 95.5 |
| $^{203}$Pb-PSVCCK2R-42 | 98.7 | 97.5 |
| $^{203}$Pb-PSVCCK2R-57 | 99 | 99.5 |
| $^{203}$Pb-PSVCCK2R-73 | 100 | 90.0 |

Example 3

PSVCCK2R-1 was derived directly from DOTA-MGS5, a radiopharmaceutical compound disclosed in U.S. Pat. No. 12,049,518, by replacing DOTA chelator with lead-specific chelator PSC that was proved to facilitate for $^{203/212}$Pb radiochemistry [3, 4]. PSVCCK2R-1 increased the binding affinity by 4-fold with 0.13 nM of $IC_{50}$ and achieved similar high cellular uptake level to A431-CCK2R at 37° C. for 2 hours as compared to DOTA-MGS5 (Tables 3 and 4). With almost 100% RCY with $^{203}$Pb-radiolabeling, $^{203}$Pb-PSVCCK2R-1 remained the high serum stability (Table 5). Furthermore, it demonstrated superior biodistribution features to $^{203}$Pb-DOTA-MGS5 regarding the high tumor uptake and retention, 17.55 and 10.03% ID/g at 4- and 24-hour p.i. respectively. This resulted in increased tumor-to-kidney (T/K) and tumor-to-stomach (T/S) ratios as compared to $^{203}$Pb-DOTA-MGS5 (4.00 vs. 3.40 and 12.81 vs. 7.04, respectively) at 4-hour p.i., and at 24-hour p.i. (5.13 vs. 2.93, and 5.45 vs. 2.06, respectively) (FIG. 4). This result validated the advantage of PSC chelator for 203/212Pb radiochemistry over DOTA chelator in the CCK2R targeted peptidomimetics.

Example 4

In reference to the peptide sequence of the pharmacophore of MGS5 ($^{1}$dGlu-$^{2}$Ala-$^{3}$Tyr-$^{4}$Gly-$^{5}$Trp-$^{6}$N-MeNle-$^{7}$Asp-$^{8}$1-Nal, (SEQ ID NO: 1)) as disclosed in U.S. Pat. No. 12,049,518, modification was made for PSVCCK2R-13 by deleting the first four amino acids $^{1}$dGlu-$^{2}$Ala-$^{3}$Tyr-$^{4}$Gly and additing a linker (dGlu-$PEG_2$) and PSC chelator (Table 2). PSVCCK2R-13 (PSC-dGlu-$PEG_2$-Trp-N-Me-Nle-Asp-1-Nal-$NH_2$) maintained the sub-nanomolar level of $IC_{50}$, high cellular uptake and serum stability (Tables 3-5). Furthermore, the shorter peptidomimetics allowed even faster clearance from the blood and the kidneys, resulting in lower distributions in major normal organs. More importantly, $^{203}$Pb-PSVCCK2R-13 demonstrated high tumor uptake and retention with 17.75 and 14.72% ID/g at 4- and 24-hour p.i., respectively. The T/K and T/S ratios at 24-hour increased to 15.82 and 13.81, respectively (FIG. 4, Table 6). Several cleavage sites have been reported for minigastrin analogs (Try-Gly, Gly-Trp, and Asp-Phe), of which the Asp-Phe was chemically addressed by replacing the Asp-Phe with Asp-1-Nal in MGS5 [5]. Gunther's group has developed another minigastrin analog as a PET radiotracer $^{68}$Ga-DOTA-CCK-66 (DOTA-γ-glu-$PEG_3$-Trp-(N-Me)Nle-Asp-1-Nal-$NH_2$) and acquired first-in-human PET imaging for medullary thyroid carcer patients [6] with favorable clinical dosimetry [7]. They further tested that $^{177}$Lu-DOTA-CCK-66 demonstrated higher metabolic stability than $^{177}$Lu-DOTA-MGS5 by deleting the moiety of Try-Gly-Trp and therefore significantly improved AR42J tumor retention at 24 hours in mice bearing AR42J tumor xenograft [6]. Preclinical evaluation of $^{225}$Ac-DOTA-CCK66 targeted alpha therapy demonstrated better efficacy in treating NOD SCID mice bearing AR42J tumor xenograft than $^{177}$Lu-DOTA-CCK-66 [8].

TABLE 6

Tumor-to-kidney (T/K) and tumor-to-stomach (T/S) ratios of CCK2R targeted peptidomimetics at 4 hours and 24 hours.

| Compound | 4-hour T/K | 4-hour T/S | 24-hour T/K | 24-hour T/S |
|---|---|---|---|---|
| $^{203}$Pb-DOTA-MGS5 | 3.40 | 7.04 | 2.93 | 2.06 |
| $^{203}$Pb-PSVCCK2R-1 | 4.00 | 12.81 | 5.13 | 5.45 |
| $^{203}$Pb-PSVCCK2R-2 | 2.82 | 9.27 | 3.21 | 5.77 |
| $^{203}$Pb-PSVCCK2R-3 | 1.77 | 2.49 | 2.85 | 6.40 |
| $^{203}$Pb-PSVCCK2R-4 | 6.89 | 2.08 | 19.01 | 6.87 |
| $^{203}$Pb-PSVCCK2R-5 | 6.76 | 6.45 | 9.83 | 4.19 |
| $^{203}$Pb-PSVCCK2R-6 | 19.93 | 7.07 | 6.68 | 4.13 |
| $^{203}$Pb-PSVCCK2R-9 | 1.89 | 7.25 | 1.87 | 5.90 |
| $^{203}$Pb-PSVCCK2R-11 | 1.84 | 6.46 | 1.88 | 12.77 |
| $^{203}$Pb-PSVCCK2R-13 | 5.14 | 10.32 | 15.82 | 13.81 |
| $^{203}$Pb-PSVCCK2R-25 | 3.53 | 6.76 | 2.14 | 4.47 |
| $^{203}$Pb-PSVCCK2R-26 | 2.70 | 9.03 | 3.66 | 10.17 |
| $^{203}$Pb-PSVCCK2R-30 | 2.72 | 6.99 | 5.67 | 7.70 |
| $^{203}$Pb-PSVCCK2R-42 | 12.26 | 5.36 | 20.58 | 7.69 |
| $^{203}$Pb-PSVCCK2R-65 | 11.39 | 10.48 | 17.30 | 14.18 |
| $^{203}$Pb-PSVCCK2R-67 | 9.94 | 6.78 | 12.08 | 8.36 |
| $^{203}$Pb-PSVCCK2R-53 | 4.65 | 8.65 | 5.90 | 6.11 |
| $^{203}$Pb-PSVCCK2R-72 | 10.07 | 15.26 | 20.77 | 31.50 |
| $^{203}$Pb-PSVCCK2R-73 | 10.91 | 12.97 | 21.39 | 9.83 |

Example 5

The structure of PSVCCK2R-42 (PSC-dGlu-PEG2-Trp (4-Cl)—N-Me-Nle-Asp-1-Nal-$NH_2$) keeps PSC chelator and the dGlu-$PEG_2$ linker, with a substitution of chloride on the C(4) position of the Trp residue within the pharmacophore. Most of the modifications on the Trp residue decreased the binding affinity by at least 10-100 folds or even caused the complete loss of binding capacity. However, PSVCCK2R-42, with a substitution of chlorine (—Cl) at the C(4) position, showed an $IC_{50}$ of 0.09 nM and outstanding 2-hour uptake of 82.6% of the total added radioactivity at 37° C., indicating the surprising and unexpected effects of the modification in spatial configuration as disclosed in the present invention (Table 2). This replacement on the C(4) position was critical, since the chlorine replacement on the C(5) position (e.g., PSVCCK2R-63: PSC-dGlu-$PEG_2$-Trp (5-Cl)—N-Me-Nle-Asp-1-Nal-$NH_2$) and C(6) position (e.g., PSVCCK2R-30: PSC-dGlu-$PEG_2$-Trp(6-Cl)—N-Me-Nle- Asp-1-Nal-$NH_2$) of the Trp residue decreased the $IC_{50}$ to 4.95 nM and 5.95 nM, respectively. Furthermore, the 2-hour cellular uptake decreased to 54.6% and 15.2%, respectively. Other modifications on the C(4) position of Trp residue, including cyano-(PSVCCK2R-65), methyl-(PSVCCK2R-66), and bromo-(PSVCCK2R-67) substitutions, also demonstrated lower sub-nanomolar level of $IC_{50}$ (0.1-0.38 nM) and over 72-79% of cellular uptake, while C(4) fluoride-substitution (PSVCCK2R-70) showed 0.48 nM $IC_{50}$ and 57% of uptake (Tables 3 and 4). These results indicate the surprising, unexpected effect of proximity of substitutions on the Trp residue ring on the binding capacity to the receptor binding pocket. In in vivo biodistribution study, $^{203}$Pb-PSVCCK2R-42 has demonstrated favorable tumor uptake and retention with 23.3 and 14.0% ID/g at 4 h and 24 h, respectively, as compared to 4.2 and 4.7% ID/g for $^{203}$Pb-PSVCCK2R-30. $^{203}$Pb-PSVCCK2R-47 demonstrated high tumor uptake at 4 h p.i. with 27.3% ID/g and decreased to 10.1% ID/g at 24 h p.i (FIG. 4). $^{203}$Pb-PSVCCK2R-65 showed good biodistribution profile as well with high tumor uptake and fast clearance through the kidneys and low stomach retention. These results showed that the unexpected, surprising effects of modifications on the Trp residue were specific and non-obvious as compared to the control (reference) compounds DOTA-MGS5 and DOTA-CCK-66 as well as modifications on other atom positions of the Trp residue.

The following Enumerated Embodiments are provided to illustrate aspects of the disclosure, although the embodiments are not intended to be limiting and other aspects and/or embodiments may also be provided.

Embodiment 1. A peptidomimetic targeting cholecystokinin 2 receptor (CCK2R) comprising an amino acid sequence that is of general formula (1):

$$X_0—X_1\text{-Asp-}X_2 \quad (1)$$

wherein $X_0$. $X_1$ and $X_2$ are independently natural or unnatural (non-proteinogenic) amino acids, and wherein $X_0$, $X_1$ and $X_2$ are optionally substituted.

Embodiment 2. The peptidomimetic according to Embodiment 1, wherein $X_0$, $X_1$ and $X_2$ are all L-amino acids or independently L- or D-amino acid.

Embodiment 3. The peptidomimetic according to Embodiment 1, wherein $X_0$, $X_1$ and $X_2$ are all D-amino acids or independently L- or D-amino acid.

Embodiment 4. The peptidomimetic according to Embodiment 1, wherein one or more of $X_0$, $X_1$ and $X_2$ are beta-homo amino acids.

Embodiment 5. The peptidomimetic according to any preceding Embodiment, wherein $X_0$. $X_1$ and $X_2$ are independently hydrophobic amino acids.

Embodiment 6. The peptidomimetic according to any preceding Embodiment, wherein $X_0$ is an unnatural (non-proteinogenic), hydrophobic amino acid with structural similarity to Phe or Trp.

Embodiment 7. The peptidomimetic according to any preceding Embodiment, wherein $X_0$ is selected from the group consisting of Phe, Trp, 1-Nal, 2-Nal, (2-Indanyl) glycine (IGL), beta-Homo-Trp (bHTrp), L-1,2,3,4-Tetrahydronorharman-3-carboxylic acid (Tpi), L-1,2,3,4-tetrahydroisoquinoline-3-carboxylic acid (Tic), (3-benzothienyl)-L-alanine (Bta), p-benzoyl-L-phenylalanine (Bpa), 3-(4-Biphenyl)-L-alanine (Bip), L-Phe-(4-(4-pyridinyl)-OH (F-4-Pyr), L-Phe (4-3-pyridinyl-OH (F-3-Pyr), L-m-Tyr (3-Phenoxy)-OH (Y-3-F), Fmoc-7-Aza-L-Tryptophan (7-Aza-Trp), Fmoc-4-aza-L-Tryptophan (4-Aza-Trp), and Fmoc-3-(3-pyridyl)-L-alanine (3-Pal).

Embodiment 8. The peptidomimetic according to any preceding Embodiment, wherein $X_0$ is a modified Trp.

Embodiment 9. The peptidomimetic according to any preceding Embodiment, wherein $X_0$ is Trp that is substituted at any permissible position with halo, —CN, —$NO_2$, —$CONH_2$, —O—$C_{1-6}$ alkyl, —OH, $C_{1-6}$ alkyl, $C_{3-6}$ cycloalkyl, $C_{3-6}$ heterocycloalkyl, $C_{6-14}$ aryl, or $C_{6-14}$ heteroaryl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, or $C_{6-14}$ heteroaryl is optionally substituted.

Embodiment 10. The peptidomimetic according to any preceding Embodiment, wherein $X_0$ is Trp with C(4) substitution wherein the C(4) position is substituted by halo, —CN, —$NO_2$, —$CONH_2$, —O—$C_{1-6}$ alkyl, —OH, $C_{1-6}$ alkyl, $C_{3-6}$ cycloalkyl, $C_{3-6}$ heterocycloalkyl, $C_{6-14}$ aryl, or $C_{6-14}$ heteroaryl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, or $C_{6-14}$ heteroaryl is optionally substituted.

Embodiment 11. The peptidomimetic according to any preceding Embodiment, wherein $X_1$ is an unnatural (non-proteinogenic), hydrophobic amino acid with structural similarity to Met.

Embodiment 12. The peptidomimetic according to any preceding Embodiment, wherein $X_1$ has the structure of —N(R)—CH(R)—C(=O)—, and wherein R is selected from the group consisting of hydrogen, halo, —CN, —OH, $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted.

Embodiment 13. The peptidomimetic according to any preceding Embodiment, wherein $X_1$ is selected from the group consisting of unsubstituted or substituted Ala, Leu, Val, Ile, and Nle.

Embodiment 14. The peptidomimetic according to any preceding Embodiment, wherein $X_1$ is unsubstituted or substituted Nle.

Embodiment 15. The peptidomimetic according to any preceding Embodiment, wherein $X_1$ is selected from the group consisting of N-Me-Nle ( 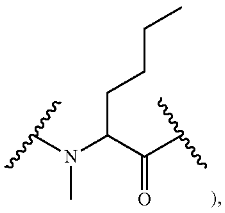 ), N-Me-Nle(6-OH)

( 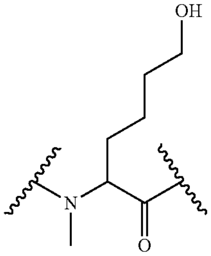 ),

N-Me-Nle(5,5-DiMe)

( 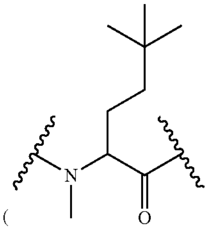 ), and N-Me-Nle(6-O-Bz)

( 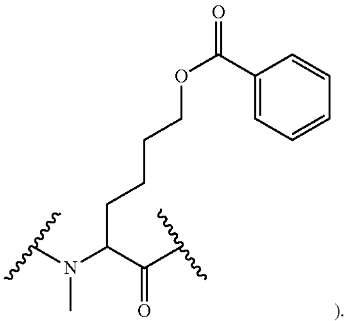 ).

Embodiment 16. The peptidomimetic according to any preceding Embodiment, wherein $X_1$ is substituted Ala.

Embodiment 17. The peptidomimetic according to any preceding Embodiment, wherein $X_1$ is selected from the group consisting of N-Me-beta-cyclohexyl-L-alanine (N-Me-Ala (beta-cyclohexyl); or Me-Cha)

( 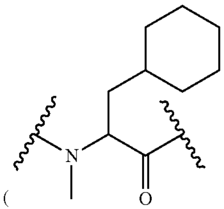 ),

N-Me-beta-cyclobutyl Ala (N-Me-Ala (beta-cyclopentyl))

( 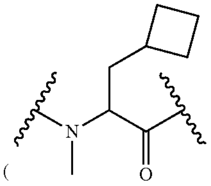 ), and N-Me-cyclopentyl Ala (N-Me-Ala(cyclopentyl))

( 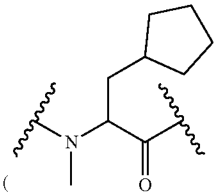 ).

Embodiment 18. The peptidomimetic according to any preceding Embodiment, wherein $X_2$ is an unnatural (non-proteinogenic), hydrophobic amino acid with structural similarity to Phe.

Embodiment 19. The peptidomimetic according to any preceding Embodiment, wherein $X_2$ has the structure of —NH—CH(R)—C(═O)—$NH_2$, and wherein R is selected from, but is not limited to, hydrogen, halo, —CN, —OH, $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted.

Embodiment 20. The peptidomimetic according to any preceding Embodiment, wherein R in $X_2$ is selected from unsubstituted or substituted phenyl, benzyl, 1-adamantyl, 1-naphthyl, 2-naphthyl, 1-anthryl, 2-anthryl, 3-anthryl, phenol, and indole.

Embodiment 21. The peptidomimetic according to any preceding Embodiment, wherein $X_2$ is selected from the group consisting of unsubstituted or substituted Phe-$NH_2$, Trp-$NH_2$, and Nal-$NH_2$.

Embodiment 22. The peptidomimetic according to any preceding Embodiment, wherein $X_2$ is 1-Nal-$NH_2$ (

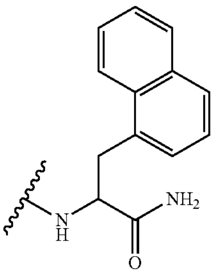 [SMILES: *NC(Cc1cccc2ccccc12)C(N)=O]

).

Embodiment 23. The peptidomimetic according to any preceding Embodiment, wherein $X_2$ is 2-Nal-$NH_2$ ( 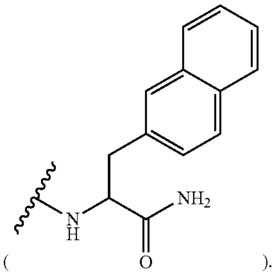 [SMILES: *NC(Cc1ccc2ccccc2c1)C(N)=O] ).

Embodiment 24. The peptidomimetic according to any preceding Embodiment, the peptidomimetic comprising the sequence of formula (1A):

(1A)

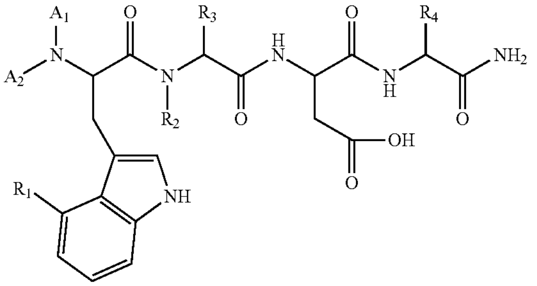

wherein $A_1$ is hydrogen or optionally substituted $C_{1-6}$ alkyl, $A_2$ is hydrogen or a bond connecting the sequence of formula (1A) to the remainder of the peptidomimetic, $R_1$ is selected from the group consisting of hydrogen, halo, —CN, —$NO_2$, —$CONH_2$, —O—$C_{1-6}$ alkyl, —OH, $C_{1-6}$ alkyl, $C_{3-6}$ cycloalkyl, and $C_{3-6}$ heterocycloalkyl, wherein the $C_{1-6}$ alkyl, —O—$C_{1-6}$ alkyl, $C_{3-6}$ cycloalkyl, or $C_{3-6}$ heterocycloalkyl is optionally substituted, $R_2$ is selected from the group consisting of hydrogen, halo, —CN, —OH, and $C_{1-6}$ alkyl, wherein the $C_{1-6}$ alkyl is optionally substituted, $R_3$ is selected from the group consisting of $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted, and $R_4$ is selected from the group consisting of unsubstituted or substituted phenyl, benzyl, 1-adamantyl, 1-naphthyl, 2-naphthyl, 1-anthryl, 2-anthryl, 3-anthryl, phenol, and indole.

Embodiment 25. The peptidomimetic according to any preceding Embodiment, the peptidomimetic comprising the sequence of formula (1B):

(1B)

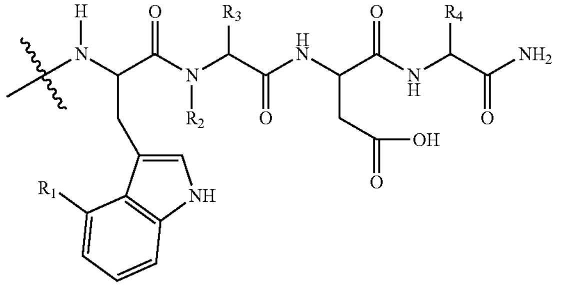

wherein

 designates the point of attachment of the sequence of formula (1B) to the remainder of the peptidomimetic, $R_1$ is selected from the group consisting of hydrogen, halo, —CN, —$NO_2$, —$CONH_2$, —O—$C_{1-6}$ alkyl, —OH, $C_{1-6}$ alkyl, $C_{3-6}$ cycloalkyl, and $C_{3-6}$ heterocycloalkyl, wherein the $C_{1-6}$ alkyl, —O—$C_{1-6}$ alkyl, $C_{3-6}$ cycloalkyl, or $C_{3-6}$ heterocycloalkyl is optionally substituted, $R_2$ is selected from the group consisting of hydrogen, halo, —CN, —OH, and $C_{1-6}$ alkyl, wherein the $C_{1-6}$ alkyl is optionally substituted, $R_3$ is selected from the group consisting of $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted, and $R_4$ is selected from the group consisting of unsubstituted or substituted phenyl, benzyl, 1-adamantyl, 1-naphthyl, 2-naphthyl, 1-anthryl, 2-anthryl, 3-anthryl, phenol, and indole.

Embodiment 26. A peptidomimetic conjugate targeting cholecystokinin 2 receptor (CCK2R), the peptidomimetic is of general formula (2):

$$Z\text{-}L\text{-}X_0\text{—}X_1\text{-Asp-}X_2 \quad (2)$$

wherein

Z is a chelator capable of chelating a radionuclide, one or multiple cytotoxic agents, one or multiple prosthetic groups, or one or multiple fluorophore molecules, L is a linker, or absent, $X_0$ is Trp, or Trp with substitution, wherein the substitution is preferably at C(4), and $X_1$ and $X_2$ are natural or unnatural amino acids.

Embodiment 27. The peptidomimetic conjugate according to Embodiment 26, wherein Z is any chelator described herein.

Embodiment 28. The peptidomimetic conjugate according to any preceding Embodiment, wherein L is any linker described herein.

Embodiment 29. The peptidomimetic conjugate according to any preceding Embodiment, wherein $X_0$ is Trp without any modification.

Embodiment 30. The peptidomimetic conjugate according to any one of Embodiments 1-3, wherein $X_0$ is Trp with C(4) substitution and the C(4) position is substituted by halo, —CN, —OH, —$NO_2$, —$CONH_2$, —O—$C_{1-6}$ alkyl, $C_{1-6}$ alkyl, $C_{3-6}$ cycloalkyl, $C_{3-6}$ heterocycloalkyl, $C_{6-14}$ aryl, or $C_{6-14}$ heteroaryl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, or $C_{6-14}$ heteroaryl is optionally substituted.

Embodiment 31. The peptidomimetic conjugate according to any previous Embodiment wherein $X_0$ is

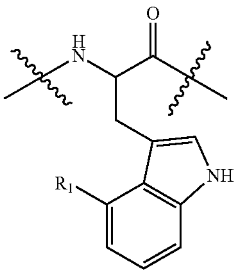

$R_1$ is as halo, cyano, methyl, or —OMe and "⌇" designates the point of attachment of $X_0$ to the remainder of the peptidomimetic conjugate.

Embodiment 32. The peptidomimetic conjugate according to any previous Embodiment wherein $X_0$ is

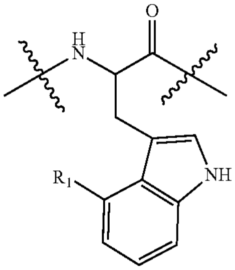

$R_1$ is as chloro, bromo or cyano and "⌇" designates the point of attachment of $X_0$ to the remainder of the peptidomimetic conjugate.

Embodiment 33. The peptidomimetic conjugate according to any preceding Embodiment, wherein $X_1$ has the structure —N($R_5$)—CH($R_5$)—C(═O)—, $R_5$ is selected from the group consisting of hydrogen, halo, —CN, —OH, $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted.

Embodiment 34. The peptidomimetic conjugate according to any preceding Embodiment, wherein $X_2$ has the structure of —NH—CH($R_6$)—C(═O)—$NH_2$, wherein $R_6$ is selected from the group consisting of hydrogen, halo, —CN, —OH, $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{1-6}$ alkyl, —O—$C_{1-6}$ alkyl, $C_{3-6}$ cycloalkyl, $C_{3-6}$ heterocycloalkyl, $C_{6-14}$ aryl, $C_{6-14}$ heteroaryl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted.

Embodiment 35. The peptidomimetic conjugate according to any preceding Embodiment, wherein $R_6$ is selected from unsubstituted or substituted phenyl, benzyl, 1-adamantyl, 1-naphthyl, 2-naphthyl, 1-anthryl, 2-anthryl, 3-anthryl, phenol, and indole.

Embodiment 36. The peptidomimetic conjugate according to any preceding Embodiment, wherein $X_1$ is selected from the group consisting of unsubstituted or substituted Ala, Leu, Val, Ile, and Nle.

Embodiment 37. The peptidomimetic conjugate according to any preceding Embodiment, wherein $X_2$ is selected from the group consisting of unsubstituted or substituted Phe-$NH_2$, and Nal-$NH_2$.

Embodiment 38. A peptidomimetic conjugate that is of formula (3):

(3)

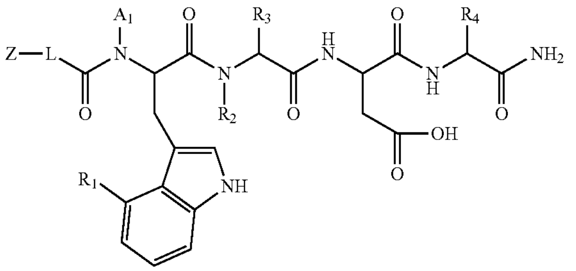

wherein $A_1$ is hydrogen or optionally substituted $C_{1-6}$ alkyl,

L is a linker, or absent, $R_1$ is selected from the group consisting of hydrogen, halo, —CN, —OH, —$NO_2$, —$CONH_2$, —O—$C_{1-6}$ alkyl, $C_{1-6}$ alkyl, $C_{3-6}$ cycloalkyl, and $C_{3-6}$ heterocycloalkyl, wherein the $C_{1-6}$ alkyl, —O—$C_{1-6}$ alkyl, $C_{3-6}$ cycloalkyl, or $C_{3-6}$ heterocycloalkyl is optionally substituted, $R_2$ is selected from the group consisting of hydrogen, halo, —CN, —OH, and $C_{1-6}$ alkyl, wherein the $C_{1-6}$ alkyl is optionally substituted, $R_3$ is selected from the group consisting of $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted, $R_4$ is selected from the group consisting of unsubstituted or substituted phenyl, benzyl, 1-adamantyl, 1-naphthyl, 2-naphthyl, 1-anthryl, 2-anthryl, 3-anthryl, phenol, and indole, and Z is a chelator capable of chelating a radionuclide, one or multiple cytotoxic agents, one or multiple prosthetic groups, or one or multiple fluorophore molecules.

Embodiment 39. The peptidomimetic conjugate according to any previous Embodiment, wherein Z is selected from the group consisting of DOTA (1,4,7,10-tetraazacyclododecane-1,4,7,10-tetraacetic acid), DOTA-NHS-ester, p-SCN-Bn-DOTA (C-DOTA), DOTAGA (2-[1,4,7,10-tetraazacyclododecane]-pentanedioic acid), DOTAGA-anhydride, DO2A (4,11-bis(carboxymethyl)-1,4,8,11-tetraazabicyclo [6.6.2]hexadecan), CB-DO2A (4,10-bis(carboxymethyl)-1,4,7,10-tetraazabicyclo[5.5.2]tetradecane), DPDP (N,N'-dipyridoxylethylendiamine-N,N'-diacetate-5,5'-bis (phosphat)), ITC-MX (1-p-Isothiocyanato-benzyl-methyl-diethylenetriaminepentaacetic acid), TCMC (1,4,7,10-tetrakis (carbamoylmethyl)-1,4,7,10-tetraazacyclododecane), p-SCN-Bn-TCMC (S-2-(4-isothiocyanatobenzyl)-1,4,7,10-tetraaza-1,4,7,10-tetra (2-carbamoylmethyl)cyclododecane), 3p-C-DEPA (2-[(carboxymethyl)]-[5-(4-nitrophenyl-1-[4,7,10-tris-(carboxymethyl)-1,4,7,10-tetraazacyclododecan-1-yl]pentan-2-yl)-amino]acetic acid), 3p-C-DEPA-NCS (2,2',2"-(10-(2-(bis (carboxymethyl)amino)-5-(4-isothiocyanatophenyl)pentyl)-1,4,7,10-tetraazacyclododecane-1,4,7-triyl)triacetic acid), p-$NH_2$-Bn-Oxo-DO3A (1-Oxa-4,7,10-tetraazacyclododecane-5-S-(4-aminobenzyl)-4,7,10-triacetic acid), TETA (1,4,8,11-tetraazacyclotetradecane 1,4,8,11-tetraacetic acid), BAT (bis-amino-bis-thiol), p-$NH_2$-Bn-TE3A (2-(4-aminobenzyl)-1,4,7,10-tetraazacyclododecane-1,4,7-triacetic acid), CDTA (cyclohexyl-1,2-diaminetetraacetic acid), CPTA (4-(1,4,8,11-tetraazacyclotetradec-1-yl)-methylbenzoic acid), C-TETA, CB-TE2A (4,11-bis-(carboxymethyl)-1,4,8,11-tetraazabicyclo[6.6.2]-hexadecane), CB-TE1A1P (1,4,8,11-tetraazabicyclohexadecane-4-acetic acid-11-methanephosphonic acid), CB-TE2P (1,4,8,11-tetraazacyclotetradecane-1,8-di(methanephosphonic acid)), MM-TE2A, DM-TE2A, TE2A (4,11-bis(carboxymethyl)-1,4,8,11-tetraaza-bicyclo[6.6.2]hexadecane), TMT (terpyridine-bis(methyleneamine) tetraacetic acid), TRITA (1,4,7,10-tetraazacyclotridecan-N,N',N",N"-tetraacetic acid), TTHA (triethylenetetraaminehexaacetic acid), Diamsar (1,8-Diamino-3,6,10,13,16,19-hexaazabicyclo[6,6,6]-eicosane), SarAr (1-N-(4-aminobenzyl)-3,6, 10, 13, 16, 19-hexaazabicyclo[6.6.6]-eicosane-1,8-diamine), AmBaSar, BaBaSar, NOTA (1,4,7-triazacyclononane-1,4,7-triacetic acid), p-SCN-Bn-NOTA (2-S-(4-isothiocyanatobenzyl)-1,4,7-triazacyclononane-1,4,7-triacetic acid), NODA (1,4,7-triazacyclononane-1,4-diiacetic acid), NODASA (1,4,7-triazacyclononan-1-succinic acid-4,7-diacetic acid), NODAGA (1-(1-carboxy-3-carboxypropyl)-4,7-(carboxy)-1,4,7-triazacyclononane), NETA ({4-[2-(bis-carboxymethylamino)-ethyl]-7-carboxymethyl-[1,4,7]triazonan-1-yl}-acetic acid), NETA-monoamide, C-NE3TA-NCS (7-[2-({carboxymethyl}[{4-isothiocyanatophenyl}methyl]amino)ethyl]-1,4,7-triazacyclononane-1,4-diacetic acid), C-NETA-NCS (4-isothiocyanatobenzyl-1-oxa-4,7,10-triazacyclododecane-N,N',N"-triacetic acid), 3p-C-NETA (4-[2-(bis-carboxymethylamino)-5-(4-nitrophenyl)-entyl])-7-carboxymethyl-triazonan-1-yl acetic acid), TACN-TM (N,N',N"-tris (2-mercaptoethyl)-1,4,7-triazacyclononane), DTPA (diethylenetriaminepentaacetic acid), p-SCN-Bn-DTPA (),

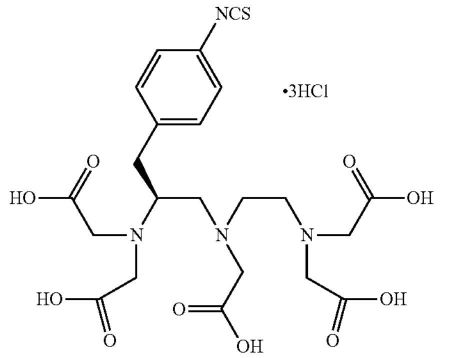

p-SCN-Bn-1B-DTPA, p-SCN-Bn-1B4M-DTPA, CHX-A"-DTPA (2-(p-isothiocyanatobenzyl)-cyclohexyldiethylenetriaminepentaacetic acid), p-SCN-Bn-CHX-A"-DTPA ([(R)-2-Amino-3-(4-isothiocyanatophenyl) propyl]-trans-(S,S)-cyclohexane-1,2-diamine-pentaacetic acid), BAPTA (1,2-bis (o-aminophenoxy) ethane-N,N,N',N'-tetraacetic acid)), TRAP (1,4,7-triazacyclononane 1,4,7-tris [methyl (2-carboxyethyl)phosphinic acid]), AAZTA (1,4-bis(hydroxycarbonyl methyl)-6-[bis(hydroxylcarbonyl methyl)] amino-6-methylperhydro-1,4-diazepine), NOPO (3-(((4,7-bis ((hydroxy(hydroxymethyl)phosphoryl)methyl)-1,4,7-triazonan-1-yl)methyl)(hydroxy)phosphoryl)propanoic acid), $H_2$dedpa (1,2-[[6-(carboxy)-pyridin-2-yl]-methylamino]ethane), $H_4$octapa (N,N'-bis(6-carboxy-2-pyridylmethyl)-ethylenediamine-N,N'-diacetic acid), $H_2$azapa (N,N'-[1-benzyl-1,2,3-triazole-4-yl]methyl-N,N'-[6-(carboxy) pyridin-2-yl]-1,2-diaminoethane), $H_5$decapa (N,N"-[[6-(carboxy)pyridin-2-yl]methyl]-diethylenetriamine-N,N',N"-triacetic acid), p-SCN-Bn-$H_4$octapa (),

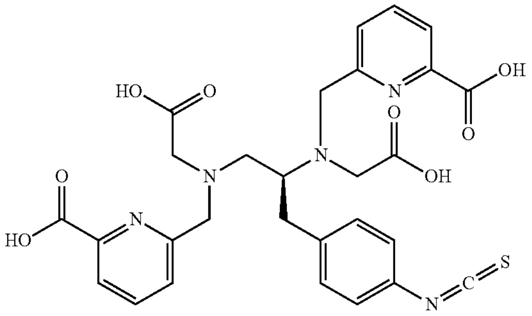 [SMILES: O=C(O)CN(Cc1cccc(C(=O)O)n1)C[C@H](Cc1ccc(N=C=S)cc1)N(CC(=O)O)Cc1cccc(C(=O)O)n1]

EDTA (ethylenediamine-N,N'-tetraacetic acid), EGTA (ethyleneglykol-O,O-bis(2-aminoethyl)-N,N,N',N'-tetraacetic acid), HBED (N,N'-bis(2-hydroxybenzyl)-ethylenediamine-N,N'-diacetic acid), HBED-CC (N,N'-bis [2-hydroxy-5-(carboxyethyl)benzyl]ethylenediamine-N,N'-diacetic acid), (HBED-CC) TFP, HEDTA (hydroxyethyldiaminetriacetic acid), HP-DOA3 (1-(p-nitrobenzyl)-1,4,7,10-tetraazacyclodecan-4,7,10-triacetate), 6-hydrazinyl-N-methylpyridine-3-carboxamide, $H_2$macropa (N,N'-bis [(6-carboxy-2-pyridin) methyl]-4,13-diaza-18-crown-6), THP (4-amino-4-{2-[(3-hydroxy-1,6-dimethyl-4-oxo-1,4-dihydro-pyridin-2-ylmethyl)-carbamoyl]-ethyl} heptanedioic acid bis-[(3-hydroxy-1,6-dimethyl-4-oxo-1,4-dihydro-pyridin-2-ylmethyl)-amide]), SHBED (N,N'-bis(2-hydroxy-5-sulfobenzyl)-ethylenediamine-N,N'-diacetic acid), CP256 (4-acetylamino-4-[2-[(3-hydroxy-1,6-dimethyl-4-oxo-1,4-dihydro-pyridin-2-ylmethyl)-carbamoyl]-ethyl]-heptanedioic acid bis-[(3-hydroxy-1,6-dimethyl-4-oxo-1,4-dihydro-pyridin-2-ylmethyl)-amide]), 2,3-EIOPO (3-hydroxypyridin-2-one), PCTA (3,6,9,15-tetraazabicyclo [9.3.1]-pentadeca-1 (15), 11,13-triene-3,6,9-triacetic acid), p-SCN-Bn-PCTA (3,6,9,15-Tetraazabicyclo[9.3.1]penta-deca-1 (15), 11,13-triene-4-S-(4-isothiocyanatobenzyl)-3,6,9-triacetic acid), OCTAPA (N,NO-bis(6-carboxy-2-pyridyl-methyl)-ethylenediamine-N,NO-diacetic acid), DATA ((6-pentanoic acid)-6-(amino)methy-1,4-diazepinetriacetate), DFO (N'-[5-[acetyl(hydroxy)aminopentyl]-N-[5-[[4-[5-aminopentyl-(hydroxy)amino]-4-oxobutanoyl]amino]pen-tyl]-N-hydroxybutandiamide), p-SCN-Bn-DFO (1-(4-isoth-iocyanatophenyl)-3-[6,17-dihydroxy-7,10,18,21-tetraoxo-27-(N-acetylhydroxylamino)-6,11,17,22-tetraazaheptaeicosine] thiourea), $H_6$phospha (N,N'-(methylenephosphonate)-N,N'-[6-(methoxycarbonyl) pyridin-2-yl]-methyl-1,2-diaminoethane), HEHA (1,4,7, 10, 13, 16-hexaazacyclohexadecane-N,N',N",N"', N"", N""'-hexaacetic acid), p-SCN-Bn-HEHA (2-(4-Isothicyanatoben-zyl)-1,2,7,10,13-hexaazacyclooctadecane-1,4,7,10,13,16-hexaacetic acid), PEPA (1,4,7,10,13-pentaazacyclopentadecane-N,N',N",N"', N""-pentaacetic acid), p-SCN-Bn-PEPA (2-[Bis(carboxymethyl)amino] ethyl-[2-[Bis(carboxymethyl)amino]-3-(4-isothiocyanato-phenyl)propyl]amino]acetic acid), crown (2,2',2",2"-(1,10-dioxa-4,7,13,16-tetraazacyclooctadecane-4,7,13,16-tetrayl) tetraacetic acid), MACROPA (4-amino-6-[[16-[(6-carboxypyridin-2-yl)methyl]-1,4,10,13-tetraoxa-7, 16-diazacyclooctadec-7-yl]methyl]pyridine-2-carboxylic acid), MACROPA-NCS, pypa, py4pa (6,6'-(((azanediylbis (ethane-2,1-diyl))bis((carboxymethyl)azanediyl))bis(meth-ylene))dipicolinic acid), noneunpa (6,6'-(((oxybis(ethane-2, 1-diyl))bis((carboxymethyl)azanediyl))bis(methylene)) dipicolinic acid), DOTAM (2,2',2",2"'-(1,4,7,10-tetraazacyclododecane-1,4,7,10-tetrayl)tetraacetamide), DO3AM (2-(4,7,10-tris(2-amino-2-oxoethyl)-1,4,7,10-tet-raazacyclododecan-1-yl)acetic acid), DOTPI (1,4,7,10-tet-raazacyclododecane-1,4,7,10-tetrakis[methylene(2-car-boxyethylphosphinic acid)]), S-2-(4-isothiocyanatobenzyl)-1,4,7,10-tetraazacyclododecane tetraacetic acid, $mas_3$ (mercaptoacetyl-triserine), diamidedithiols ($N_2S_2$), tri-amidethiols ($N_3S$), tetraamines ($N_4$), hydrazinonicotinic acid (HYNIC), ethylendiamine-N,N'-diacetic acid (EDDA), tricine, desferrioxamine, deferiprone, and derivatives thereof.

Embodiment 40. The peptidomimetic conjugate according to any previous Embodiment wherein Z is

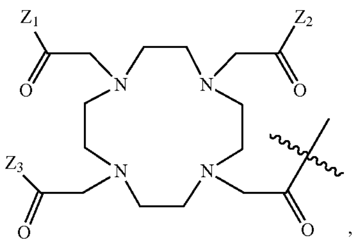

and $Z_1$, $Z_2$ and $Z_3$ are independently $-NH_2$ or $-OH$.

Embodiment 41. The peptidomimetic conjugate according to any previous Embodiment wherein Z is

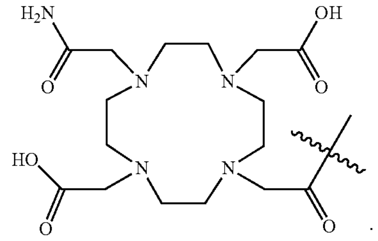

Embodiment 42. The peptidomimetic conjugate according to any previous Embodiment wherein Z is

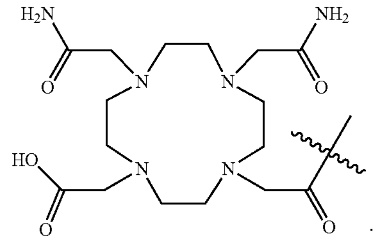

Embodiment 43. The peptidomimetic conjugate according to any previous Embodiment wherein Z is

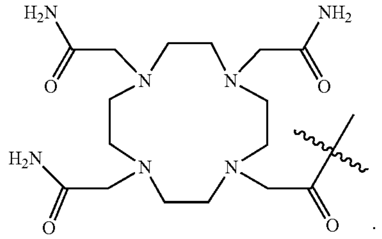 [SMILES: *C(=O)CN1CCN(CC(N)=O)CCN(CC(N)=O)CCN(CC(N)=O)CC1]

Embodiment 44. The peptidomimetic conjugate according to any previous Embodiment wherein Z is

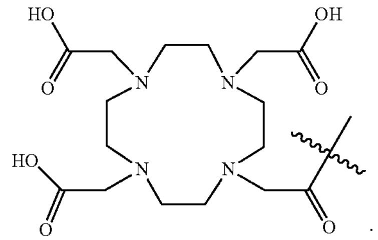

Embodiment 45. The peptidomimetic conjugate according to any previous Embodiment wherein L comprises a structure selected from the group consisting of:

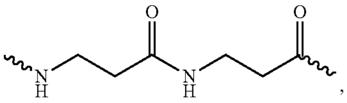
,

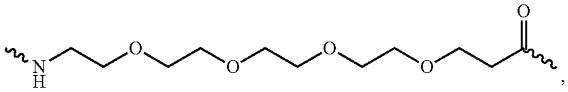
,

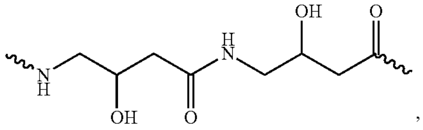
,

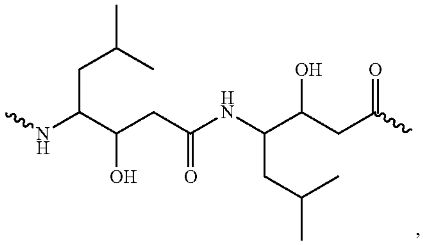
,

-continued

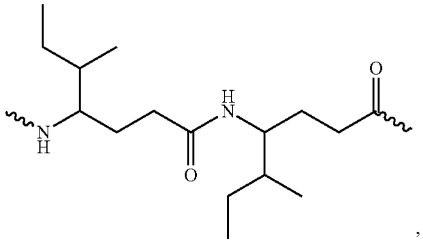
,

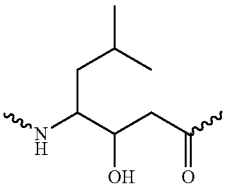
,
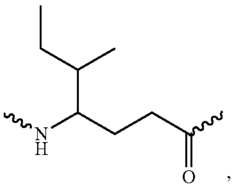
, and

-continued

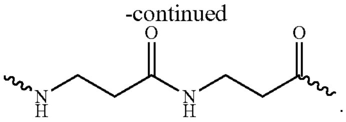
.

Embodiment 46. The peptidomimetic conjugate according to any previous Embodiment wherein L comprises up to six D-form amino acids.

Embodiment 47. The peptidomimetic conjugate according to Embodiment 21 wherein the D-form amino acid is dGlu.

Embodiment 48. The peptidomimetic conjugate according to any previous Embodiment wherein L is

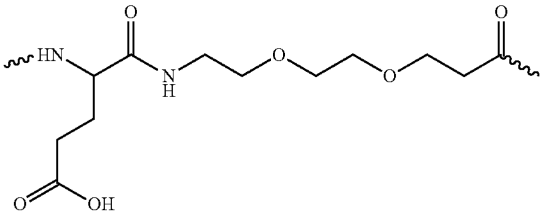
.

Embodiment 49. The peptidomimetic conjugate according to any previous embodiment wherein the peptidomimetic conjugate corresponds to formula (4):

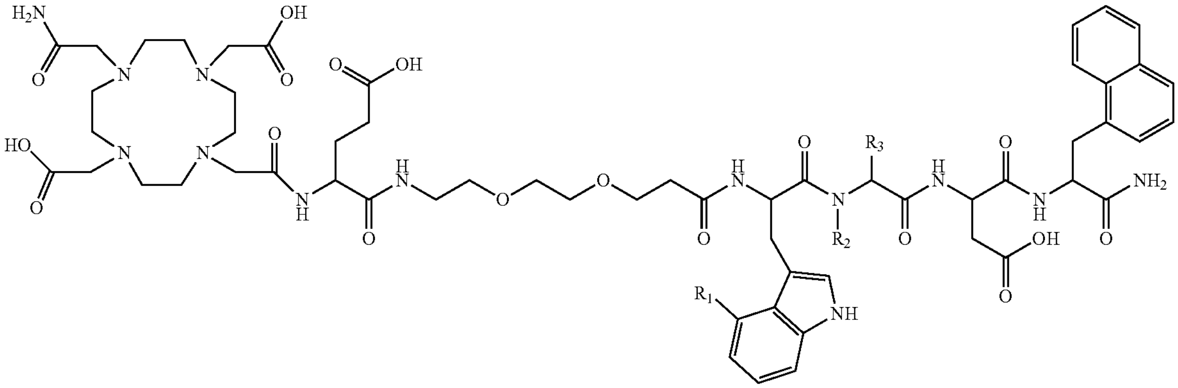

wherein $R_1$ is selected from the group consisting of $C_{1-6}$ alkyl, cyano, halo, —OH, —$NO_2$, —$CONH_2$, —O—$C_{1-6}$ alkyl, $C_{1-6}$ alkyl, and hydroxy, $R_2$ is hydrogen, or substituted or unsubstituted $C_{1-6}$ alkyl, and $R_3$ is selected from the group consisting of $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, and $C_{1-6}$ alkyl-$C_{3-10}$ heterocycloalkyl, wherein the $C_{6-14}$ aryl, $C_{6-14}$ heteroaryl, $C_{1-6}$ alkyl, —O—$C_{1-6}$ alkyl, $C_{3-6}$ cycloalkyl, $C_{3-6}$ heterocycloalkyl, $C_{1-6}$ alkyl-$C_{6-14}$ aryl, $C_{1-6}$ alkyl-$C_{6-14}$ heteroaryl, $C_{1-6}$ alkyl-$C_{3-10}$ cycloalkyl, or $C_{1-6}$ alkyl-$C_{3-10}$ heterocycloalkyl is optionally substituted.

Embodiment 50. The peptidomimetic conjugate according to any previous Embodiment wherein $R_1$ is selected from the group consisting of cyano, halo, hydroxy, nitro, and amide.

Embodiment 51. The peptidomimetic conjugate according to any previous Embodiment wherein $R_1$ is selected from the group consisting of cyano and halo.

Embodiment 52. The peptidomimetic conjugate according to any previous Embodiment wherein $R_2$ is $C_{1-6}$ alkyl.

Embodiment 53. The peptidomimetic conjugate according to any previous Embodiment wherein $R_2$ is methyl.

Embodiment 54. The peptidomimetic conjugate according to any previous Embodiment wherein $R_3$ is selected from the group consisting of butyl, isobutyl, sec-butyl, cyclobutyl, pentyl, cyclopentyl, methyl-cyclopentyl, hexyl, and cyclohexyl.

Embodiment 55. The peptidomimetic conjugate according to any previous Embodiment wherein $R_3$ is selected from the group consisting of cyclobutyl, cyclopentyl, and cyclohexyl.

Embodiment 56. The peptidomimetic conjugate of any previous Embodiment wherein the conjugate is one of the following:

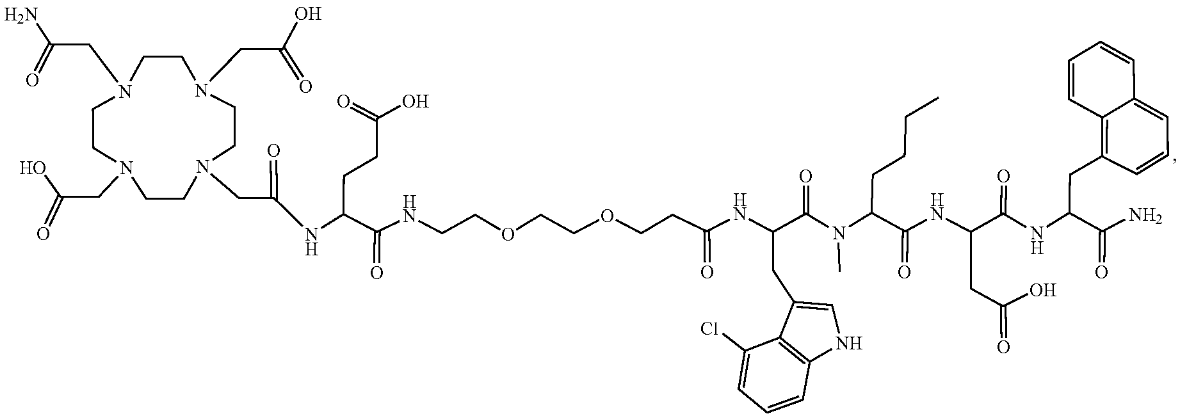

,

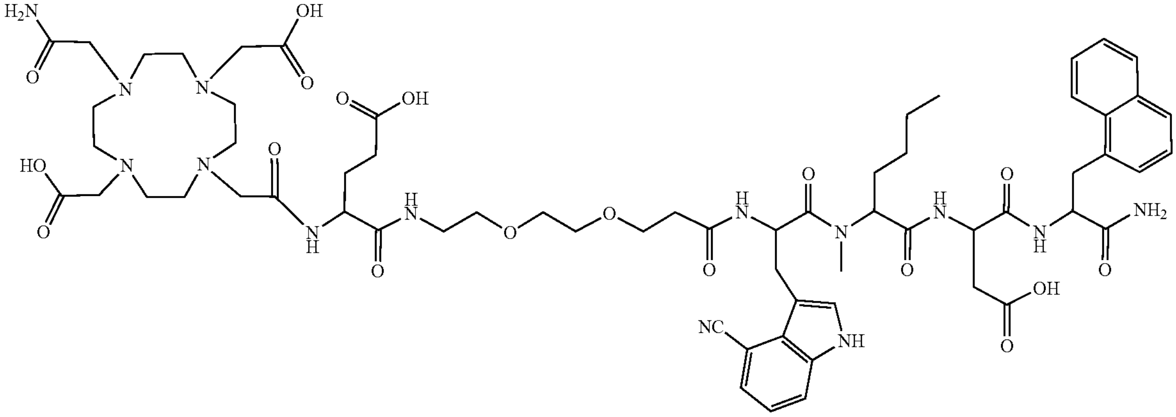

,

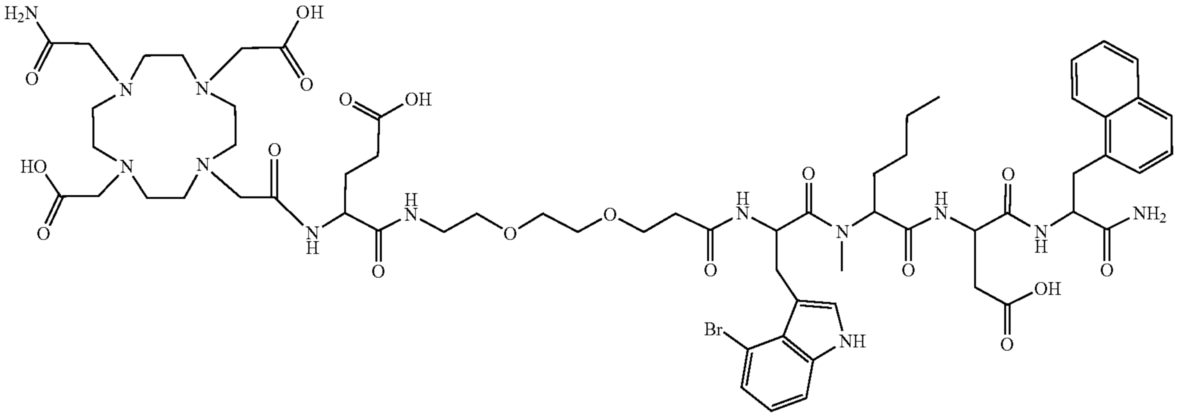

,

-continued

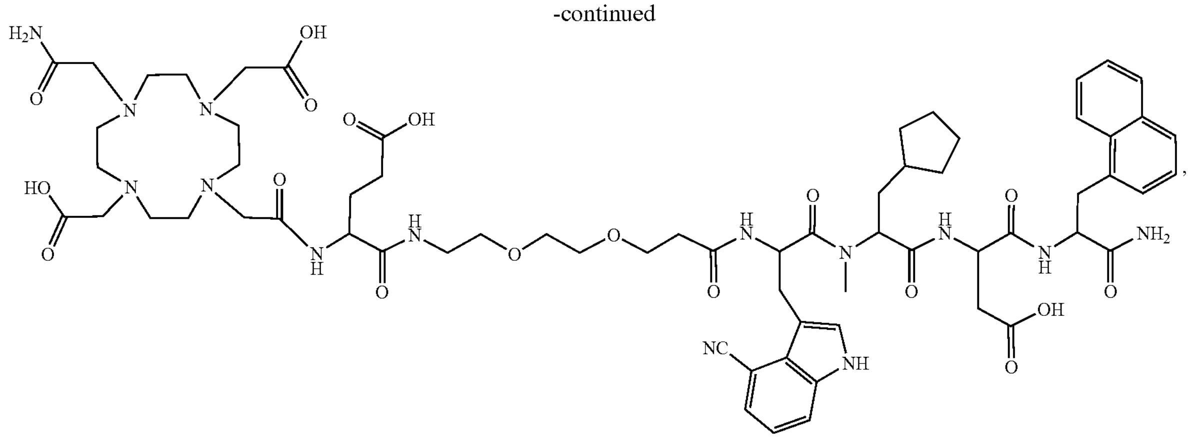

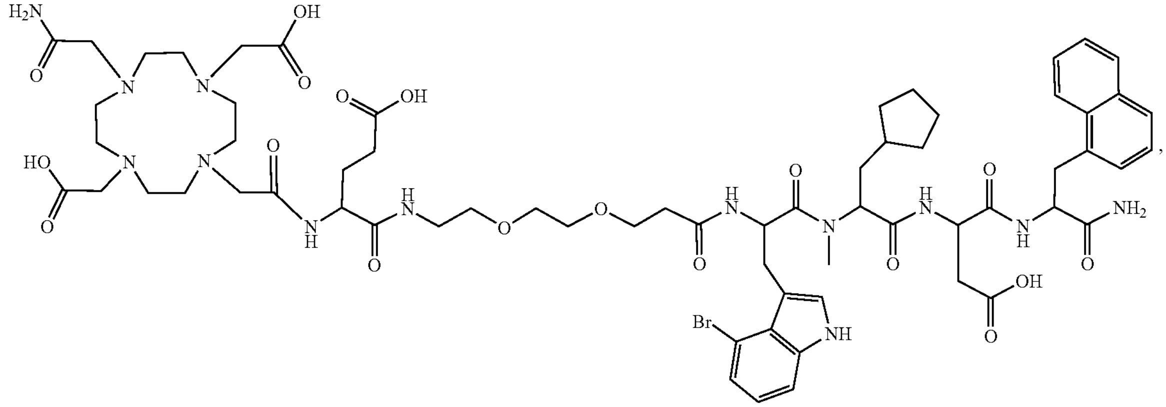

, and

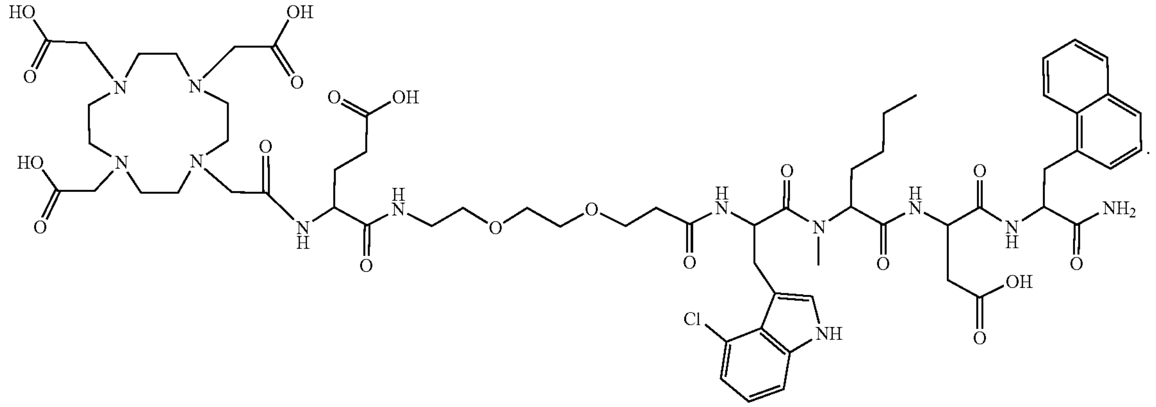

Embodiment 57. A peptidomimetic conjugate according to any previous Embodiment wherein the peptidomimetic conjugate is complexed with a radionuclide.

Embodiment 58. The peptidomimetic conjugate according to any previous Embodiment wherein the peptidomimetic conjugate is complexed with a radionuclide selected from the group consisting of the radionuclides of actinium, bismuth, cesium, copper, gallium, lead, lutetium, radium, rhenium, palladium, polonium, samarium, strontium, terbium, thorium, yttrium, and zirconium.

Embodiment 59. The peptidomimetic conjugate according to any previous Embodiment wherein the peptidomimetic conjugate is complexed with a radionuclide selected from the group consisting of Y-86, Y-90, Lu-177, Re-186, Re-188, Sr-89, Sm-153, Ac-225, Bi-213, Po-213, Bi-212, Ra-223, Ra-224, Th-227, Tb-149, Ga-67, Ga-68, Cu-61, Cu-64, Cu-67, Zr-89, Cs-137, Pb-203, Pb-212, and Pd-103.

Embodiment 60. The peptidomimetic conjugate according to any previous Embodiment wherein the peptidomimetic conjugate is complexed with a divalent radionuclide.

Embodiment 61. The peptidomimetic conjugate according to any previous Embodiment wherein the peptidomimetic conjugate is complexed with $^{203}Pb$ or $^{212}Pb$.

Embodiment 62. The peptidomimetic conjugate according to any previous Embodiment wherein the peptidomimetic conjugate is complexed with $^{61}Cu$, $^{64}Cu$ or $^{67}Cu$.

Embodiment 63. A method for imaging or diagnosing a subject suffering from a cancer associated with expression of cholecystokinin-2 receptor (CCK2R), the method comprising administering the peptidomimetic or peptidomimetic conjugate of any preceding Embodiment to the subject, wherein the peptidomimetic or peptidomimetic conjugate is chelated with a radionuclide suitable for medical imaging use, and imaging the subject.

Embodiment 64. A method for imaging or diagnosing a subject suffering from a cancer associated with expression of CCK2R, the method comprising administering the peptidomimetic or peptidomimetic conjugate of any preceding Embodiment to the subject, wherein the peptidomimetic or peptidomimetic conjugate is complexed with $^{203}$Pb, $^{61}$Cu, or $^{64}$Cu, and imaging the subject.

Embodiment 65. A method for treating a subject suffering from a cancer associated with expression of CCK2R, the method comprising administering the peptidomimetic or peptidomimetic conjugate of any preceding Embodiment to the subject, wherein the peptidomimetic or peptidomimetic conjugate is complexed with a radionuclide suitable for therapeutic use, in a dosage sufficient to kill cancer cells.

Embodiment 66. A method for treating a subject suffering from a cancer associated with expression of CCK2R, the method comprising administering the peptidomimetic or peptidomimetic conjugate of any preceding Embodiment in a dosage sufficient to kill cancer cells, wherein the peptidomimetic or peptidomimetic conjugate is complexed with $^{212}$Pb or $^{67}$Cu.

Embodiment 67. A method of diagnosing and treating a subject suffering from a cancer associated with expression of CCK2R, the method comprising:

diagnosing the subject by administering the peptidomimetic or peptidomimetic conjugate of any preceding Embodiment to the subject, wherein the peptidomimetic or peptidomimetic conjugate is complexed with a radionuclide suitable for medical imaging use, and imaging the subject to diagnose the subject as being afflicted with the cancer, and treating the subject diagnosed as being afflicted by the cancer, by administering the peptidomimetic or peptidomimetic conjugate of any preceding Embodiment to the subject, wherein the peptidomimetic or peptidomimetic conjugate is complexed with a radionuclide suitable for therapeutic use, in a dosage sufficient to kill cancer cells.

Embodiment 68. The method according to any previous Embodiment wherein the subject is imaged using single-photon emission computed tomography (SPECT) imaging or positron emission tomography (PET), optionally in combination with computed tomography (CT) imaging.

Embodiment 69. The method according to any one of Embodiments 63-68, wherein the cancer associated with expression of CCK2R is selected from thyroid cancer, lung cancer, gastrointestinal tumors, tumors of the nervous system, ovarian cancer, gastrointestinal cancer, neuroendocrine tumors, gastroenteropancreatic tumors, neuroblastoma, tumors of the reproductive system, insulinomas, vipomas, bronchial carcinoids, ileal carcinoids, leiomyosarcomas, leiomyomas, and granulosa cell tumors.

Embodiment 70. The method according to any one of Embodiments 63-68, wherein the cancer associated with expression of CCK2R is selected from colorectal cancer (CRC), small cell lung cancer (SCLC), medullary thyroid cancer (MTC), ovarian cancer, testicular germ cell tumor, prostate cancer, breast cancer, and endometrial cancer.

Embodiment 71. A pharmaceutical composition comprising the peptidomimetic or peptidomimetic conjugate or radiopharmaceutical compound of any previous Embodiment and a pharmaceutically acceptable vehicle.

Embodiment 72. A pharmaceutical for the diagnosis or treatment of cancer comprising the peptidomimetic or peptidomimetic conjugate or radiopharmaceutical compound of any previous Embodiment and a pharmaceutically acceptable vehicle.

All patents, patent applications, and publications cited herein are incorporated herein by reference in their entirety as if recited in full herein.

Having described the invention with reference to particular configurations, theories of effectiveness, and the like, it will be apparent to those of skilled in the art that it is not intended that the invention be limited by such illustrative embodiments or mechanisms, and that modifications can be made without departing from the scope or spirit of the invention, as defined by the appended claims. It is intended that all such apparent modifications and variations be included within the scope of the present invention as defined in the appended claims. The claims are meant to cover the claimed components and steps in any sequence which is effective to meet the objectives there intended, unless the context specifically indicates to the contrary.

The foregoing description has been presented for the purposes of illustration and description. It is not intended to be an exhaustive list or limit the invention to the precise forms disclosed. It is contemplated that other alternative processes and methods obvious to those skilled in the art are considered included in the invention. The description is merely examples of embodiments. It is understood that any other modifications, substitutions, or additions may be made, which are within the intended spirit and scope of the disclosure. From the foregoing, it can be seen that the exemplary aspects of the disclosure accomplish the intended objectives.

CITED DOCUMENTS

1. Li, M., et al., Automated cassette-based production of high specific activity [(203/212)Pb]peptide-based theranostic radiopharmaceuticals for image-guided radionuclide therapy for cancer. Appl Radiat Isot, 2017. 127: p. 52-60.
2. Klingler, M., et al., DOTA-MGS5, a New Cholecystokinin-2 Receptor-Targeting Peptide Analog with an Optimized Targeting Profile for Theranostic Use. J Nucl Med, 2019. 60(7): p. 1010-1016.
3. Lee, D., et al., Structural modifications toward improved lead-203/lead-212 peptide-based image-guided alpha-particle radiopharmaceutical therapies for neuroendocrine tumors. Eur J Nucl Med Mol Imaging, 2024. 51(4): p. 1147-1162.
4. Li, M., et al., Preclinical Evaluation of a Lead Specific Chelator (PSC) Conjugated to Radiopeptides for (203)Pb and (212)Pb-Based Theranostics. Pharmaceutics, 2023. 15(2).
5. Ocak, M., et al., Comparison of biological stability and metabolism of CCK2 receptor targeting peptides, a collaborative project under COST BM0607. Eur J Nucl Med Mol Imaging, 2011. 38(8): p. 1426-35.
6. Günther, T., et al., Preclinical Evaluation of Minigastrin Analogs and Proof-of-Concept [(68)Ga]Ga-DOTA-CCK-66 PET/CT in 2 Patients with Medullary Thyroid Cancer. J Nucl Med, 2024. 65(1): p. 33-39.
7. Viering, O., et al., Biodistribution and Radiation Dosimetry for 68 Ga-DOTA-CCK-66, a Novel CCK 2 R-Targeting Compound for Imaging of Medullary Thyroid Cancer. Clin Nucl Med, 2024. 49(12): p. 1091-1097.
8. Holzleitner, N., et al., Preclinical evaluation of (225)Ac-labeled minigastrin analog DOTA-CCK-66 for Targeted Alpha Therapy. Eur J Nucl Med Mol Imaging, 2025. 52(2): p. 458-468.
9. Dillemuth, P. et al. Rapid cleavage of 6-[$^{18}$F]fluoronicotinic acid prosthetic group governs BT12 glioblastoma xenograft uptake: implications for radiolabeling design of biomolecules. EJNMMI Radiopharmacy And Chemistry, (2025) 10:40.
10. U.S. Pat. No. 12,427,209: Dual mode $^{18}$F-labelled theranostic compounds and uses thereof.

SEQUENCE LISTING

```
Sequence total quantity: 20
SEQ ID NO: 1            moltype = AA  length = 8
FEATURE                 Location/Qualifiers
source                  1..8
                        mol_type = protein
                        organism = synthetic construct
MOD_RES                 6
                        note = N-methyl-Norleucine
SITE                    1
                        note = D-Glu
MOD_RES                 8
                        note = 1-Naphthylalanine
SEQUENCE: 1
EAYGWXDX                                                    8

SEQ ID NO: 2            moltype = AA  length = 8
FEATURE                 Location/Qualifiers
source                  1..8
                        mol_type = protein
                        organism = synthetic construct
SITE                    1
                        note = D-Glu
MOD_RES                 6
                        note = N-methyl-Norleucine
MOD_RES                 8
                        note = 1-Naphthylalanine
SEQUENCE: 2
EAYGWXDX                                                    8

SEQ ID NO: 3            moltype = AA  length = 10
FEATURE                 Location/Qualifiers
source                  1..10
                        mol_type = protein
                        organism = synthetic construct
SITE                    1
                        note = beta-Ala
SITE                    2
                        note = beta-Ala
SITE                    3
                        note = D-Glu
MOD_RES                 8
                        note = N-methyl-Norleucine
MOD_RES                 10
                        note = 1-Naphthylalanine
SEQUENCE: 3
AAEAYGWXDX                                                  10

SEQ ID NO: 4            moltype = AA  length = 8
FEATURE                 Location/Qualifiers
source                  1..8
                        mol_type = protein
                        organism = synthetic construct
SITE                    1
                        note = D-Glu
MOD_RES                 6
                        note = N-methyl-Norleucine
MOD_RES                 8
                        note = 1-Naphthylalanine
SEQUENCE: 4
EAYGWXDX                                                    8

SEQ ID NO: 5            moltype = AA  length = 6
FEATURE                 Location/Qualifiers
source                  1..6
                        mol_type = protein
                        organism = synthetic construct
SITE                    2
                        note = beta-Ala
SITE                    1
                        note = beta-Ala
MOD_RES                 4
                        note = N-methyl-Norleucine
MOD_RES                 6
                        note = 1-Naphthylalanine
SEQUENCE: 5
AAWXDX                                                      6

SEQ ID NO: 6            moltype = AA  length = 7
```

```
FEATURE                 Location/Qualifiers
source                  1..7
                        mol_type = protein
                        organism = synthetic construct
SITE                    1
                        note = beta-Ala
SITE                    2
                        note = beta-Ala
SITE                    3
                        note = beta-Ala
MOD_RES                 5
                        note = N-methyl-Norleucine
MOD_RES                 7
                        note = 1-Naphthylalanine
SEQUENCE: 6
AAAWXDX                                                     7

SEQ ID NO: 7            moltype = AA  length = 10
FEATURE                 Location/Qualifiers
source                  1..10
                        mol_type = protein
                        organism = synthetic construct
SITE                    1
                        note = beta-Ala
SITE                    2
                        note = beta-Ala
SITE                    3
                        note = D-Glu
MOD_RES                 8
                        note = N-methyl-Norleucine
METAL                   10
                        note = 1-Naphthylalanine
SEQUENCE: 7
AAEAYGWXDX                                                  10

SEQ ID NO: 8            moltype = AA  length = 8
FEATURE                 Location/Qualifiers
source                  1..8
                        mol_type = protein
                        organism = synthetic construct
SITE                    1
                        note = D-Glu
MOD_RES                 6
                        note = N-methyl-Norleucine
MOD_RES                 8
                        note = 1-Naphthylalanine
SEQUENCE: 8
EAYGWXDX                                                    8

SEQ ID NO: 9            moltype = AA  length = 8
FEATURE                 Location/Qualifiers
source                  1..8
                        mol_type = protein
                        organism = synthetic construct
SITE                    1
                        note = D-Glu
MOD_RES                 6
                        note = N-methyl-Norleucine
MOD_RES                 8
                        note = 1-Naphthylalanine
SEQUENCE: 9
EAYGWXDX                                                    8

SEQ ID NO: 10           moltype = AA  length = 8
FEATURE                 Location/Qualifiers
source                  1..8
                        mol_type = protein
                        organism = synthetic construct
SITE                    1
                        note = D-Glu
MOD_RES                 6
                        note = N-methyl-Norleucine
MOD_RES                 8
                        note = 2-Naphthylalanine
SEQUENCE: 10
EAYGWXDX                                                    8

SEQ ID NO: 11           moltype = AA  length = 8
FEATURE                 Location/Qualifiers
```

```
source                  1..8
                        mol_type = protein
                        organism = synthetic construct
SITE                    1
                        note = D-Glu
SITE                    5
                        note = methyl-Trp
MOD_RES                 6
                        note = N-methyl-Norleucine
MOD_RES                 8
                        note = 1-Naphthylalanine
SEQUENCE: 11
EAYGWXDX                                                                    8

SEQ ID NO: 12           moltype = AA  length = 8
FEATURE                 Location/Qualifiers
source                  1..8
                        mol_type = protein
                        organism = synthetic construct
SITE                    1
                        note = D-Glu
SITE                    5
                        note = N-methyl-Trp
MOD_RES                 6
                        note = N-methyl-Norleucine
MOD_RES                 8
                        note = 1-Naphthylalanine
SEQUENCE: 12
EAYGWXDX                                                                    8

SEQ ID NO: 13           moltype = AA  length = 8
FEATURE                 Location/Qualifiers
source                  1..8
                        mol_type = protein
                        organism = synthetic construct
SITE                    1
                        note = D-Glu
SITE                    2
                        note = cyano-Ala
MOD_RES                 6
                        note = N-methyl-Norleucine
MOD_RES                 8
                        note = 1-Naphthylalanine
SEQUENCE: 13
EAYGWXDX                                                                    8

SEQ ID NO: 14           moltype = AA  length = 8
FEATURE                 Location/Qualifiers
source                  1..8
                        mol_type = protein
                        organism = synthetic construct
SITE                    1
                        note = D-Glu
SITE                    3
                        note = 5-F-Phe
MOD_RES                 6
                        note = N-methyl-Norleucine
MOD_RES                 8
                        note = 1-Naphthylalanine
SEQUENCE: 14
EAFGWXDX                                                                    8

SEQ ID NO: 15           moltype = AA  length = 8
FEATURE                 Location/Qualifiers
source                  1..8
                        mol_type = protein
                        organism = synthetic construct
SITE                    1
                        note = D-Glu
SITE                    3
                        note = 3,5-bis-iodo-Tyr
MOD_RES                 6
                        note = N-methyl-Norleucine
MOD_RES                 8
                        note = 1-Naphthylalanine
SEQUENCE: 15
EAYGWXDX                                                                    8

SEQ ID NO: 16           moltype = AA  length = 8
```

-continued

```
FEATURE                Location/Qualifiers
source                 1..8
                       mol_type = protein
                       organism = synthetic construct
SITE                   1
                       note = D-Glu
SITE                   3
                       note = 3-iodo-Tyr
MOD_RES                6
                       note = N-methyl-Norleucine
MOD_RES                8
                       note = 1-Naphthylalanine
SEQUENCE: 16
EAYGWXDX                                                   8

SEQ ID NO: 17          moltype = AA  length = 8
FEATURE                Location/Qualifiers
source                 1..8
                       mol_type = protein
                       organism = synthetic construct
SITE                   1
                       note = D-Glu
SITE                   3
                       note = 3,5-bis-fluoro-Tyr
MOD_RES                6
                       note = N-methyl-Norleucine
MOD_RES                8
                       note = 1-Naphthylalanine
SEQUENCE: 17
EAYGWXDX                                                   8

SEQ ID NO: 18          moltype = AA  length = 8
FEATURE                Location/Qualifiers
source                 1..8
                       mol_type = protein
                       organism = synthetic construct
SITE                   1
                       note = D-Glu
SITE                   3
                       note = 4-bromo-Phe
MOD_RES                6
                       note = N-methyl-Norleucine
MOD_RES                8
                       note = 1-Naphthylalanine
SEQUENCE: 18
EAFGWXDX                                                   8

SEQ ID NO: 19          moltype = AA  length = 8
FEATURE                Location/Qualifiers
source                 1..8
                       mol_type = protein
                       organism = synthetic construct
SITE                   1
                       note = D-Glu
SITE                   3
                       note = 4-cyano-Phe
MOD_RES                6
                       note = N-methyl-Norleucine
MOD_RES                8
                       note = 1-Naphthylalanine
SEQUENCE: 19
EAFGWXDX                                                   8

SEQ ID NO: 20          moltype = AA  length = 7
FEATURE                Location/Qualifiers
source                 1..7
                       mol_type = protein
                       organism = synthetic construct
SITE                   1
                       note = beta-Glu
SITE                   2
                       note = beta-Glu
SITE                   3
                       note = beta-Ala
MOD_RES                5
                       note = N-methyl-Norleucine
MOD_RES                7
                       note = 1-Naphthylalanine
```

-continued
```
SEQUENCE: 20
EEAWXDX                                                    7
```
What is claimed is:
1. A peptidomimetic conjugate having a structure selected from one of the following:
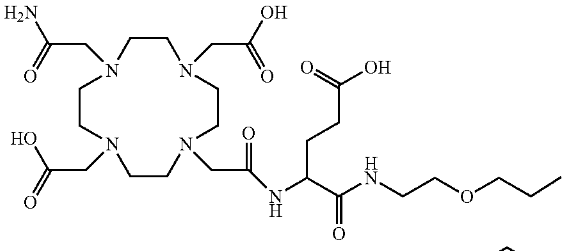
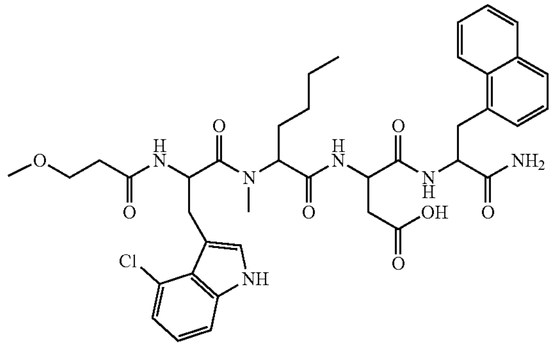
,
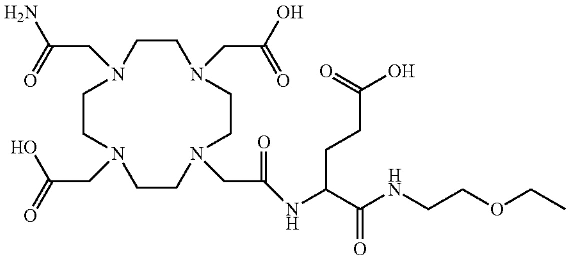
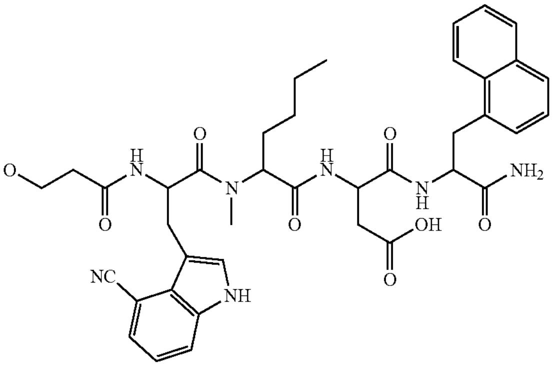
,
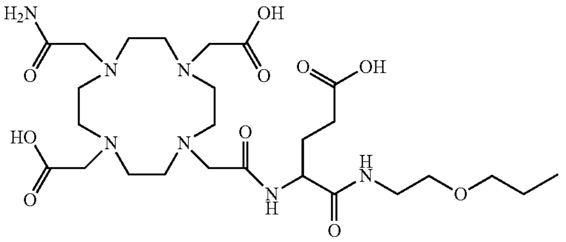
-continued
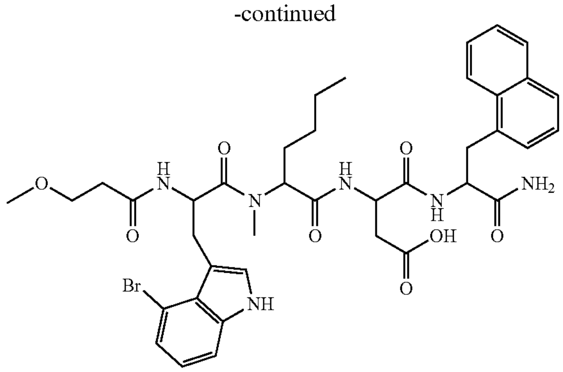
,
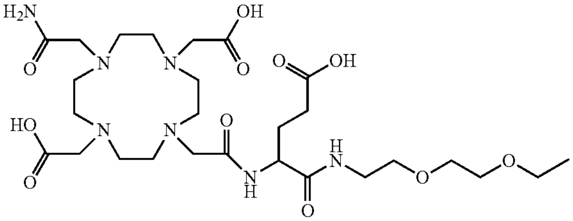
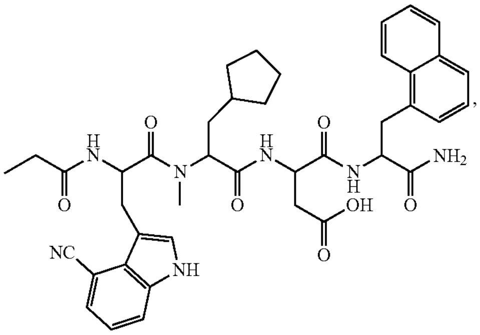
,
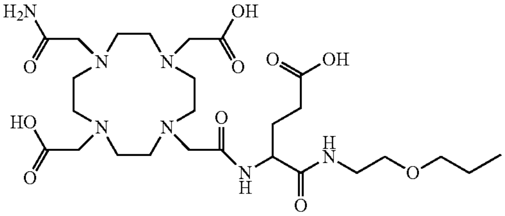
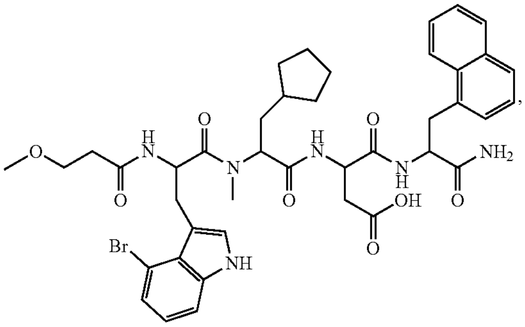
, and -continued

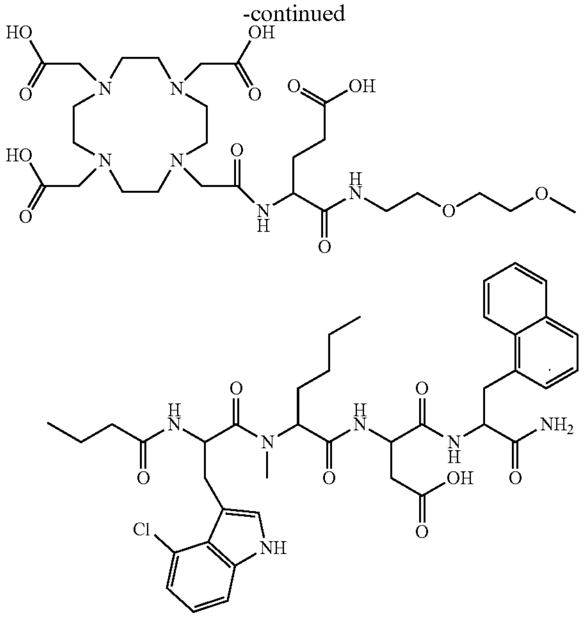

2. The peptidomimetic conjugate according to claim 1, wherein the peptidomimetic conjugate is capable of chelating a radionuclide.

3. The peptidomimetic conjugate according to claim 2, wherein the radionuclide is $^{203}Pb$ or $^{212}Pb$.

4. The peptidomimetic conjugate according to claim 2, wherein the radionuclide is $^{61}Cu$, $^{64}Cu$, $^{67}Cu$, or $^{68}Ga$.

5. A method for imaging or diagnosing a subject suffering from a cancer associated with expression of cholecystokinin-2 receptor (CCK2R), the method comprising administering the peptidomimetic conjugate of claim 1 to the subject, wherein the peptidomimetic conjugate is complexed with a radionuclide suitable for medical imaging use, and imaging the subject.

6. A method for treating a subject suffering from a cancer associated with expression of CCK2R, the method comprising administering the peptidomimetic conjugate of claim 1 to the subject, wherein the peptidomimetic conjugate is complexed with a radionuclide suitable for therapeutic use, in a dosage sufficient to kill cancer cells.

7. A method of diagnosing and treating a subject suffering from a cancer associated with expression of CCK2R, the method comprising:

diagnosing the subject by administering the peptidomimetic conjugate of claim 1 to the subject, wherein the peptidomimetic conjugate is complexed with a radionuclide suitable for medical imaging use, and imaging the subject to diagnose the subject as being afflicted with the cancer, and treating the subject diagnosed as being afflicted by the cancer, by administering the peptidomimetic conjugate of claim 1 to the subject, wherein the peptidomimetic conjugate is complexed with a radionuclide suitable for therapeutic use, in a dosage sufficient to kill cancer cells.

8. The method according to claim 5, wherein the subject is imaged using single-photon emission computed tomography (SPECT) imaging or positron emission tomography (PET), optionally in combination with computed tomography (CT) imaging.

9. The method according to claim 7, wherein the cancer associated with expression of CCK2R is selected from thyroid cancer, lung cancer, tumors of the nervous system, ovarian cancer, gastrointestinal cancer, neuroendocrine tumors, neuroblastoma, endometrial cancer, insulinomas, prostate cancer, breast cancer, vipomas, bronchial carcinoids, ileal carcinoids, and sarcomas.

* * * * *